US012281362B2

(12) United States Patent
Czyzyk-Krzeska et al.

(10) Patent No.: US 12,281,362 B2
(45) Date of Patent: Apr. 22, 2025

(54) DIAGNOSTIC TOOLS AND TREATMENTS FOR CLEAR CELL RENAL CELL CARCINOMA

(71) Applicant: University of Cincinnati, Cincinnati, OH (US)

(72) Inventors: Maria Franciszka Czyzyk-Krzeska, Cincinnati, OH (US); Julio Alberto Landero Figueroa, Cincinnati, OH (US); Jarek Meller, Cincinnati, OH (US); David Plas, Cincinnati, OH (US); Shuchi Gulati, Cincinnati, OH (US); Bhargav Vemuri, Mason, OH (US); John Thomas Cunningham, IV, Maineville, OH (US)

(73) Assignee: University of Cincinnati, Cincinnati, OH (US)

( * ) Notice: Subject to any disclaimer, the term of this patent is extended or adjusted under 35 U.S.C. 154(b) by 401 days.

(21) Appl. No.: 17/327,100

(22) Filed: May 21, 2021

(65) Prior Publication Data

US 2022/0136059 A1 May 5, 2022

Related U.S. Application Data

(60) Provisional application No. 63/110,042, filed on Nov. 5, 2020.

(51) Int. Cl.
*C12Q 1/68* (2018.01)
*C12Q 1/6886* (2018.01)
*G01N 33/574* (2006.01)

(52) U.S. Cl.
CPC ..... *C12Q 1/6886* (2013.01); *G01N 33/57438* (2013.01); *C12Q 2600/118* (2013.01); *C12Q 2600/158* (2013.01); *G01N 2333/90216* (2013.01)

(58) Field of Classification Search
None
See application file for complete search history.

(56) References Cited

PUBLICATIONS

Reigle et al; Journal of Clinical Investigation, Jan. 4, 2021; 131(1), e140522, abstract, pp. 1-16.*

Memmott, R.M., Mercardo, J.R., Maier, C.R., Kawabata, S., Fox, S.D., and Dennis, P.A. (2010). Metformin prevents tobacco carcinogen-induced lung tumorigenesis. Cancer Prev Res (Phila) 3, 1066-1076.

Metallo, C.M., Gameiro, P.A., Bell, E.L., Mattaini attaini, K.R., Yang, J., Hiller, K., Jewell, C.M., Johnson, Z.R., Irvine, D.J., Guarente, L., et al. (2011). Reductive glutamine metabolism by IDH1 mediates lipogenesis under hypoxia. Nature 481, 380-384.

Minarik, P., Tomaskova, N., Kollarova, M., and Antalik, M. (2002). Malate dehydrogenases—structure and function. General physiology and biophysics 21, 257-265.

Mokhtarani, M., Diaz, G.A., Rhead, W., Lichter-Konecki, U., Bartley, J., Feigenbaum, A., Longo, N., Berquist, W., Berry, S.A., Gallagher, R., et al. (2012). Urinary phenylacetylglutamine as dosing biomarker for patients with urea cycle disorders. Molecular genetics and metabolism 107, 308-314.

Molina, J.R., Sun, Y., Protopopova, M., Gera, S., Bandi, M., Bristow, C., Mcafoos, T., Morlacchi. P., Ackroyd, J., Agip, A.A., et al. (2018). An inhibitor of oxidative phosphorylation exploits cancer vulnerability. Nature medicine 24, 1036-1046.

Mullen, A.R., Wheaton, W.W., Jin, E.S., Chen, P.H., Sullivan, L.B., Cheng, T., Yang, Y., Linehan, W.M., Chandel, N.S., and Deberardinis, R.J. (2011). Reductive carboxylation supports growth in tumour cells with defective mitochondria. Nature 481, 385-388.

Naranmandura, H., Xu, S., Sawata, T., Hao, W.H., Liu, H., Bu, N., Ogra, Y., Lou, Y.J., and Suzuki, N. (2011). Mitochondria are the main target organelle for trivalent monomethylarsonous acid (MMA(III))-induced cytotoxicity. Chemical research in toxicology 24, 1094-1103.

Nemeti, B., and Gregus, Z. (2002). Mitochondria work as reactors in reducing arsenate to arsenite. Toxicology and applied pharmacology 182, 208-218.

Nemeti, B., Regonesi, M.E., Tortora, P., and Gregus, Z. (2010). Polynucleotide phosphorylase and mitochondrial ATP synthase mediate reduction of arsenate to the more toxic arsenite by forming arsenylated analogues of ADP and ATP. Toxicological sciences : an official journal of the Society of Toxicology 117, 270-281.

Newman, A.M., Liu, C.L., Green, M.R., Gentles, A.J., Feng, W., Xu, Y., Hoang, C.D., Diehn, M., and Alizadeh, A.A. (2015). Robust enumeration of cell subsets from tissue expression profiles. Nature methods 12, 453-457.

Ochocki, J.D., Khare, S., Hess, M., Ackerman, D., Qiu, B., Daisak, J.I., Worth, A.J., Lin, N., Lee, P., Xie, H., et al. (2018). Arginase 2 Suppresses Renal Carcinoma Progression via Biosynthetic Cofactor Pyridoxal Phosphate Depletion and Increased Polyamine Toxicity. Cell metabolism 27, 1263-1280.e1266.

Olmedo, P., Goessler, W., Tanda, S., Grau-Perez, M., Jarmul, S., Aherrera, A., Chen, R., Hilpert, M., Cohen, J.E., Navas-Acien, A., et al. (2018). Metal Concentrations in e-Cigarette Liquid and Aerosol Samples: The Contribution of Metallic Coils. Environmental health perspectives 126, 027010.

Parker, A., Lohse, C., Cheville, J., Leibovich, B., Igel, T., and Blute, M. (2008). Evaluation of the association of current cigarette smoking and outcome for patients with clear cell renal cell carcinoma. International journal of urology : official journal of the Japanese Urological Association 15, 304-308.

(Continued)

*Primary Examiner* — Jehanne S Sitton
(74) *Attorney, Agent, or Firm* — Brent M. Peebles

(57) ABSTRACT

A method of diagnosing the likelihood of recurrence of clear cell renal cell carcinoma is provided. The method involves a) detecting the gene expression signatures of mitochondrial electron transport chain subunits, mitochondrial ribosomal proteins, major histocompatibility complex class II (MHC-II) proteins or combinations thereof in a kidney tumor tissue sample; and b) determining that the subject has an elevated risk of recurrence of clear cell renal cell carcinoma if the gene expression signatures include certain sequences. In another embodiment, the method uses copper levels to diagnose the likelihood of recurrence of clear cell renal cell carcinoma.

9 Claims, 36 Drawing Sheets

Specification includes a Sequence Listing.

(56) References Cited

PUBLICATIONS

Qiu, B., Ackerman, D., Sanchez, D.J., Li, B., Ochocki, J.D., Grazioli, A., Bobrovnikova-Marjon, E., Diehl, J.A., Keith, B., and Simon, M.C. (2015). HIF2alpha-Dependent Lipid Storage Promotes Endoplasmic Reticulum Homeostasis in Clear-Cell Renal Cell Carcinoma. Cancer discovery 5, 652-667.

Rabinovich, S., Silberman, A., Adler, L., Agron, S., Levin-Zaidman, S., Bahat, A., Porat, Z., Ben-Zeev, E., Geva, I., Itkin, M., et al. (2019). The mitochondrial carrier Citrin plays a role in regulating cellular energy during carcinogenesis. Oncogene.

Rehman, K., and Naranmandura, H. (2013). Double-edged effects of arsenic compounds: anticancer and carcinogenic effects. Current drug metabolism 14, 1029-1041. Rini, B.I., Campbell, S.C., and Escudier, B. (2009). Renal cell carcinoma. Lancet (London, England) 373, 1119-1132.

Sadoul, K., Boyault, C., Pabion, M., and Khochbin, S. (2008). Regulation of protein turnover by acetyltransferases and deacetylases. Biochimie 90, 306-312.

Samudio, I., Fiegl, M., and Andreeff, M. (2009). Mitochondrial uncoupling and the Warburg effect: molecular basis for the reprogramming of cancer cell metabolism. Cancer research 69, 2163-2166.

Sanchez, A., Furberg, H., Kuo, F., Vuong, L., Ged, Y., Patil, S., Ostrovnaya, I., Petruzella, S., Reising, A., Patel, P., et al. (2019). Transcriptomic signatures related to the obesity paradox in patients with clear cell renal cell carcinoma: a cohort study. The Lancet Oncology.

Scaglia, F., Carter, S., O'Brien, W.E., and Lee, B. (2004). Effect of alternative pathway therapy on branched chain amino acid metabolism in urea cycle disorder patients. Molecular genetics and metabolism 81 Suppl 1, S79-85.

Semenza, G.L. (2007). HIF-1 mediates the Warburg effect in clear cell renal carcinoma. Journal of bioenergetics and biomembranes 39, 231-234.

Servillo, L., Castaldo, D., Giovane, A., Casale, R., D'Onofrio, N., Cautela, D., and Balestrieri , M.L. (2018). Ophthalmic acid is a marker of oxidative stress in plants as in animals. Biochimica et biophysica acta General subjects 1862, 991-998.

Simonnet, H., Alazard, N., Pfeiffer, K., Gallou, C., Beroud, C., Demont, J., Bouvier, R., Schagger, H., and Godinot, C. (2002). Low mitochondrial respiratory chain content correlates with tumor aggressiveness in renal cell carcinoma. Carcinogenesis 23, 759-768.

Solanki, H.S., Babu, N., Jain, A.P., Bhat, M.Y., Puttamallesh, V.N., Advani, J., Raja, R., Mangalaparthi, K.K., Kumar, M.M., Prasad, T.S.K., et al. (2018). Cigarette smoke induces mitochondrial metabolic reprogramming in lung cells. Mitochondrion 40, 58-70.

Solmonson, A., and Deberardinis, R.J. (2018). Lipoic acid metabolism and mitochondrial redox regulation. The Journal of biological chemistry 293, 7522-7530.

Sullivan, L.B., Gui, D.Y., Hosios, A.M., Bush, L.N., Freinkman, E., and Vander Heiden, M.G. (2015). Supporting Aspartate Biosynthesis Is an Essential Function of Respiration in Proliferating Cells. Cell 162, 552-563.

Talhout, R., Schulz, T., Florek, E., Van Benthem, J., Wester, P., and Opperhuizen, A. (2011). Hazardous compounds in tobacco smoke. International journal of environmental research and public health 8, 613-628.

Theis, R.P., Dolwick Grieb, S.M., Burr, D., Siddiqui, T., and Asal, N.R. (2008). Smoking, environmental tobacco smoke, and risk of renal cell cancer: a population-based case-control study. BMC cancer 8, 387.

Tomimoto, A., Endo, H., Sugiyama, M., Fujisawa, T., Hosono, K., Takahashi, H., Nakajima, N., Nagashima, Y., Wada, K., Nakagama, H., et al. (2008). Metformin suppresses intestinal polyp growth in ApcMin/+ mice. Cancer Sci 99, 2136-2141.

Tsivian, M., Moreira, D.M., Caso, J.R., Mouraviev, V., and Polascik, T.J. (2011). Cigarette smoking is associated with advanced renal cell carcinoma. Journal of clinical oncology : official journal of the American Society of Clinical Oncology 29, 2027-2031.

Turajlic, S., Xu, H., Litchfield, K., Rowan, A., Horswell, S., Chambers, T., O'Brien, T., Lopez, J.I., Watkins, T.B.K., Nicol, D., et al. (2018). Deterministic Evolutionary Trajectories Influence Primary Tumor Growth: TRACERx Renal. Cell 173, 595-610.e511.

Wang, R., Wang, G., Ricard, M.J., Ferris, B., Strulovici-Barel, Y., Salit, J., Hackett, N.R., Gudas, L.J., and Crystal, R.G. (2010). Smoking-induced upregulation of AKR1B10 expression in the airway epithelium of healthy individuals. Chest 138, 1402-1410.

Warburg, O. (1956a). On respiratory impairment in cancer cells. Science (New York, NY) 124, 269-270.

Warburg, O. (1956b). On the origin of cancer cells. Science (New York, NY) 123, 309-314.

Watanabe, T., and Hirano, S. (2013). Metabolism of arsenic and its toxicological relevance. Archives of toxicology 87, 969-979.

Wheaton, W.W., Weinberg, S.E., Hamanaka, R.B., Soberanes, S., Sullivan, L.B., Anso, E., Glasauer, A., Dufour, E., Mutlu, G.M., Budigner, G.S., et al. (2014). Metformin inhibits mitochondrial complex I of cancer cells to reduce tumorigenesis. eLife 3, e02242.

Xu, Y., Qi, Y., Zhang, J., Lu, Y., Song, J., Dong, B., Kong, W., Xue, W., and Huang, Y. (2014). The impact of smoking on survival in renal cell carcinoma: a systematic review and meta-analysis. Tumour biology : the journal of the International Society for Oncodevelopmental Biology and Medicine 35, 6633-6640.

Zhang, X., Fryknas, M., Hernlund, E., Fayad, W., De Milito, A., Olofsson, M.H., Gogvadze, V., Dang, L., Pahlman, S., Schughart, L.A., et al. (2014). Induction of mitochondrial dysfunction as a strategy for targeting tumour cells in metabolically compromised microenvironments. Nature communications 5, 3295.

Zhang, X., Yang, F., Shim, J.Y., Kirk, K.L., Anderson, D.E., and Chen, X. (2007). Identification of arsenicbinding proteins in human breast cancer cells. Cancer letters 255, 95-106.

Zhao, F., Severson, P., Pacheco, S., Futscher, B.W., and Klimecki, W.T. (2013). Arsenic exposure induces the Warburg effect in cultured human cells. Toxicology and applied pharmacology 271, 72-77.

Zhu, W., Olson, S.Y., and Garban, H. (2011). Transcription regulator Yin-yang 1: from silence to cancer. Critical reviews in oncogenesis 16, 227-238.

Iwai, T., Chiba, K., and Narukawa, T. (2016). Arsenic Speciation and Cadmium Determination in Tobacco Leaves, Ash and Smoke. Analytical sciences : the international journal of the Japan Society for Analytical Chemistry 32, 957-962.

(2013). Comprehensive molecular characterization of clear cell renal cell carcinoma. Nature 499, 43-49.

Ashton, T.M., Mckenna, W.G., Kunz-Schughart, L.A., and Higgins, G.S. (2018). Oxidative Phosphorylation as an Emerging Target in Cancer Therapy. Clinical cancer research : an official journal of the American Association for Cancer Research 24, 2482-2490.

Bergquist, E.R., Fischer, R.J., Sugden, K.D., and Martin, B.D. (2009). Inhibition by methylated organoarsenicals of the respiratory 2-oxo-acid dehydrogenases. Journal of organometallic chemistry 694, 973-980.

Birsoy, K., Wang, T., Chen, W.W., Freinkman, E., Abu-Remaileh, M., and Sabatini, D.M. (2015). An Essential Role of the Mitochondrial Electron Transport Chain in Cell Proliferation Is to Enable Aspartate Synthesis. Cell 162, 540-551.

Blattler, A., Yao, L., Wang, Y., Ye, Z., Jin, V.X., and Farnham, P.J. (2013). ZBTB33 binds unmethylated regions of the genome associated with actively expressed genes. Epigenetics & chromatin 6, 13.

Bridges, H.R., Jones, A.J., Pollak, M.N., and Hirst, J. (2014). Effects of metformin and other biguanides on oxidative phosphorylation in mitochondria. The Biochemical journal 462, 475-487.

Callicutt, C.H., Cox, R.H., Hsu, F., Kinser, R.D., Laffoon, S.W., Lee, P.N., Podraza, K.F., Sanders, E.B., and Seeman, J.I. (2006). The role of ammonia in the transfer of nicotine from tobacco to mainstream smoke. Regulatory toxicology and pharmacology : RTP 46, 1-17.

Campbell, R.C., Stephens, W.E., Finch, A.A., and Geraki, K. (2014). Controls on the valence species of arsenic in tobacco smoke:

(56) References Cited

PUBLICATIONS

Xanes investigation with implications for health and regulation. Environmental science & technology 48, 3449-3456.
Cardaci, S., Zheng, L., Mackay, G., Van Den Broek, N.J., Mackenzie, E.D., Nixon, C., Stevenson, D., Tumanov, S., Bulusu, V., Kamphorst, J.J., et al. (2015). Pyruvate carboxylation enables growth of SDHdeficient cells by supporting aspartate biosynthesis. Nature cell biology 17, 1317-1326.
Chae, Y.K., Arya, A., Malecek, M.K., Shin, D.S., Carneiro, B., Chandra, S., Kaplan, J., Kalyan, A., Altman, J.K., Platanias, L., et al. (2016). Repurposing metformin for cancer treatment: current clinical studies. Oncotarget 7, 40767-40780.
Chen, B., Khodadoust, M.S., Liu, C.L., Newman, A.M., and Alizadeh, A.A. (2018). Profiling Tumor Infiltrating Immune Cells with Cibersort. Methods in molecular biology (Clifton, NJ) 1711, 243-259.
Chen, H., Lee, L.S., Li, G., Tsao, S.W., and Chiu, J.F. (2016). Upregulation of glycolysis and oxidative phosphorylation in benzo[alpha]pyrene and arsenic-induced rat lung epithelial transformed cells. Oncotarget 7, 40674-40689.
Cheng, T., S Udderth, J., Yang, C., Mullen, A.R., Jin, E.S., Mates, J.M., and Deberardinis, R.J. (2011). Pyruvate carboxylase is required for glutamine-independent growth of tumor cells. Proceedings of the National Academy of Sciences of the United States of America 108, 8674-8679.
Cote, M.L., Colt, J.S., Schwartz, K.L., Wacholder, S., Ruterbusch, J.J., Davis, F., Purdue, M., Graubard, B.I., and Chow, W.H. (2012). Cigarette smoking and renal cell carcinoma risk among black and white Americans: effect modification by hypertension and obesity. Cancer epidemiology, biomarkers & prevention : a publication of the American Association for Cancer Research, cosponsored by the American Society of Preventive Oncology 21, 770-779.
Courtney, K.D., Bezwada, D., Mashimo, T., Pichumani, K., Vemireddy, V., Funk, A.M., Wimberly, J., Mcneil, S.S., Kapur, P., Lotan, Y., et al. (2018). Isotope Tracing of Human Clear Cell Renal Cell Carcinomas Demonstrates Suppressed Glucose Oxidation In Vivo. Cell metabolism 28, 793-800.e792.
Cunningham, J.T., Rodgers, J.T., Arlow, D.H., Vazquez, F., Mootha, V.K., and Puigserver, P. (2007). mTOR controls mitochondrial oxidative function through a YY1-PGC-1alpha transcriptional complex. Nature 450, 736-740.
Das, B., Ray, T., Panda, K.K., Maiti, A., Sarkar, S., and Sil, A.K. (2014). Leucine and its transporter provide protection against cigarette smoke-induced cell death: A potential therapy for emphysema. Toxicology reports 1, 752-763.
De Jong, F.A., and Beecher, C. (2012). Addressing the current bottlenecks of metabolomics: Isotopic Ratio Outlier Analysis, an isotopic-labeling technique for accurate biochemical profiling. Bioanalysis 4, 2303-2314.
Dello, S.A., Neis, E.P., De Jong, M.C., Van Eijk, H.M., Kicken, C.H., Olde Damink, S.W., and Dejong, C.H. (2013). Systematic review of ophthalmate as a novel biomarker of hepatic glutathione depletion. Clinical nutrition (Edinburgh, Scotland) 32, 325-330.
Dowling, R.J., Niraula, S., Stambolic, V., and Goodwin, P.J. (2012). Metformin in cancer: translational challenges. J Mol Endocrinol 48, R31-43.
Ehdaie, B., Furberg, H., Zabor, E.C., Hakimi, A.A., and Russo, P. (2014). Comprehensive assessment of the impact of cigarette smoking on survival of clear cell kidney cancer. The Journal of urology 191, 597-602.
Enns, G.M., Berry, S.A., Berry, G.T., Rhead, W.J., Brusilow, S.W., and Hamosh, A. (2007). Survival after treatment with phenylacetate and benzoate for urea-cycle disorders. The New England journal of medicine 356, 2282-2292.
Evans, J.M., Donnelly, L.A., Emslie-Smith, A.M., Alessi, D.R., and Morris, A.D. (2005). Metformin and reduced risk of cancer in diabetic patients. Bmj 330, 1304-1305.
Everett, J.R., Holmes, E., Veselkov, K.A., Lindon, J.C., and Nicholson, J.K. (2019). A Unified Conceptual Framework for Metabolic Phenotyping in Diagnosis and Prognosis. Trends in pharmacological sciences 40, 763-773.
Fajkovic, H., Shariat, S.F., Klatte, T., Vartolomei, M.D., Lucca, I., Mbeutcha, A., Roupret, M., Briganti, A.,Karakiewicz, P.I., Margulis, V., et al. (2016). Impact of smoking status on survival after cytoreductive nephrectomy for metastatic renal cell carcinoma. World J Urol 34, 1411-1419.
Gameiro, P.A., Laviolette, L.A., Kelleher, J.K., Iliopoulos, O., and Stephanopoulos, G. (2013a). Cofactor balance by nicotinamide nucleotide transhydrogenase (NNT) coordinates reductive carboxylation and glucose catabolism in the tricarboxylic acid (TCA) cycle. The Journal of biological chemistry 288, 12967-12977.
Gameiro, P.A., Yang, J., Metelo, A.M., Perez-Carro, R., Baker, R., Wang, Z., Arreola, A., Rathmell, W.K., Olumi, A., Lopez-Larrubia, P., et al. (2013b). In vivo HIF-mediated reductive carboxylation is regulated by citrate levels and sensitizes VHL-deficient cells to glutamine deprivation. Cell metabolism 17, 372-385.
Garcia-Bermudez, J., Baudrier, L., La, K., Zhu, X.G., Fidelin, J., Sviderskiy, V.O., Papagiannakopoulos, T., Molina, H., Snuderl, M., Lewis, C.A., et al. (2018). Aspartate is a limiting metabolite for cancer cell proliferation under hypoxia and in tumours. Nature cell biology 20, 775-781.
Gatto, F., Nookaew, I., and Nielsen, J. (2014). Chromosome 3p loss of heterozygosity is associated with a unique metabolic network in clear cell renal carcinoma. Proceedings of the National Academy of Sciences of the United States of America 111, E866-875.
Gui, D.Y., Sullivan, L.B., Luengo, A., Hosios, A.M., Bush, L.N., Gitego, N., Davidson, S.M., Freinkman, E.,Thomas, C.J., and Vander Heiden, M.G. (2016). Environment Dictates Dependence on Mitochondrial Complex I for NAD+ and Aspartate Production and Determines Cancer Cell Sensitivity to Metformin. Cell metabolism 24, 716-727.
Hakimi, A.A., Furberg, H., Zabor, E.C., Jacobsen, A., Schultz, N., Ciriello, G., Mikklineni, N., Fiegoli, B., Kim, P.H., Voss, M.H., et al. (2013). An epidemiologic and genomic investigation into the obesity paradox in renal cell carcinoma. Journal of the National Cancer Institute 105, 1862-1870.
Hakimi, A.A., Reznik, E., Lee, C.H., Creighton, C.J., Brannon, A.R., Luna, A., Aksoy, B.A., Liu, E.M., Shen, R., Lee, W., et al. (2016). An Integrated Metabolic Atlas of Clear Cell Renal Cell Carcinoma. Cancer cell 29, 104-116.
Hunt, J.D., Van Der Hel, O.L., Mcmillan, G.P., Boffetta, P., and Brennan, P. (2005). Renal cell carcinoma in relation to cigarette smoking: meta-analysis of 24 studies. International journal of cancer 114, 101-108.
Jain, I.H., Zazzeron, L., Goli, R., Alexa, K., Schatzman-Bone, S., Dhillon, H., Goldberger, O., Peng, J., Shalem, O., Sanjana, N.E., et al. (2016). Hypoxia as a therapy for mitochondrial disease. Science (New York, NY) 352, 54-61.
Kanarek, N., Keys, H.R., Cantor, J.R., Lewis, C.A., Chan, S.H., Kunchok, T., Abu-Remaileh, M., Freinkman, E., Schweitzer, L.D., and Sabatini, D.M. (2018). Histidine catabolism is a major determinant of methotrexate sensitivity. Nature 559, 632-636.
Karu, T.I. (2010). Multiple roles of cytochrome c oxidase in mammalian cells under action of red and IR-A radiation. IUBMB life 62, 607-610.
Kawasaki, H., Schiltz, L., Chiu, R., Itakura, K., Taira, K., Nakatani, Y., and Yokoyami, K.K. (2000). ATF-2 has intrinsic histone acetyltransferase activity which is modulated by phosphorylation. Nature 405, 195-200.
Kim, J.W., Tchernyshyov, I., Semenza, G.L., and Dang, C.V. (2006). HIF-1-mediated expression of pyruvate dehydrogenase kinase: a metabolic switch required for cellular adaptation to hypoxia. Cell metabolism 3, 177-185.
Kobayashi, K., Hisamatsu, K., Suzui, N., Hara, A., Tomita, H., and Miyazaki, T. (2018). A Review of HPVRelated Head and Neck Cancer. J Clin Med 7.
Kroeger, N., Klatte, T., Birkhauser, F.D., Rampersaud, E.N., Seligson, D.B., Zomorodian, N., Kabbinavar, F.F., Belldegrun, A.S., and Pantuck, A.J. (2012). Smoking negatively impacts renal cell carcinoma overall and cancer-specific survival. Cancer 118, 1795-1802.
Lagory, E.L., Wu, C., Taniguchi, C.M., Ding, C.C., Chi, J.T., Von Eyben, R., Scott, D.A., Richardson, A.D., and Giaccia, A.J. (2015). Suppression of PGC-1alpha Is Critical for Reprogramming Oxidative Metabolism in Renal Cell Carcinoma. Cell reports 12, 116-127.

(56) References Cited

PUBLICATIONS

Lee, B., Rhead, W., Diaz, G.A., Scharschmidt, B.F., Mian, A., Shchelochkov, O., Marier, J.F., Beliveau, M., Mauney, J., Dickinson, K., et al. (2010). Phase 2 comparison of a novel ammonia scavenging agent with sodium phenylbutyrate in patients with urea cycle disorders: safety, pharmacokinetics and ammonia control. Molecular genetics and metabolism 100, 221-228.

Lee, J.S., Adler, L., Karathia, H., Carmel, N., Rabinovich, S., Auslander, N., Keshet, R., Stettner, N., Silberman, A., Agemy, L., et al. (2018). Urea Cycle Dysregulation Generates Clinically Relevant Genomic and Biochemical Signatures. Cell 174, 1559-1570.e1522.

Li, B., Qiu, B., Lee, D.S., Walton, Z.E., Ochocki, J.D., Mathew, L.K., Mancuso, A., Gade, T.P., Keith, B., Nissim, I., et al. (2014). Fructose-1,6-bisphosphatase opposes renal carcinoma progression. Nature 513, 251-255.

Lucarelli, G., Galleggiante, V., Rutigliano, M., Sanguedolce, F., Cagiano, S., Bufo, P., Lastilla, G., Maiorano, E., Ribatti, D., Giglio, A., et al. (2015). Metabolomic profile of glycolysis and the pentose phosphate pathway identifies the central role of glucose-6-phosphate dehydrogenase in clear cell-renal cell carcinoma. Oncotarget 6, 13371-13386.

Luz, A.L., Godebo, T.R., Smith, L.L., Leuthner, T.C., Maurer, L.L., and Meyer, J.N. (2017). Deficiencies in mitochondrial dynamics sensitize Caenorhabditis elegans to arsenite and other mitochondrial toxicants by reducing mitochondrial adaptability. Toxicology 387, 81-94.

Luz, A.T., Godebo, T.R., Bhatt, D.P., Ilkayeva, O.R., Maurer, L.L., Hirschey, M.D., and Meyer, J.N. (2016). Arsenite Uncouples Mitochondrial Respiration and Induces a Warburg-Like Effect in Caenorhabditis elegans. Toxicological sciences : an official journal of the Society of Toxicology 154, 195.

Mclaughlin, J.K., Hrubec, Z., Heineman, E.F., Blot, W.J., and Fraumeni, J.F., Jr. (1990). Renal cancer and cigarette smoking in a 26-year followup of U.S. veterans. Public health reports (Washington, DC : 1974) 105, 535-537.

Melamud, E., Vastag, L., and Rabinowitz, J.D. (2010). Metabolomic analysis and visualization engine for LC-MS data. Analytical chemistry 82, 9818-9826.

* cited by examiner

FIG. 5

SEQ ID NO:1 aggacacgtg ggtgggggaa gctgagcgct gagaccaagg gctaaagctg ggaggtgagt 60
ctgtcacctt gagccgggcg agcgctgtgg gccaagcagg ggttgcaggg tagtaggagt 120
gcagactgaa aaaatgcaga ccgccggggc attattcatt tctccagctc tgatccgctg 180
ttgtaccagg ggtctaatca ggcctgtgtc tgcctccttc ttgaatagcc cagtgaattc 240
atctaaacag ccttcctaca gcaacttccc actccaggtg gccagacggg agttccagac 300
cagtgttgtc tcccgggaca ttgacacagc agccaagttt attggtgctg gggcagccac 360
agttggtgtg gctggttcag gggctggcat tggaaccgtg tttggcagct tgatcattgg 420
ctatgccagg aacccgtctc tcaagcagca gctcttctcc tatgccattc ttggctttgc 480
cctgtctgag gccatggggc ttttctgttt gatggtcgcc ttcctcatcc tcttcgccat 540
gtgaggctcc atgggggggt caccggcctg ttgctactgc aactccacac cattcttggt 600
gctggggtgt gttaagcttt accattaaac acaacgtttc tctaaa 646

FIG. 6

SEQ ID NO:2 gcagtccacg ttacggatcg gcttactccg cggagttggc ctcatttctg cagtcggcgc 60
tccctgtagt ttctcctctc gaacgccagg tggagcaacc ggccggatac cgcccacagcc 120
ctggcaggcg gcgctgtgat gcctgagctg atcctctctc ctgccacagc tcctcacccc 180
ctgaaaatgt tcgcctgctc caagtttgtc tccactccct ccttggtcaa gagcacctca 240
cagctgctga gccgtccgct atctgcagtg gtgctgaaac gaccggagat actgacagat 300
gagagcctca gcagcttggc agtctcatgt ccccttacct cacttgtctc tagccgcagc 360
ttccaaacca gcgccatttc aagggacatc gacacagcag ccaagttcat tggagctggg 420
gctgccacag ttggggtggc tggttctggg gctgggattg gaactgtgtt tgggagcctc 480
atcattggtt atgccaggaa cccttctctg aagcaacagc tcttctccta cgccattctg 540
ggctttgccc tctcggaggc catggggctc ttttgtctga tggtagcctt tctcatcctc 600
tttgccatgt gaaggagccg tctccacctc ccatagttct cccgcgtctg gttggccccg 660
tgtgttcctt ttcctatacc tccccaggca gcctggggaa cgtggttggc tcagggtttg 720
acagagaaaa gacaaataaa tactgtatta ataaga 756

FIG. 7

SEQ ID NO:3 accgcgaagg gaggagtggc aacatggcgt cttcgggagc tggtgaccct ctggattcta 60
agcgtggaga ggccccgttc gctcagcgta tcgacccgac tcgggagaag ctgacacccg 120
agcaactgca ttccatgcgg caggcggagc ttgcccagtg gcagaaggtc ctaccacggc 180
ggcgaacccg gaacatcgtg accggcctag gcatcggggc cctggtgttg gctatttatg 240
gttacacctt ctactcgatt tcccaggagc gtttcctaga tgagctagaa gacgaggcca 300
aagctgcccg agcccgagct ctggcaaggg cgtcagggtc ctaatctgga tgggtattga 360
tcatgtccaa cctgctggag ccccttcaca tggtggatga tgccccatga ccctgtagaa 420
attgaatcct gctcacaaca ttgttggcct tcttactaac cttggaccgt gattgagccc 480
aagaaaccag ggacttacgc atttggccaa tgtcaaaaga acagaacttt gcccactgca 540
cacttgctgt gtacaatgac tgagcccttt cttgtagttt gtttccttgt ttgagaggtg 600
tgcatgcgac cgtggctttt cccaaagttt ctgactttgt ggtttacccc cttcaccttc 660
cagggacgca gttgttacga ggttagacgt ggcagctctg tgcagtgttt gagcctacag 720
tgggatacat agggtcaaat tgagaataat aaactgagtc attctcctgg agtcaagtga 780

FIG. 8A

SEQ ID NO:4 gtcaccgagt cgttggcgct gtcatggcgg gtgtgctgaa gaagaccact ggccttgtgg 60
gattggctgt gtgcaatact cctcacgaga ggctaagaat attgtacaca aagattcttg 120
atgttcttga ggaaatccct aaaaatgcag catatagaaa gtatacagaa cagattacaa 180
atgagaagct ggctatggtt aaagcggaac cagatgttaa aaaattagaa gaccaacttc 240
aaggcggtca attagaagag gtgattcttc aggctgaaca tgaactaaat ctggcaagaa 300
aaatgaggga atggaaacta tgggagccat tagtggaaga gcctcctgcc gatcagtgga 360
aatggccaat ataattatta agtgactttg gtgtgttcat gggaaactga tgtaattaaa 420
tattctgtta tattaagagc gtgttcttat tactgacatt ttgtaatcaa gaaaagtgat 480
atagaaaata tgtaggagac tgttaaaatt ggtgattatg gtaatatggt catgtgaatc 540
aatttttgat ttataaagta ctcacacaag ttgtttcaaa gatgatattt ctgtgaacag 600
agaggccatg ggaagatttg aaaattatta aagaaaaatt cctacagatt ttcaatgcag 660
agaccataat caaaaagtaa actttcttta gtagtatgtt caatacatca tttaattttt 720
taagttatcc tgaagaagga aaggtcctta attattatag tctaaacaaa tttatagatt 780
actgtttgaa gtaaataata cgagtgaata ttttcaaatg tgataaaata gcacaagtgg 840
ctggtgataa aatttgaaat tatggttaac ctcagctgtg atcttatgta tgtaaagtga 900
aatttaaata gataattata ggttgattac aaaatccata gtgtcatttt attttagtca 960
ttattgaatt ataccattta ctctgttttc ttatagtctt aattttatta tattttgttg 1020
ttactgtatt atatttgaaa accttcaaat tagaatacat tgtacagtta aagaaattga 1080
cttggtactt aaaagaaaga tttcccattg catacaggtt attggagaaa ttttcctttt 1140
gttgcatttg tggaagttag ttttctggcc cgtggccttt aattttctta atcaacctaa 1200
ttacatcagg atagaggtag agtttctgta aaagaagaga cattaagagt tcctgaaatt 1260
tatatctggc atacggatag gcttatattc aaaacatctt agtcatacga ccataaatta 1320
aaagtggagt cactaaatag tttgcagtac gtttctaata taagtgtagg tgggtatcaa 1380
aacaagacaa atgctgttca gggaaagaag ttggcaagct taaggttaaa caaaaataaa 1440
attacatgtg ttttcgcctt cctagctccc tgtcattcct aaatacttgg ttaaatttaa 1500
cgtggtatct ctttccttca tagatagtac tatactcttg tggggttttg tgtatacgtg 1560
tgtgtgtgtg tgtgtgtgtg tgtgtgtgtg tgtgtgtgtg tgcacgcgca tgcgcacatt 1620
tgctcagaat gagaaaaaaa tggtattttt ccttctttcc agtatatttc tcccctcata 1680

FIG. 8B gagctgtaac atgaatacta aataaatatt aaataaggtg gattcttaga ggttagagtg 1740
caagaaggct ccttctggtg gggaagtgtt agagggggag ttagaagccc agggtttctc 1800
attctcatgg ttctagtgtt gttaactcaa tgactacatt gaggcaagtt tggcctgttt 1860
ctcagaatgg cctatttcta atgctgcaaa agaaatagaa tatgatttat aacaacattt 1920
tcagttctaa acatttcttg aatatataat atatttatta aaacatgatg ctgaagtgtg 1980
tttgcatggg tactttcaag gtaattttct agccaaccat tatttttcag gtcctttgga 2040
caacacagaa acaaagatgg cttgctgtgt ttttgtcata ttttcagtcc cgtatctgcc 2100
atgattcttg ggcatctttt atgtttcacc aacagtgtta ctgaactttt ttgctaaaag 2160
gggaccttac tggtgtttgc attagaaatg ctagttgcag aataatagtc attgtaaaaa 2220
taatattata acaataatag ctaatgtttg ttgagacttt aatatgaatg tcaggcacta 2280
tcataagtac ctgactaatt tcactcatta aacctgcact acaaccctaa gagtgatact 2340
acaaattatc ttcattttcc agataagaaa ccagaaccct acgtgagtag ttttcccctg 2400
caattatgca acttggggcc ttggggacac tgaaaccaag agatgattta ataacaaatc 2460
caaggtcaca tagctagtaa gatgtgaagc tgaagtttga acccaggcag tctggttcta 2520
gaactgatgc tcctgttata ttattattta tgaatatgct tgggatgttg tgacttcttc 2580
ctgtgctgta tgggctgtac caaatgaaac tagatcctgc tctctttacc ttttctgtca 2640
aaattatctg taaagaacaa atatgagcag aagtagtaaa cgatttcatt ttctgcaaag 2700
agctgcatat aggttatagg cagattatgt taatgggata ggtatctaaa aggtattgca 2760
atttggtcat tggttctttc tcctgtctca attgctcaca gaactttaca cctgatcgtt 2820
tttactcctt cagtcttttc ccagttgctt cctataaaca tccaggttaa gtctcctgat 2880
cactttgcaa atgattcttt tattcagaga tcttcagtgt tttgagtggc tactaaacta 2940
attttaataa ttttcagaat ggcctatttc agttctccca tgggtttcat tctagttaat 3000
catcatactg cagatacttc aaaagaaaga gaagctaatc aatttgagct ttgctaagaa 3060
agaagaaatg gcaacaaagt tgatgccccc tttctcccac actgggactt agtgcagacg 3120
attccaattt cttggcattc tttcctttgg gatgaaaatg gcttatattt aggataacta 3180
taggataatt tatcattcca cttggaatga ttttgagtga aaataattac ataaggataa 3240
cagatgtaca ccatgactgt cctgggcaaa caagatatag gggggcaccc tactggagta 3300
aggctcaggt ctcaaggttg ccatctttcc cacaccagta ggatcaacta gtctgtcatt 3360
ggaatagaat gaattgatgc cagcagtagt agtcatcatg tgcaatcagg cctcaagttt 3420
tattgtatcc tttcactctc cctcattctc ccctccccct ccttttccct cagaattggg 3480
ggatggaaga aaagagagct tatattttat tgtcaatttt ctaatcacat tcagaggagc 3540

FIG. 8C gaagctaatt aagccaataa caatgtttat gaatgtatct tttttaaaag ggagatgaca 3600
atatatagga aaattcccac atgtaggcta atagcagctt tttctttttc ctcccatcct 3660
ctatgattat gtaaacatac agaagtctaa caccctacac aagtgtattg tggggtatgg 3720
gattaagtac caaattgctg aacatatcac tagtattttg gatttgctga gtgcagtctt 3780
cccattaaaa ctaagtgttc agtagggagg cgtggtggct cacacctata atcccactac 3840
tttgggaggc cgaggtgggt ggatcacttg aggtcaaaag ttcgaggcca gcctggccaa 3900
tatggtgaaa ccccgtctct actaaaaaca aaaacaaaaa ctaagtgttc agtgagattg 3960
tagcctatgc tacaacaata gtaatgccaa ttgttttaga gaaaagtaaa tgagaggcta 4020
ccagttgtgt ttagaggagg tcgacgtttt attttagaca aaattcacag gaaatcacag 4080
tgggaatgtg ataaggggtt tgaatgattg atggggacag gaagaattca tttgagagac 4140
tagagatgag tcagtattct agatcgtgaa gtaaaatagt gagtcatgta gtgacttagc 4200
atgggttatc cttaaatccc agtgtcttaa gtgtattttt tattcatact gcatgtctaa 4260
ggagggttgg caaggagtgc tcatagaccc acaaggaatc caggctgagt gtggcaccat 4320
caacatatat ttccatgacc atagtggtgg tggggaattg gaacatggta aattacacat 4380
aggaataaaa aaaaagaaac aaccaaggtt aaattttttt ttgactgtgc cacaaaattt 4440
atgaattgaa cttgccatgc atcactaata attttcaaat tggtctttag gtttacatta 4500
gcagctaatt ttttgtggta cacttaaatg taatttatga ttggcatctg tatataatta 4560
aatgaaaagc attgcaaaga tttctatttt ggtatttctc atgatcttca attttttttt 4620
aggtgaatct attaggtttt ctaaagataa ctattttttt ttttttacaa aatattggca 4680
ttttaatctc tctataactg gagggtgaat tatttttcac cagagtaaaa caggtccaaa 4740
gtcccttatc taaattccta atttcaaaaa tctctgaaaa caaagttttt tcataactca 4800
tttggcaaca aaccccacct gaattacatg aggctatttg tggtatttat cgcacttcaa 4860
tgtgaatatg aatatatttt gccacagatg tatcaatata tttgattcta aactgcttcc 4920
tcagaccctc ttaatgtgtt acataatgta aagtatatgc ccatatttcc tttcaaaaat 4980
ctgaaaaatt gtgaatatca aacacatctg tcttaaaagg tttcagaaaa gggacaatag 5040
acctatattt ccattctctt aacaagttca caaagtggta ttatgatcca aatttaatct 5100
aaataatttc caaaacaaaa attttcaggt ccttagtttt ctaaattatt ttaatattaa 5160
aaatattcat tattcatttt aacctgtagt aacaacagga gatactttga aatgcttgat 5220
tttatcaagc cactaggtgg catctttgta aaaataaaag cacatcaaaa gaaatgttta 5280
ttacataaat aaatgctgag atgaataaag gtagatgttt catgagaaat acgaagtcgt 5340
ttggtggaat aaatcctgag aaaatgcata gatttatcat gaaaaggaaa atggaaaatg 5400

FIG. 8D gtattgtaaa attactcttt cacttttgga attgagaagc tttttcctat tggttgtttt 5460
cattaagttt gaatataaat ttattatgta accaaa 5496

FIG. 9

SEQ ID NO:5 gcagtgcatc ctgggttggc gtagccatgg cgtctcgtgt cctttcagcc tatgtcagcc 60
gcctgcccgc ggcctttgcg ccgctgcccc gggtccggat gctggccgtg gcccggcctc 120
tcagcaccgc tctctgctcc gcggggaccc agacgaggct cgggactttg cagccggcct 180
tagtgctcgc gcaggttcct ggtagagtta cacagttgtg ccgccagtat agcgacatgc 240
ctcctttgac gttagagggc atccaggacc gtgttcttta cgtattgaaa ctctatgaca 300
agattgaccc agagaagctt tcagtaaatt ctcattttat gaaagacctg ggcttagaca 360
gtttggacca agtggagatt atcatggcca tggaagacga atttgggttt gaaattcctg 420
atatagatgc tgaaaagtta atgtgtccac aagaaattgt agattacatt gcagataaga 480
aggatgtata tgaataaagt atcagaccct ttggctttgc tgagagagga ctcagatgat 540
agtgacgaat gtctggcagt gaggacacat tttggcattc ttgctgactc tgacagagtg 600
attctgatgg acttgtattt aaattgtatg tgttttactc tttgaaaata aatctataaa 660
accaa 665

FIG. 10

SEQ ID NO:6 gacttcgccg cgcgttggtc agccatggcc accgctctcg cgctacgtag cttgtaccga 60
gcgcgaccct cgctgcgctg tccgcccgtt gagcttccct gggccccgcg gcgagggcat 120
cggctctcgc cggcggatga cgagctgtat cagcggacgc gcatctctct gctgcaacgc 180
gaggccgctc aggcaatgta catcgacagc tacaacagcc gcggcttcat gataaacgga 240
aaccgcgtgc tcggcccctg cgctctgctc ccgcactcgg tggtgcagtg gaacgtggga 300
tcccaccagg acatcaccga agacagcttt tccctcttct ggttgctgga gccccggata 360
gagatcgtgg tggtggggac tggagaccgg accgagaggc tgcagtccca ggtgcttcaa 420
gccatgaggc agcggggcat tgctgtggaa gtgcaggaca cgcccaatgc ctgtgccacc 480
ttcaacttcc tgtgtcatga aggccgagta actggagctg ctctcatccc tccaccagga 540
gggacttcac ttacatcttt gggccaagct gctcaatgaa ccgccaggaa ctgacctgct 600
gactgcactc tgccaggctt cccaatgctt tcactcttat ctaccctttg gcacttatct 660
tgcttatcaa cataataatt tatacacttc tcccattttg tatcaggtgt gttgctggcc 720
aggagctgat ggctcactgg gctcttggag gggaatgtga agaaaccaag gagtcacttt 780
ttcatctaga ttacttagga ttccttgact tttcagaagt cgggaagcag tatgtttgcc 840
tgttgtagac ctacttgctc acatgcagat ttgagaggac ctcaacggct tttctcacaa 900
aa 902

FIG. 11

SEQ ID NO:7 agtctgcatc tgagtaacat ggcggcggcg gcggtagcca ggctgtggtg gcgcgggatc 60
ttgggggcct cggcgctgac cagggggact gggcgaccct ccgttctgtt gctgccggtg 120
aggcgggaga gcgccggggc cgacacgcgc cccactgtca gaccacggaa tgatgtggcc 180
cacaagcagc tctcagcttt tggagagtat gtggctgaaa tcttgcccaa gtatgtccaa 240
caagttcagg tgtcctgctt caatgagtta gaggtctgta tccatcctga tggcgtcatc 300
ccagtgctga ctttcctcag ggatcacacc aatgcacagt tcaaatctct ggttgacttg 360
acagcagtgg acgtcccaac tcggcaaaac cgttttgaga ttgtctacaa cctgttgtct 420
ctgcgcttca actcacggat ccgtgtgaag acctacacag atgagctgac gcccattgag 480
tctgctgtct ctgtgttcaa ggcagccaac tggtatgaaa gggagatctg ggacatgttt 540
ggagtcttct ttgctaacca ccctgatcta agaaggatcc tgacagatta tggcttcgag 600
ggacatcctt tccggaaaga ctttcctcta tctggctatg ttgagttacg ttatgatgat 660
gaagtgaagc gggtggtggc agagccggtg gagttggccc aagagttccg caaatttgac 720
ctgaacagcc cctgggaggc tttcccagtc tatcgccaac cccggagag tctcaagctt 780
gaagccggag acaagaagcc tgatgccaag tagctccagg gaacgcatgt ggatcctaga 840
cagcgcctta tctatgattg agtgtccgtg taaataaatt cctacttaga ctta 894

FIG. 12

SEQ ID NO:8

```
gcaacagggc cgactgcagc tggaagatgg cggcgtccgt ggtctgtcgg gccgctaccg      60
ccggggcaca agtgctattg cgcgcccgcc gctcgccggc cctgctgcgg acgccagcct     120
tgcggagtac ggcaaccttc gctcaggcgc tccagttcgt gccggagacg caggttagcc     180
tgctggacaa cggcctgcgt gtggcctccg agcagtcctc tcagcccact tgcacggtgg     240
gagtgtggat tgatgttggc agccgttttg agactgagaa gaataatggg gcaggctact     300
ttttggagca tctggctttc aagggaacaa agaatcggcc tggcagtgcc ctggagaagg     360
aggtggagag catgggggcc catcttaatg cctacagcac ccgggagcac acagcttact     420
acatcaaggc gctgtccaag gatctgccga aagctgtgga gctcctgggt gacattgtgc     480
agaactgtag tctggaagac tcacagattg agaaggaacg tgatgtgatc ctgcgggaga     540
tgcaggagaa tgatgcatct atgcgagatg tggtctttaa ctacctgcat gccacagcat     600
tccagggcac acctctagcc caggctgtgg aggggcccag tgagaatgtc aggaagctgt     660
ctcgtgcaga cttgaccgag tacctcagca cacattacaa ggccccctcga atggtgctgg    720
cagcagctgg aggagtggag caccagcaac tgttagacct cgcccagaag cacctcggtg     780
gcatcccatg gacatatgca gaggacgctg tgcccactct tactccatgc cgcttcactg     840
gcagtgagat ccgccaccgt gatgatgctc taccttttgc ccacgtggcc attgcagtag     900
agggtcctgg ctgggccagc ccggacaatg tggccttgca agtggccaat gccatcatcg     960
gccactatga ctgcacttat ggtggtggcg tgcacctgtc cagcccactg gcttcaggtg    1020
ctgtggccaa caagctatgc cagagtttcc agaccttcag catctgctat gcagagacgg    1080
gcttgctggg tgcacacttt gtctgtgacc gaatgaaaat cgatgacatg atgttcgtcc    1140
tgcaagggca gtggatgcgc ctgtgtacca gtgccacgga gagtgaggtg gcccggggca    1200
aaaacatcct cagaaatgcc ctggtatctc atctagatgg cactactcct gtgtgtgagg    1260
acatcggacg cagcctcctg acctatggcc gccgcatccc cctggctgaa tgggaaagcc    1320
ggattgcgga ggtggatgcc agtgtggtac gtgagatctg ctccaagtac atctatgacc    1380
agtgcccagc agtggctgga tatggcccca ttgagcagct cccagactac aaccggatcc    1440
gtagcggcat gttctggctg cgcttctagg cgggaagcct atgtaagcaa gagggcaggg    1500
ccggggtttg tggtcccccc cccaccacaa acacagcact tcggctcctc taacctgtgc    1560
cacaggtgac caccaataaa atcctctgct gagaa                                1595
```

FIG. 13

SEQ ID NO:9 gtcatttccg gctcgaatgc ccggcagccg tggcggctag agcgttcctc cccagctcga 60
atgcccggcg gccgaggcgg ctagagcgtc gcctcctccc ggggaaccgc gtgtgacctt 120
ccagcccgcg gaccgatgct gccggcggcc gctcgccccc tgtgggggcc ttgccttggg 180
cttcgggccg ctgcgttccg ccttgccagg cgacaggtgc catgtgtctg tgccgtgcga 240
catatgagga gcagcggcca tcagaggtgt gaggccctcg ctggtgcacc cctggataac 300
gcccccaagg agtacccccc caagatacag cagctggtcc aggacatcgc cagcctcact 360
ctcttggaaa tctcagacct caacgagctc ctgaagaaaa cgttgaagat ccaggatgtc 420
gggcttgtgc cgatgggtgg tgtgatgtct ggggctgtcc ctgctgcagc agcccaggag 480
gcggtggaag aagatatccc catagcgaaa gaacggacac atttcaccgt ccgcctgacc 540
gaggcgaagc ccgtggacaa agtgaagctg atcaaggaaa tcaagaacta catccaaggc 600
atcaacctcg tccaggcaaa gaagctggtg gagtccctgc cccaggaaat caaagccaat 660
gtcgccaaag ctgaggcgga gaagatcaag gcggccctgg aggcggtggg cggcaccgtg 720
gttctggagt agcctccagc tcggaggact tgtgttcagg ggtcctgggc cccgggcgag 780
gtcccgccct cccgtggtca ctggctccgc ccccagcacc aggcgcccag tggagccgtt 840
tgggagaatt gcctgcgcca cgcagcgggg ccggacaggc cgcacagacc tactgtggcg 900
ggagggaggg gcggctgctg cctggtgacg gcacccggag gcccaccagg acgcgccacc 960
ggtgaatgtg cctctggtgg ctgctgagaa aaatacactg tgcagctca 1009

FIG. 14

SEQ ID NO:10

```
gtccgccggg ctgggcctgg cgcgcaggcg ctaggaagag gccgcgtggg gcgaaggcgg 60
cgcttggctg gtggggcccg cggcgggatt ttcccgggcg gcgagagcgg atctatcttg 120
ggatcccatg gctttcttta ctgggctctg gggccccttc acctgtgtaa gcagagtgct 180
gagccatcac tgtttcagca ccactgggag tctgagtgcg attcagaaga tgacgcgggt 240
acgagtggtg gacaacagtg ccctggggaa cagcccatac catcgggctc ctcgctgcat 300
ccatgtctat aagaagaatg gagtgggcaa ggtgggcgac cagatactac tggccatcaa 360
gggacagaag aaaaaggcgc tcattgtggg gcactgcatg cctggccccc gaatgacccc 420
cagattcgac tccaacaacg tggtcctcat tgaggacaac gggaaccctg tggggacacg 480
aattaagaca cccatcccca ccagcctgcg caagcgggaa ggcgagtatt ccaaggtgct 540
ggccattgct cagaactttg tgtgagttga gcccaggcct ctggttgcag gactcgtgaa 600
tggagcagtt ctgagaacca cccttttgct aagggagctt gggagccaca tggctgctcc 660
cttcacactg ggtaacagtg tagtatcctg tgagagaata aatgtattca tttatgtgtt 720
tttccagagc tttctgggat gtgggaaaat aaattacact gaagcagttg aaaggtggct 780
tacccgagtc tggccacacg ggtagcatt ctttacatgg agcagccttg gtgccagggt 840
ctgagccctt gcttttctgg tttggaccct ataagttcat ccaggactgt caggccctgg 900
aaaactgagg tacacaccaa atgccaattt ataaatgtac catggctcta accaaaa 957
```

FIG. 15

SEQ ID NO:11 ggagggaaga tggcggcgcc ctggtggcga gccgcgctgt gcgagtgtcg gagatggcgg 60
ggcttcagca cctcggccgt cctgggccgc cggacacccc cgctggggcc gatgcccaac 120
agtgacatcg acttgagcaa cctggagcgg ctggagaagt accggagctt cgaccgctac 180
cggcgccgag cagagcagga ggcgcaggcc ccgcactggt ggcggaccta ccgagagtat 240
ttcggggaga agacagatcc caaagagaag attgatattg ggctgcctcc acccaaagtc 300
tcccggaccc aacagctact ggaacggaaa caggccatcc aggagcttcg ggccaatgtg 360
gaagaggagc gggctgcccg cctccgcaca gccagtgtcc cgctggatgc cgtgcgggcc 420
gagtgggaga ggacctgtgg cccctaccac aagcagcgtc tggctgagta ttacggcctc 480
taccgagacc tgttccacgg tgccaccttt gtgccccgag tcccccctgca cgtggcctac 540
gctgtgggtg aggatgacct gatgcctgtg tactgtggca atgaggtgac tccaaccgag 600
gctgcccaag cgccagaggt gacctatgag gcagaagagg gctccttgtg gacgttgcta 660
ctcactagct tggatgggca cctgctggag ccagatgctg agtacctcca ctggctgcta 720
accaacatcc cgggtaaccg ggtggctgaa ggacaggtga cgtgtcccta cctccccccc 780
ttccctgccc gaggctccgg catccaccgt cttgccttcc tgctcttcaa gcaggaccag 840
ccgattgact tctctgagga cgcacgcccc tcaccctgct atcagctggc ccagcggacc 900
ttccgcactt ttgatttcta caagaaacac caagaaacca tgactccagc cggcttgtcc 960
ttcttccagt gccgctggga tgactccgtc acctacatct tccaccagct tctggacatg 1020
cgggagccgg tgtttgagtt cgtgcggccg ccccccttacc accccaagca gaagcgcttc 1080
ccccaccggc agcccctgcg ctacctggac cggtacaggg acagtcatga gcccacctat 1140
ggcatctact aaggagccag agtgtgcgca tttcagagca tgggattgat cggcagcaag 1200
agtaaagaca cagctccaga ggcccacact gtggggtctg ggccctgcct taggcagccc 1260
ccctctttgg ccccctcccg tcaggcccag ggcttggagt gaaagtgact ctcaggtggt 1320
ggggtgggga atgtgaataa acatgatttc ttgccggg 1358

FIG. 16

SEQ ID NO:12 agttatgcga aaacatggct gcggccggtt tggcccttct ttgtaggaga gtttcatccg 60
ccctgaaatc ttcccgatcg ttaataactc ctcaggtccc tgcctgcaca gggtttttc 120
ttagtttgtt gcctaagagt acaccaaatg tgacatcctt tcaccaatat agattacttc 180
ataccacatt gtcaaggaaa ggactagaag aatttttga tgacccaaaa aactgggggc 240
aagaaaaagt aaaatctgga gcagcatgga cctgtcagca actaaggaac aaaagtaatg 300
aagatttaca caaactttgg tatgtcttac tgaaagaaag aaacatgctt ctaaccctag 360
agcaggaggc caagcggcag agattgccaa tgccaagtcc agagcggtta gataaggtag 420
tagattccat ggatgcatta gataaagttg tccaggaaag agaagatgcc ctaaggcttc 480
ttcagactgg tcaagaaaga gctagacctg gtgcttggag aagagacatc tttggaagaa 540
tcatctggca caagttcaag cagtgggtta taccttggca cctaaataaa agatacaata 600
ggaaacgatt ctttgccttg ccttatgtgg accattttct cagactggaa cgtgagaaac 660
gagcccgcat caaagcacgg aaggaaaatt tagagagaaa gaaagcaaaa attcttttaa 720
aaaagtttcc acatcttgct gaagcccaaa agtcaagtct tgtctaagat gtctgaacta 780
ttaaatttac cattttgttt ttcttgaata gtctgtgtac aggagtaaat atgttaagtg 840
gtttataaag aaattctgtt tttagtcaag tgactttact aatcagttgt tctaagtgtg 900
aatatggcat gctaattagc taatttggta gaagctaatt tgcttctaaa aatcaggtat 960
aaagttcaga tgagattccc actttataaa ttctgacatt taagcaggct ttaaatgtca 1020
cctgctacct tagagtgtga aggtgatggt aactgccaca gcaaaggcaa taccgtagtt 1080
tttgaatttg aataatagtt ttacctctgt tgttaatagg ctatgaagag gatgtgggta 1140
ttgctgttaa taaacggagg actttgattc aaaataatga gaaatacatt tagtccttaa 1200
agtagtaatc acagtgcaca acagtccaaa atatatttct ggaatggcta atttttattt 1260
aattctgtaa gcctaaggta aaaagcatag gcagtaactt ttactagtca ataaaaagca 1320
gttctaccaa tccactggta attaatacac taaa 1354

FIG. 17A

SEQ ID NO:13 gggaccggca agatggcggc gcggacagcg ttcggtgctg tgtgccggcg cctctggcag 60
ggattgggga atttttctgt aaacacttct aagggcaata cagccaaaaa tggtggcttg 120
cttctcagta ccaatatgaa gtgggtacag ttttcaaacc tacacgttga tgttccaaag 180
gatttgacca aacctgtggt aacaatctct gatgaaccag acatattata taagcgcctc 240
tcggttttgg tgaaaggtca cgataaggct gtattggaca gttatgaata ttttgctgtg 300
cttgctgcta aagaacttgg tatctctatt aaagtacatg aacctccaag gaaaatagag 360
cgatttactc ttctccaatc agtgcatatt tacaagaagc acagagttca gtatgaaatg 420
agaacacttt acagatgttt agagttagaa catctaactg gaagcacagc agatgtctac 480
ttggaatata ttcagcgaaa cttacctgaa ggggttgcca tggaagtaac aaagacacaa 540
ttagaacagt taccagaaca catcaaggag ccaatctggg aaacactatc agaagaaaaa 600
gaagaaagca agtcataaag cctcagggag gccatttttg cctaaatttg aaatgagggt 660
gggccagatg agtatgttta agtggagagt gcttccagct gagatgattt gagtctgccc 720
taactgctcc attgagttct cgtgccctca tcagctgagg gcagggaatg gaactttaat 780
ggaagaacca cttttatcta ttctttttat tcattgtttc agttctgatt tcagcaaaca 840
tgagcaaacc actttgactg aaagcagaaa gagtgaaaat tctattttgt tacgctactg 900
gtgttcaatt attagtttgt accattttta atttatgtca gttgatgcat ctgaaaataa 960
gtgcttggag tgttcgtacc cttatttttt tttaagattc ctagaaggaa tctttggtta 1020
attcagattg agcagttaaa gtttttgcta tttacctttg tgcaggctgg catatgctaa 1080
tttgggggtg gtaaccaacc gattttatct catgtaagca ttacattttg aagactgaat 1140
atacttcaca gcagatcaaa cacatttatg gcatgcactg acctcttctt ggagcccaga 1200
actttataga gttgcctacc agggttactg taatggaatt tatgatctta agaaattact 1260
agttgtatta tttatcctat gattcattca ttcaataagc ttttactgca taaactttac 1320
atccagcact gtagttaagt acccaaaatt gaatagaaat aatggctttt gaaaatcgca 1380
caaagcaggc caggcacggt ggctcacgcc tgtaatccca gcattttggg aggccgaggc 1440
aggcggatca cgaggtcaag agatccagac catcctggct aacacggtga aaccccgtct 1500
ctaataaaaa tacaaaaatt agctggacat ggtggcacgt gcctgtaatc ccagctactc 1560
aggaggctga ggcaggagaa ttgcgtgaac ccgggcccgg tggaggctgc agtgagacga 1620
gatcgcgcca ctgcactcca gcctggcgac agagcgagac gccgtctcaa aaaaaaaaaa 1680

FIG. 17B agaaaattgt gcaaagcata ggtaaatatt tttctttatt aagcttctca ctgagaagcc 1740
ctctttattt tggtaaatgt cactctgttt gttaggagat gtctgctttt ccatgaaatg 1800
aaatagtggc taaagccctg aaagaggcaa gactacaatg ggctgaaaca gttggtatag 1860
caaccccaga gaagtgcttc attttctttt tatagtagaa gcaggtccat gtcttttgtg 1920
gtttcctgca catctttgga gtagttatga cttctcagtt tttccccccct taaactgcat 1980
tgcctattct tttttcctga catgctatca ggtatcagtg tgttgaatac atactgcttg 2040
tgtatcagac ttacgttact gtcatcacca ttaaaagaat tgcagctttg tgccccatga 2100

FIG. 18

SEQ ID NO:14 aggtttttga agatggcggc cctcaaggct ctggtgtccg gctgtgggcg gcttctccgt 60
gggctactag cgggcccggc agcgaccagc tggtctcggc ttccagctcg cgggttcagg 120
gaagtggtgg agacccaaga agggaagaca actataattg aaggccgtat cacagcgact 180
cccaaggaga gtccaaatcc tcctaacccc tctggccagt gccccatctg ccgttggaac 240
ctgaagcaca agtataacta tgacgatgtt ctgctgctta gccagttcat ccggcctcat 300
ggaggcatgc tgccccgaaa gatcacaggc ctatgccagg aagaacaccg caagatcgag 360
gagtgtgtga agatggccca ccgagcaggt ctattaccaa atcacaggcc tcggcttcct 420
gaaggagttg ttccgaagag caaaccccaa ctcaaccggt acctgacgcg ctgggctcct 480
ggctccgtca agcccatcta caaaaaaggc ccccgctgga acagggtgcg catgcccgtg 540
gggtcacccc ttctgaggga caatgtctgc tactcaagaa caccttggaa gctgtatcac 600
tgacagagag cagtgcttcc agagttcctc ctgcacctgt gctggggagt aggaggccca 660
ctcacaagcc cttggccaca actatactcc tgtcccaccc caccacgatg gcctggtccc 720
tccaacatgc atggacaggg gacagtggga ctaacttcag tacccttggc ctgcacagta 780
gcaatgctgg gagctagagg caggcagggc agttgggtcc cttgccagct gctatggggc 840
ttaggccatg ctcagtgctg gggacaggag ttttgcccaa cgcagtgtca taaactgggt 900
tcatgggctt acccattggg tgtgcgctca ctgcttggga agtgcagggg gtcctgggca 960
cattgccagc tgggtgctga gcattgagtc actgatctct tgtgatgggg ccaatgagtc 1020
aattgaattc atgggccaaa caggtcccat cctcttcatg acagctgtga gctccttact 1080
gtgggagagc tgcagggagc caaggtgggc tgcctgacac acttgccgct ctcgtgtgaa 1140
tccaagaaac tgcgttcctc aaa 1163

FIG. 19

SEQ ID NO:15 cccgcgctcc gcttggccca agatggcggc ctccgtgtgc agcgggttgc tggggccacg 60
ggtgctgtcc tggagccgag agctgccttg cgcttggcgc gccctgcaca cctccccggt 120
ctgcgccaag aaccgggcgg cccgagtacg cgtaagcaag gggacaagc cggtgaccta 180
cgaggaggca cacgcgccgc actacatcgc ccaccgtaaa ggctggctgt cgctgcacac 240
aggtaacctg gatggagagg accatgccgc agagcgaacg gtggaggatg ttttccttcg 300
caagttcatg tggggtacct tcccaggctg cctggctgac cagctggttt taaagcgccg 360
gggtaaccag ttggagatct gtgccgtggt cctgaggcag ttgtctccac acaagtacta 420
cttcctcgtg ggctacagtg aaactttgct gtcctacttt tacaaatgtc ctgtgcgact 480
ccacctccaa actgtgccct caaaggttgt gtataagtac ctctagaaca atcccctttt 540
ttccatcaag ctgtagcctg cagagaatgg aaacgtggga aaggaatggt atgtggggga 600
aatgcatccc ctcagaggac tgaggcatag tctctcatct gctattgaat aaagaccttc 660
tatcttg 667

FIG. 20

SEQ ID NO:16 acagctgccc gggactccag tgatcgccgc ggctcgctcg cgcccccggaa actgcccctt 60
ctcgggggtc atgatgggca gcaagatggc gtctgctagt agggtcgttc aggtagtcaa 120
accacacact ccattaataa ggtttcctga cagaagagac aatcctaaac ccaatgtatc 180
agaagctttg agatcagcag ggctaccatc tcactcttct gtaatttcac aacattctaa 240
aggaagtaaa tcaccagatt tgctgatgta tcagggtcca ccagacactg cagaaataat 300
aaaaacatta cctcagaaat acagaaggaa acttgtgtct caagaagaaa tggaatttat 360
ccaacgtgga ggtcctgaat aaccatggtg gctgctgttt gtcatcagac aatagaattg 420
tctttacaat aaaggacttc caaaatgaca gatgagaaac tgtatattaa acacctttaa 480
taaatattat gaaaaaaatg aaatatagaa aatttagatg gacacttgta tttcctaatt 540
tatgtatctt ggtcagcttc tccacaagct tacctaattg tttatatact ttatacttat 600
taaagtatac atttttaaat gttagcctat taatttactc ttgattatca aacattacca 660
gtgttgaact attaaaagca cacaatgtgt agtaaactat cataggattc ccataatttc 720
actttacttt ctgtttaggc atggaaaaat ttatcagtca gaattgctgt tttagggaca 780
tgattttcct gaaattgggt gaggatcagt gaaataatta ctctattact tgttcttaat 840
tctctgttct ctaatgtttt ttcattcaca agtttactgg agtataactg gcttagtaag 900
tatatcctac tctgaatgat aaaaatatag tcaagctaaa ataggtgact atactattaa 960
gatagagatc atacaaaaga ttccaaagaa agtcaaaaag tgtaaaatgg aaaataagag 1020
atcaaaatga atatagcata ggaataaaga tttcactaga aattgcaatt tattatgttt 1080
tggaggttgt aaggaagtct tgttttttgg tttattttac tgttttgtga tcttgtatgc 1140
aaatcctgat aaccattaac cttctcaaac ttaatgtctg agagcctcat aaaatcaaca 1200
tatttactta ttaagcagtt tatgaaactt taatggggcc cctcctgtgc caagggtacg 1260
tatattgtga agtaaagcct cacaaagcta aataaattct cttccatacc tttaa 1315

FIG. 21A

SEQ ID NO:17 gcggctcgga ctccagcatg gcgaccgcgg tgcgcgctgt gggctgcctc cccgtgctgt 60
gtagcgggac ggcaggtcat ttattgggga ggcagtgttc cctaaacacc ttaccagcag 120
cttccatttt ggcatggaag agtgttctcg gcaatggcca tttgtcatca ctgggaacca 180
gagacaccca tccctacgcc agcttgagcc gtgcactgca gacacaatgc tgtatttctt 240
ctcccagtca cctgatgagc cagcagtata gaccatatag tttcttcact aaattgactg 300
cagatgagct gtggaaaggc gctttagcag agactggtgc tggagcaaaa aaaggaagag 360
gcaaaagaac taaaaagaag aaaagaaagg atctgaacag gggtcagatc attggtgaag 420
ggcgttatgg ttttctatgg cccggactga atgtccctct tatgaaaaat ggagcagtgc 480
agaccattgc ccaaagaagc aaggaagagc aggagaaggt ggaggcagac atgatccagc 540
agagagaaga gtgggaccga aagaagaaga tgaaggttaa acgggagcga ggatggagtg 600
gaaactcatg gggaggcatc agtcttggcc cccctgaccc tggtccctgt ggagaaacat 660
atgaggattt tgataccagg atacttgagg taagaaacgt tttcactatg actgcgaaag 720
agggaagaaa gaaatcgatc cgtgtcttgg tggctgtggg gaacggaaaa ggagctgcag 780
gtttttctat tgggaaagct actgatcgga tggatgcttt caggaaagca aagaacagag 840
cagttcacca tttgcattat atagaacgat atgaagacca tacaatattc catgatattt 900
cattaagatt taaaaggacg catatcaaga tgaagaaaca acccaaaggt tacggcctcc 960
gctgccacag ggccatcatc accatctgcc ggctcattgg catcaaagac atgtatgcca 1020
aggtctctgg gtccattaat atgctcagcc tcacccaggg cctcttccgt gggctctcca 1080
gacaggaaac ccatcaacag ctggctgata agaagggcct ccatgttgtg gaaatccggg 1140
aggaatgtgg ccctctgccc attgtggttg cgtccccccg ggggcccttg aggaaggatc 1200
cagagccaga agatgaggtt ccagacgtca aactggactg ggaagatgtg aagactgcac 1260
agggaatgaa gcgctctgtg tggtctaatt tgaagagagc cgccacgtaa cctctctggc 1320
cttgtgcagc cagttcctgt gctgccctgc acctaggaga gactcagccc ctcacagctt 1380
gggatgttac cttgcctttt gtttgttttg agggaagttt aatctttaaa ctctttggaa 1440
ataaataatt atagctttca tttgttgagc acatgttata tgccaatgtg atagaacctt 1500
tacatacata tctcagttca agactacttt aaatattcat ccaaagtaac aaaagtaaat 1560
gaattaggga gacggggtta ataatttgac ccaatcagta ataatgtaca caatgataat 1620
tgctgtagta attatagcta atatatatga actcattcat ccaaagtgaa tgtgattaac 1680

FIG. 21B ttcattttac agagcagtta agtaacttga ctaccgtgag gaacttccaa accgttttcc 1740
acagtggaaa tggaagttgt aggctactat tgggaatgtt aaatggtata ttaattgtat 1800
accattgcaa ttttgacttg tatttccctg atggctgatg atgttgaaca tcttttcatg 1860
tgctgattgg ccatttgtat atgtttttg gagaaatgtc tattcagagc ctttgcccat 1920
ttaaaaagtt attttttatt attattgagt tccttatagt ttctagatat aagcccccct 1980
atcatacatg ctttacagaa gtttttaccc attctgtgga atatatatat ttttatttct 2040
ttgcatactc tttctgcccc acccacatcc tctttctggg acactgatga ccaaaatgtt 2100
gaatctttta ctattgtccc gtgagtccct gaggcgctgt ttattttttt tccagtctgt 2160
tttctctgtg ttgctcagtt taggtaattt ctattgtttt atcttcagaa taactggtta 2220
tttactcttt cctttccatt ctgctcttga accatccatg cagtacttta actttgactg 2280
tcattgtata tttcagttaa aatttccatt tggtttattt tttatgtctt ctctttattt 2340
gctgaggcta tttgctgaga cttttttttt ctttaaatgg cttcaagagt gtttataatt 2400
gctcactgaa gcatttttat ggtggctgct ttaaaatctt tgtcatcagg taggtgtggt 2460
ggctcacgcc tataacccca gcactttgtg aaggtgaggc aggaggattg cttcagccca 2520
ggagtttgag atcagcctag gcaacaaagt gagacctcat ctctacaaaa agtaaaagta 2580
aatttaaaag ttagacacac atggtggtgt atgcctgtag tcccagctac ataggaggct 2640
gaagtgggag gatcatttga ttgcaggagg ttgaggctgc agtgagcctt gttcatgcca 2700
ctccagcctg ggtggcagag tgagaccttg tctccaaaaa aaaaaaaaaa attgtcataa 2760
agtttcaaca tctgtgtcat cttagtgttg acatcccttg aggtttttc tcattcaagt 2820
ttacaatgtc ctagttcttg ttatgatgag tgactttggc tgtatcctgg tcatcttcac 2880
tgttatgaag ctctgggagt tatttaaatc tctcagcatg cttcctctga cggtgctggt 2940
atgggatggg gcactgcctc gttactgcct ggtgaggatg gagatccagg tttcctcctg 3000
tcgctgtcct cgggacctct gctgaggcct ttctgctgga agtaggagga gcaccctaat 3060
ggcaccgtgg gatagggagc aggccatgtt aggctggatg gtgaaagttt tcagcctgtg 3120
acgttgtctg gtgtgggtgg gtcccctttt tttgtgtgtg gtattttgct agagtaaggt 3180
agttatttcc taaaacttat ctgtcctgtt agttttcctt cttaagtacc taacaaatat 3240
aaagacaatg aactttaagc aataaaagac aatgatcctt tggagagggg aaacaaaa 3298

FIG. 22

SEQ ID NO:18 actggactcc cgtgagctgg aaggaacaga tttaatatct aggggctggg tatccccaca 60
tcactcattt ggggggtcaa gggacccggg caatatagta ttctgctcag tgtctggaga 120
tcatctaccc aggctggggc ttctgggaca ggcgaggacc cacggaccct ggaagagctg 180
gtccagggga ctgaactccc ggcatcttta cagagcagag catgatcaca ttcctgccgc 240
tgctgctggg gctcagcctg ggctgcacag gagcaggtgg cttcgtggcc catgtggaaa 300
gcacctgtct gttggatgat gctgggactc caaaggattt cacatactgc atctccttca 360
acaaggatct gctgacctgc tgggatccag aggagaataa gatggcccct tgcgaatttg 420
gggtgctgaa tagcttggcg aatgtcctct cacagcacct caaccaaaaa gacaccctga 480
tgcagcgctt gcgcaatggg cttcagaatt gtgccacaca cacccagccc ttctggggat 540
cactgaccaa caggacacgg ccaccatctg tgcaagtagc caaaaccact ccttttaaca 600
cgagggagcc tgtgatgctg gcctgctatg tgtggggctt ctatccagca gaagtgacta 660
tcacgtggag gaagaacggg aagcttgtca tgcctcacag cagtgcgcac aagactgccc 720
agcccaatgg agactggaca taccagaccc tctcccattt agccttaacc ccctcttacg 780
gggacactta cacctgtgtg gtagagcaca ctggggctcc tgagcccatc cttcgggact 840
ggacacctgg gctgtccccc atgcagaccc tgaaggtttc tgtgtctgca gtgactctgg 900
gcctgggcct catcatcttc tctcttggtg tgatcagctg gcggagagct ggccactcta 960
gttacactcc tcttcctggg tccaattatt cagaaggatg gcacatttcc tagaggcaga 1020
atcctacaac ttccactcca agtgagaagg agattcaaac tcaatgatgc taccatgcct 1080
ctccaacatc ttcaaccccc tgacattatc ttggatccta tggtttctcc atccaattct 1140
ttgaatttcc cagtctcccc tatgtaaaac ttagcaactt gggggacctc attcctggga 1200
ctatgctgta accaaattat tgtccaaggc tatatttctg ggatgaatat aatctgagga 1260
agggagttaa agaccctcct ggggctctca gtgtgccata gaggacagca actggtgatt 1320
gtttcagaga aataaacttt ggtggaaa 1348

FIG. 23A

SEQ ID NO:19 gttcctgtcc tcaccacacg gactgagact gatttgatta aagcaccaga gtgtaatggc 60
cctcagagca gggctggtcc tggggttcca caccctgatg accctcctga gcccgcagga 120
ggcaggggcc accaaggctg accacatggg ctcctacgga cccgccttct accagtctta 180
cggcgcctcg ggccagttca cccatgaatt tgatgaggaa cagctgttct ctgtggacct 240
gaagaaaagc gaggccgtgt ggcgtctgcc tgagtttggt gactttgccc gctttgaccc 300
gcagggcggg ctggccggca tcgccgcaat caaagcccat ctggacatcc tggtggagcg 360
ctccaaccgc agcagagcca tcaacgtgcc tccacgggtg accgtgctcc ccaagtctcg 420
ggtggagctg ggccagccca acatcctcat ctgcatcgtg gacaacatct tcccccctgt 480
gatcaatatc acctggctgc gcaacggcca aactgtcact gaggggagtgg cccagaccag 540
cttctattcc cagcctgacc atttgttccg caagttccac tacctgccct tcgtgccctc 600
agccgaggac gtctatgact gccaggtgga gcactggggc ctggatgcgc cactcctcag 660
gcattgggag ctccaggtgc ctattccacc accagatgcc atggagaccc tggtctgtgc 720
cctgggcctg gccatcggcc tggtgggctt cctcgtgggc accgtcctca tcatcatggg 780
cacatatgtg tccagtgtcc ccaggtaatg atccttctga gagaaatgac ttgtgggaga 840
caccctgcag atcctcatgg gtttgtgaca gcccctgcgt gctcagtgcc ctttaagtgc 900
atcccgctgt gctgactttg agtgggatca acatctgtcc tacgggtccc ctctttttg 960
gccccagtat tcatggcagg gtttgttgga cacctactag cttcccttcc cattcaacac 1020
acacacacat tcttgctcta cccaaagctc tggctggcag cactaaatgc tttggtggtg 1080
tttgcactgt gtcctttcca ggccttggcc agttcttcca ggggtgaggc atgtggtgct 1140
ggggattggc agccatcctg gggcccacac aggtgtgtct tgctccattt ggcccattgt 1200
gtgttacttt gtgaatgagc catttcacat ggacttcatg aaatttgcct cctgagttca 1260
ggtttaccct gaaagggatg cagattatcc tgttcctcac gaccccctca gctaacaaca 1320
gttctgaagg gtgctgggac aggacaggct catggggact ccactcctgc ctgggtttac 1380
tctgtatgaa gaggccactg gtatcctgcc atgatgttat ctcctttttc tacttttccc 1440
tagagtccca tgcatgataa agagaggccc aaggcttgga taaggtggcc acttccctca 1500
gtggagtcag tcatgttagg taggaggtgg tagagtcggt ctgcgaggta tctcgtaaga 1560
ggggaggtcc acctagacac actctaaata tgtggcctag aagattttgg tctacttttc 1620
tgtgaacaga atttaaaaca tacaaagaga taaatcacca taccacatag tttatgtcag 1680

FIG. 23B gaccaaaatg agcaatacag attacggttt tcaaaccaga atgcacataa gaactgcttg 1740
ggatcctttt aaaagtacag gcattggcct ggtgcagtgg ctcattcctg taatcccagc 1800
actttgggag gccaagggga caggactgct tgaggccaag aggtggaaac catcttgggc 1860
tacatagaga gaccccatct ctacaaagaa agatttaaaa attaaccagg catggtggct 1920
cgcacctgta ttcccagcca ctggggaggc tgaggccgga ggagtgcttg agcccaggag 1980
ttcaaggctg cagtgagcca agattgcgcc actgcactcc agcctaggtg acagagtgag 2040
accctgtctc taaataaata aataaataaa atataaaaat aacagtcatc acccagacct 2100
actgaattag aatctcggga gtgcaggggg cagcaacagg gaggctgtct tttctgagat 2160
ggggtctcac tctgtcacca ggctggagtg ccatggcatg atctcagctc actgcaacct 2220
ccacctcctg agttcaagcc attctcctgc ctcagcctcc tgagtagctg ggactacagg 2280
tgtgcgccac tacactcagc taatttttgt attttaagta gagacggggt ttcatcatgt 2340
tggccaggat ggcctccatc tcttgacctc gtgatccacc caccttccct cccaaagtac 2400
tggaattaca ggcattagcc actgtgccca gccgaggctg tcatttttaa ccggctctgg 2460
atgactctga tgcagccatc ctggaccttg gctgtggtct ggtaactgga acccagtgac 2520
gtaatcaggt gccatcgggg gtcatgggaa agggggatcc ccaaggtctg aggtggacta 2580
ggaaggcttt ctgaagaacc tgggtctgtt agggcatcag ccaatcaagg tacaagtaaa 2640
tagaggcaaa atgagggttt gaactgtgag cagttggtcc tggaaaagaa agaaaccaag 2700
agattatggg gactcaatgg gcttcttaag agagaataag ttgaaatcaa tgaccagaag 2760
accctgatgg aagtggagga gaatcatctc aggcaaactt tttgtgtgcc agtaacagaa 2820
accctctttg tgtgatcaca tgcaaagtat aggatatttg caatatagcc atggggagga 2880
gtgcagggcc caagggtaga ttttagccag gcctcccagg aacagaactc ggatccgaaa 2940
agcccagaga agctagagct gcccctccaa cactctcgga tccacatggt ctgtgttctc 3000
tagacccccc tgcatgttag cggtgttctc tctctgtgga ctgactgtcc ttctcagtga 3060
acatgtccac ccgacagctc ctgagtttat atcatctcaa ccctcacaac ccacagaggc 3120
tgtgtctcct agtcacagct ttaaattact ggaaaaataa atgactggcc aaacttggag 3180
caggtgtcca tcccagccct gtgtagttag agcaggaatc aagatctcaa cacaaatgtg 3240
gctgccaagc actcagcccc ggggcgaggg gtcaagttct tctcagagaa agaggaataa 3300
gttggttctc agaagacatc acaagatacg tgtgtaccca acaatctctg atctctgctg 3360
atcttttgct tagacgttaa cttgatgcat cattggaaag gtgtttctct catctctgtc 3420
ctaaggcttg ataaagtcat taaaattgtg ttcttttgac taaa 3464

FIG. 24A

SEQ ID NO:20 ccttcttttc ctgactgcag ctcttttcat tttgccatcc ttttccagct ccatgatggt 60
tctgcaggtt tctgcggccc cccggacagt ggctctgacg gcgttactga tggtgctgct 120
cacatctgtg gtccagggca gggccactcc agagaattac cttttccagg gacggcagga 180
atgctacgcg tttaatggga cacagcgctt cctggagaga tacatctaca accgggagga 240
gttcgcgcgc ttcgacagcg acgtgggggga gttccgggcg gtgacggagc tggggcggcc 300
tgctgcggag tactggaaca gccagaagga catcctggag gagaagcggg cagtgccgga 360
caggatgtgc agacacaact acgagctggg cgggcccatg accctgcagc gccgagtcca 420
gcctagggtg aatgtttccc cctccaagaa ggggcccttg cagcaccaca acctgcttgt 480
ctgccacgtg acggatttct acccaggcag cattcaagtc cgatggttcc tgaatggaca 540
ggaggaaaca gctggggtcg tgtccaccaa cctgatccgt aatggagact ggaccttcca 600
gatcctggtg atgctggaaa tgaccccccca gcagggagat gtctacacct gccaagtgga 660
gcacaccagc ctggatagtc ctgtcaccgt ggagtggaag gcacagtctg attctgcccg 720
gagtaagaca ttgacgggag ctgggggctt cgtgctgggg ctcatcatct gtggagtggg 780
catcttcatg cacaggagga gcaagaaagt tcaacgagga tctgcataaa cagggttcct 840
gagctcactg aaaagactat tgtgccttag gaaaagcatt tgctgtgttt cgttagcatc 900
tggctccagg acagaccttc aacttccaaa ttggatactg ctgccaagaa gttgctctga 960
agtcagtttc tatcattctg ctctttgatt caaagcactg tttctctcac tgggcctcca 1020
accatgttcc cttcttctta gcaccacaaa taatcaaaac ccaacatgac tgtttgtttt 1080
cctttaaaaa tatgcaccaa atcatctctc atcacttttc tctgagggtt ttagtagaca 1140
gtaggagtta ataaagaagt tcattttggt ttaaacatag gaaagaagag aaccatgaaa 1200
atggggatat gttaactatt gtataatggg gcctgttaca catgacactc ttctgaattg 1260
actgtatttc agtgagctgc ccccaaatca agtttagtgc cctcatccat ttatgtctca 1320
gaccactatt cttaactatt caatggtgag cagactgcaa atctgcctga taggacccat 1380
attcccacag cactaattca acatatacct tactgagagc atgttttatc attaccatta 1440
agaagttaaa tgaacatcag aatttaaaat cataaatata atctaataca ctttaaccat 1500
tttctttgtg tgccatcaca aatactcctt aaccaaatac ggcttggact tttgaatgca 1560
tccaatagac gtcatttgtc gtctaagtct gcattcatcc accagcctag gcctcctgtc 1620
ttaattttca tacagacaga aatgactccc cactggggaa agagcaaagc aatacatgta 1680

FIG. 24B gcactctttt tcaaacactg gtcttttttt ttttcttaac aatccaacat tgttatgtgt 1740
tttgcgtctc atattgacac cttttggtca aggtagagga catgtttgtt gtaagctttc 1800
tttttcgtgt agaggatgga ttcttcactc ctgatacaca caatcagtgc acagcagctc 1860
tcttatacat ccagttgatg ccttcagtct ccctggcttc ttacaagcat cttctgggcc 1920
ttgtgtgtcc ctgggcacct gtccctggtc aattcccgaa agctactgtg ctcctcttgc 1980
ccatctcccc ttgcaaataa tatcttccat cgggggaccg gcttcctcca atttcaggag 2040
aggtggggct gaaggcacag acttgggcgt cactggcaca gatataagta aatacagctg 2100
gagtctgcag agaggctgga ctgagtcagg gagtcaggaa agagaagcca cacacaagga 2160
caaccaatca tgtttctcat aatcttctta acctagggaa taggacacaa tcattttttc 2220
tttttaaaac atctttatcc ctgatcagcc tcatttcctc aaaaactata aaggaaaatg 2280
ctgctgactt gtttttgcgt agtaatttca gctgtcacat aataagctaa ggaagacagt 2340
atatagtaaa taaggaccct ttatctgtct tattttccct tttggcttca caggaaactt 2400
gtgagaaacc tatgcagcat aaaattaata tgatttcaat ccagggattc aacgatggaa 2460
ggaggtcatg agaatagcag aaagtcttca aatcgagatc attatgaaat cctcagaccc 2520
agagcacata aatcctaccc tcagagtcac tgagcagtta acattacaaa ttacaaacca 2580
tatccagtca gagtcattct ctttcctgct tgtctcctgt actcatgtta caggttaggg 2640
cagtaccccg agtggagtga acaatctctg gactaacact tgtcaggatc agaagctgag 2700
gtatctgcac ccacattaca ggaacaggat atgtgctcct agggaactga gggtgtcagg 2760
agatgaggaa tgtccctgga gtcacagaaa gaaggtatca gatgtgtctc actctgacat 2820
atgcaggtgt ttatgaaact ctgggatttc taaggaagga tgcagtgcag agacaggtcc 2880
cagaggagac aagagctgag agaccatcca aactgggacc accttgtcac tagacttcaa 2940
attttcaata ttgatagagt gttttctaag agtcaggccc tttgctgagt gctatgtgca 3000
gcaggatcaa aggcagccag gaggtagagg agtcttgagg tacatcagtc attggagttg 3060
aagagcagag attcaaagga aagttggaac tggagcttta aaggagatgt gaagtgggtg 3120
actcaacctc tgactcagaa aaattgatac ctgcagaaga aaaaaacccgg cgggcttagg 3180
actcccagct gagtgttgta tcctccatcc ctttccacct ggtcccttca ttttctaccc 3240
ctcacagttc cctaacgaga aggtggtcca cccaacagac aacactgcct cagatggtta 3300
tcaaggggta ccctaagaag aaatcatctc accctctctt tgtccccatt tgtcaagtag 3360
cagtgaggcc gagccagggg atggtgaaag tggaaggagg tgggagttgg gcatcgggtg 3420
tgaagatgct cttgaaaggg gttttaataa ccacttgcta ccaggccagt gaacacttac 3480
catagttgat gccttttgag catgttgcat tgtaaactgt ccctgaaatt actgtgcact 3540

FIG. 24C tggcttatgg gatgaaacat cctcctagtt cttttgtctc tcagcttctc tgaagtctca 3600
ttgagcacct tctcttcaat ttcttttaca cagtaagaat aggatcagct gtgctaaact 3660
aacaaatacc cagatatcca ggtttggctc atgttacacg tccaaagtaa gtcatgcagg 3720
aagctctgct catcatcgta ctcaggaagt caggctgaca gtctttctcc tgcacatctg 3780
ctcccagaac ctcccccagca gaatgaaggg aacctaagaa tttattcact ggcttttaat 3840
gatccctcct agaaagaaca cacttctcgc atttcatttt ccaatgtaaa tcatatggct 3900
gcaactaact tcaaataagt gggaatactt gaaggtggaa aacatttaag aagtacacac 3960
taaataaata ataaaatact tctacaagag a 3991

FIG. 25

SEQ ID NO:21

```
acaattgctc tacagctcag agcagcaact gctgaggctg ccttgggaag aagatgatcc 60
taaacaaagc tctgctgctg ggggccctcg ccctgactgc cgtgatgagc ccctgtggag 120
gtgaagacat tgtggctgac catgttgcct cctatggtgt gaacttctac cagtctcacg 180
gtccctctgg ccagtacacc catgaatttg atggagacga ggagttctat gtggacctgg 240
agacgaaaga gactgtctgg cagttgccta tgtttagcaa atttataagt tttgacccgc 300
agagtgcact gagaaatatg gctgtgggaa aacacacctt ggaattcatg atgagacagt 360
ccaactctac cgctgccacc aatgaggttc ctgaggtcac agtgttttcc aagtttcctg 420
tgacgctggg tcagcccaac accctcatct gtcttgtgga caacatcttt cctcctgtgg 480
tcaacatcac ctggctgagc aatgggcact cagtcacaga aggtgtttct gagaccagct 540
tcctctccaa gagtgatcat tccttcttca agatcagtta cctcaccttc ctcccttctg 600
ctgatgagat ttatgactgc aaggtggagc actggggcct ggacgagcct cttctgaaac 660
actgggagcc tgagattcca gcccctatgt cagagctcac agagactttg gtctgcgccc 720
tggggttgtc tgtgggcctc atgggcattg tggtgggcac tgtcttcatc atccaaggcc 780
tgcgttcagt tggtgcttcc agacaccaag ggctcttatg aatcccatcc tgaaaaggaa 840
ggtgcatcac catctacagg agaagaagaa tggacttgct aaatgaccta gcactattct 900
ctggcctgat ttatcatatc ccttttctcc tccaaatgtt tcttctctca cctcttctct 960
gggacttaag gtgctatatt ccctcagagc tcacaaatgc ctttcaattc tttccctgac 1020
ctcctttcct gaattttttt attttctcaa atgttaccta ctaagggatg cctgggtaag 1080
ccactcagct acctaattcc tcaatgacct ttatctaaaa tctccatgga agcaataaat 1140
tccctttga tgcctctatt gaatttttcc catctttcat ctcagggctg actgagagca 1200
taacttagaa tgggcgactc ttatgtttta ggccaatttc atatcattcc ccagatcata 1260
tttcaagtcc agtaacacag gagcaaccaa gtacagtgta tcctgataat ttgttgattt 1320
cttaactggt gttaatattt ctttcttcct tttgttccta cccttggcca ctgccagcca 1380
cccctcaatt caggtaccaa cgaaccctct gcccttggct cagaatggtt atagcagaaa 1440
tacaaaaaaa aaaaaaaa 1458
```

FIG. 26

SEQ ID NO:22 attaggtttg agctgtgttg actaccactg ctttttcctt ggtctcactt acgtcttgga 60
agatggctct gcagatccct ggaggctttt gggcagcagc tgtgaccgtg atgctggtga 120
tgctgagcac cccagtggct gaggccagag actttcccaa ggatttcttg gtccagttta 180
agggcatgtg ctacttcacc aacgggacag agcgcgtgcg cggtgtggcc agatacatct 240
ataaccgcga ggagtacggg cgcttcgaca gcgacgttgg ggagttccag gcggtgaccg 300
agctggggcg gagcatcgag gactggaaca actataagga cttcttggag caggagcggg 360
ccgcggtgga caaggtgtgc agacacaact acgaggcgga gctgcgcacg accttgcagc 420
ggcaagtgga gcccacagtg accatctccc catccaggac agaggccctc aaccaccaca 480
acctgctggt ctgctcggtg acagatttct atccagccca gatcaaagtc cggtggtttc 540
ggaatgacca ggaggagaca gccggtgttg tgtccacctc cctcattagg aatggtgact 600
ggaccttcca gattctggtg atgctggaaa taactcccca gcgtggagac atctacacct 660
gccaagtgga gcaccccagc ctccagagcc ccatcaccgt ggagtggcgg gctcagtctg 720
aatctgccca gagcaagatg ctgagtggca ttggaggctt cgtgctgggg ctgatcttcc 780
tcgggctggg ccttatcatc cgtcacaggg gtcagaaagg acctcgaggg cctccaccag 840
caggactcct gcactgactc ctgaggactt ttgtctggga ttggtcatca ctcttctgta 900
atgcccacct gcccctgccc agaattccta gctgcctgtg tcaccctgtc ccactgaggt 960
cagagtccta cagtggctca tgcagccaca ggtcaccttc tgtgatcccc atcccaaggc 1020
actggtggtg actctgcttc ctgcactgac ccagagcctc tgcctgtgca ctgcaagctg 1080
tgtctactca ggccccaagg ggcatctctg tttccattct ccccccacag acctgtcaag 1140
agaagcatga caaacaaaat catttacctg actttagtgc tttttcccat aattaaacct 1200
gattctgagt ta 1212

FIG. 27

SEQ ID NO:23

```
attcttgtct gttctgcctc actcccgagc tctactgact cccaacagag cgcccaagaa      60
gaaaatggcc ataagtggag tccctgtgct aggatttttc atcatagctg tgctgatgag     120
cgctcaggaa tcatgggcta tcaaagaaga acatgtgatc atccaggccg agttctatct     180
gaatcctgac caatcaggcg agtttatgtt tgactttgat ggtgatgaga ttttccatgt     240
ggatatggca aagaaggaga cggtctggcg gcttgaagaa tttggacgat ttgccagctt     300
tgaggctcaa ggtgcattgg ccaacatagc tgtggacaaa gccaacctgg aaatcatgac     360
aaagcgctcc aactatactc cgatcaccaa tgtacctcca gaggtaactg tgctcacaaa     420
cagccctgtg gaactgagag agcccaacgt cctcatctgt ttcatagaca agttcacccc     480
accagtggtc aatgtcacgt ggcttcgaaa tggaaaacct gtcaccacag gagtgtcaga     540
gacagtcttc ctgcccaggg aagaccacct tttccgcaag ttccactatc tcccctttcct    600
gccctcaact gaggacgttt acgactgcag ggtggagcac tggggcttgg atgagcctct     660
tctcaagcac tgggagtttg atgctccaag ccctctccca gagactacag agaacgtggt     720
gtgtgccctg ggcctgactg tgggtctggt gggcatcatt attgggacca tcttcatcat     780
caagggattg cgcaaaagca atgcagcaga acgcaggggg cctctgtaag gcacatggag     840
gtgatggtgt ttcttagaga gaagatcact gaagaaactt ctgctttaat ggctttacaa     900
agctggcaat attacaatcc ttgacctcag tgaaagcagt catcttcagc attttccagc     960
cctatagcca ccccaagtgt ggatatgcct cttcgattgc tccgtactct aacatctagc    1020
tggcttccct gtctattgcc ttttcctgta tctattttcc tctatttcct atcattttat    1080
tatcaccatg caatgcctct ggaataaaac atacaggagt ctgtctctgc tatggaatgc    1140
cccatggggc atctcttgtg tacttattgt ttaaggtttc ctcaaactgt gatttttctg    1200
aacacaataa actattttga tgatcttggg tggaa                               1235
```

DIAGNOSTIC TOOLS AND TREATMENTS FOR CLEAR CELL RENAL CELL CARCINOMA

CROSS REFERENCE TO RELATED APPLICATIONS

This application claims priority to U.S. Provisional Application Ser. No. 63/110,042, filed Nov. 5, 2020, which application is hereby incorporated by reference in its entirety.

STATEMENT REGARDING FEDERALLY FUNDED RESEARCH OR DEVELOPMENT

This invention was made with government support under contract no. GM128216, CA117846, ES006096 and 2KL2TR001426 awarded by the National Institutes of Health, contract no. W81XWH-15-1-0347 awarded by United States Army Medical Research and Material Command and Biomedical Laboratory Research and Development grant 2I01BX001110 from Veteran Administration. The government has certain rights in the invention.

TECHNICAL FIELD

The present invention relates to methods of treating cancer. More specifically, it relates to methods of diagnosing and treating the recurrence of clear cell renal cell carcinoma.

BACKGROUND OF THE INVENTION

Clear cell renal cell carcinoma (ccRCC) is the most common type of kidney cancer. Tobacco smoking, hypertension, and obesity have been identified as risk factors for RCC and the cancer is more common in men as compared to women. While the management of metastatic RCC has undergone a paradigm shift over the last two decades with the advent of targeted therapies and immune checkpoint inhibitors (ICIs), the same is not true for patients with localized RCC. Management of patients with localized or locally advanced RCC involves surgical resection by partial or radical nephrectomy. However, 20-40% of all localized kidney cancer patients experience a recurrence and those with high risk disease have a ~50% risk of recurrence after surgical resection within six years. Several systemic therapies, including cytokines and vascular endothelial growth factor (VEGF) tyrosine kinase inhibitors (TKIs) that showed efficacy in metastatic RCC (mRCC), have not shown encouraging results in the adjuvant setting. Sunitinib, a VEGF TKI is the only drug approved per National Comprehensive Cancer Network (NCCN) following nephrectomy based on the S-TRAC trial, where the drug demonstrated an improvement in disease free survival (DFS). Other TKIs evaluated in the adjuvant setting (sorafenib, pazopanib and axitinib) did not improve survival. Due to inconsistent results and serious adverse effects related to sunitinib, it is often not used in clinic. More recently, immune checkpoint inhibitors (ICIs) demonstrated efficacy in metastatic RCC with an improved safety profile and are now being tested in several active clinical trials in the neoadjuvant and adjuvant setting.

There is a lack of validated biomarkers to predict risk of recurrence in localized ccRCC after surgical resection. Risk of recurrence for localized ccRCC is currently based on pathology data derived from surgical specimens (such as tumor stage, size of the tumor, nuclear grade and necrosis) and patient characteristics such as baseline performance status. Two validated models that are used include the University of California-Los Angeles Integrated Staging System (UISS) and the Stage, Size, Grade and Necrosis score (SSIGN). The use of these models is however not rampant due to variable results in clinical trials. Several studies identified tumor and stromal signatures in localized ccRCC These signatures include the 34-gene signature which classifies ccRCC into ccA (good risk) and ccB (poor risk) subtypes, and a 16-gene assay which helps calculate a recurrence score to predict recurrence after surgery. However, these signatures have not been incorporated in clinical trials and hence do not carry prospective validation. Signatures from metastatic ccRCC clinical trials such as the angiogenic and the T-effector or immunogenic signatures, have not been evaluated in localized RCC yet. There are currently no validated biomarkers to prognosticate or predict choice of treatment for localized ccRCC patients undergoing surgery and this remains an unmet need for patients with localized RCC.

SUMMARY OF THE INVENTION

The present invention addresses this need by providing a method of diagnosing the likelihood of recurrence of clear cell renal cell carcinoma in a subject. The method involves a) detecting the gene expression signatures of mitochondrial electron transport chain subunits, mitochondrial ribosomal proteins, major histocompatibility complex class II (MHC-II) proteins or combinations thereof in a kidney tumor tissue sample or kidney tumor biopsy from the subject; and b) determining that the subject has an elevated risk of recurrence of clear cell renal cell carcinoma if the gene expression signatures include certain sequences. In one embodiment, these include at least one gene expression signature selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8; at least one gene expression signature selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17; and at least one gene expression signature selected from the group consisting of SEQ ID NO:18, SEQ ID NO:19, SEQ ID NO:20, SEQ ID NO:21, SEQ ID NO:22 and SEQ ID NO:23.

In one embodiment, the gene expression signatures are detected using quantitative RT-PCR or comparable methods of estimating the abundance of mRNA molecules in a sample.

In another embodiment, the method of the present invention also includes the step of providing personalized therapy to the subject if an elevated risk of recurrence of clear cell renal cell carcinoma is determined. In one embodiment, the therapy involves administering a therapeutically effective amount of mitochondrial respiratory complex inhibitors, angiogenic inhibitors, inhibitors of the mTOR pathway, immune checkpoint inhibitors, mitoriboscins, inhibitors of mitoribosomes or combinations thereof to the subject. In another embodiment, the therapy involves administering a therapeutically effective amount of biguanides, metformin, phenformin, BAY-872243, IACS-010759, dihydroorotate dehydrogenase inhibitors, such as leflunomide, brequuinar, teriflunomide or combinations thereof to the subject. In another embodiment the therapy involves administering a therapeutically effective amount of copper chelators, such as D-penicillamine:(S)-2-amino-3-mercapto-3-methylbutanoic acid (DPA), Tetrathiomolybdate (TM), Trientine: triethylenetetramine dihydrochloride (TETA), 5,7-Dichloro-2[(dimethylamino) methyl]quinolin-8-ol (PBT2), 2,3-Dimercaptosuccinic acid (DMSA).

In one embodiment, it is determined that the subject has an elevated risk of recurrence of clear cell renal cell carcinoma if the gene expression signatures include certain sequences. In one embodiment, these include: at least two gene expression signatures selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8; at least two gene expression signatures selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17; and at least two gene expression signatures selected from the group consisting of SEQ ID NO:18, SEQ ID NO:19, SEQ ID NO:20, SEQ ID NO:21, SEQ ID NO:22 and SEQ ID NO:23.

In another embodiment, it is determined that the subject has an elevated risk of recurrence of clear cell renal cell carcinoma if the gene expression signatures include at least the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23.

Another embodiment of the present invention is a method of diagnosing the likelihood of recurrence of clear cell renal cell carcinoma in a subject. It involves detecting and quantifying total copper content and Cu-COX complex in a sample of kidney tumor tissue or kidney tumor biopsy from the subject. It is determined that the subject has an elevated risk of recurrence of clear cell renal cell carcinoma if a) the level of Cu-COX complex identified is higher than 0.45 ng $g^{-1}$ expressed as copper concentration or b) the copper content at a molecular mass fraction between 500 kDa-250 kDa is ≥20% of the total copper in the sample. In one embodiment, the method further includes detecting and quantifying the total copper in a kidney tumor tissue sample or kidney tumor biopsy from the subject and determining that the subject has an elevated risk of recurrence of clear cell renal cell carcinoma if the level of total copper identified is higher than 4.5 ng $g^{-1}$ expressed as total copper concentration. In another embodiment, the Cu-COX complex is detected using SEC-UV-Vis-ICP-MS. In one embodiment, other comparable methods of copper detection are used.

In another embodiment, the method of the present invention also includes the step of providing personalized therapy to the subject if an elevated risk of recurrence of clear cell renal cell carcinoma is determined. In one embodiment, the therapy involves administering a therapeutically effective amount of mitochondrial respiratory complex inhibitors, angiogenic inhibitors, inhibitors of the mTOR pathway, immune checkpoint inhibitors, mitoriboscins, inhibitors of mitoribosomes or combinations thereof to the subject. In another embodiment, the therapy involves administering a therapeutically effective amount of biguanides, metformin, phenformin, BAY-872243, IACS-010759, dihydroorotate dehydrogenase inhibitors, such as leflunomide, brequuinar, teriflunomide or combinations thereof to the subject. In another embodiment the therapy involves administering a therapeutically effective amount of copper chelators, such as D-penicillamine:(S)-2-amino-3-mercapto-3-methylbutanoic acid (DPA), Tetrathiomolybdate (TM), Trientine: triethylenetetramine dihydrochloride (TETA), 5,7-Dichloro-2[(dimethylamino) methyl]quinolin-8-ol (PBT2), 2,3-Dimercaptosuccinic acid (DMSA).

In another embodiment, detection of copper levels according to the present invention is used as a predictive biomarker for treatment of ccRCC from tobacco smoking patients. If indicated treatments for such patients include the therapies described in the paragraph above.

Another embodiment of the present invention is a method of diagnosing the likelihood of recurrence of clear cell renal cell carcinoma in a subject. The method involves a) detecting the gene expression signatures of mitochondrial electron transport chain subunits, mitochondrial ribosomal proteins, major histocompatibility complex class II (MHC-II) proteins or combinations thereof in a kidney tumor tissue sample or kidney tumor biopsy from the subject; b) detecting and quantifying Cu-COX complex in a kidney tumor tissue sample or kidney tumor biopsy from the subject; and c) determining that the subject has an elevated risk of recurrence of clear cell renal cell carcinoma if the level of Cu-COX complex identified is higher than 0.45 ng $g^{-1}$ expressed as copper concentration and if the gene expression signatures include certain sequences. In one embodiment, these include at least one gene expression signature selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8; at least one gene expression signature selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17; and at least one gene expression signature selected from the group consisting of SEQ ID NO:18, SEQ ID NO:19, SEQ ID NO:20, SEQ ID NO:21, SEQ ID NO:22 and SEQ ID NO:23.

In another embodiment, the gene expression signatures are detected using quantitative RT-PCR or comparable methods of estimating the abundance of mRNA molecules in a sample. In one embodiment, the Cu-COX complex is detected using SEC-UV-Vis-ICP-MS.

In another embodiment, the method of the present invention also includes the step of providing personalized therapy to the subject if an elevated risk of recurrence of clear cell renal cell carcinoma is determined. In one embodiment, the therapy involves administering a therapeutically effective amount of mitochondrial respiratory complex inhibitors, angiogenic inhibitors, inhibitors of the mTOR pathway, immune checkpoint inhibitors, mitoriboscins, inhibitors of mitoribosomes or combinations thereof to the subject. In another embodiment, the therapy involves administering a therapeutically effective amount of biguanides, metformin, phenformin, BAY-872243, IACS-010759, dihydroorotate dehydrogenase inhibitors, such as leflunomide, brequuinar, teriflunomide or combinations thereof to the subject. In another embodiment the therapy involves administering a therapeutically effective amount of copper chelators, such as D-penicillamine:(S)-2-amino-3-mercapto-3-methylbutanoic acid (DPA), Tetrathiomolybdate (TM), Trientine: triethylenetetramine dihydrochloride (TETA), 5,7-Dichloro-2[(dimethylamino) methyl] quinolin-8-01 (PBT2), 2,3-Dimercaptosuccinic acid (DMSA) or combinations thereof to the subject.

In another embodiment, it is determined that the subject has an elevated risk of recurrence of clear cell renal cell carcinoma if the level of Cu-COX complex identified is higher than 0.45 ng $g^{-1}$ expressed as copper concentration and if the gene expression signatures include certain sequences. In one embodiment, these include at least two gene expression signatures selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8; at least two gene expression signatures selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17; and at least two gene expression signatures selected from the group consisting of SEQ ID NO:18, SEQ ID NO:19, SEQ ID NO:20, SEQ ID NO:21, SEQ ID NO:22 and SEQ ID NO:23.

In one embodiment, it is determined that the subject has an elevated risk of recurrence of clear cell renal cell carcinoma if the level of Cu-COX complex identified is higher than 0.45 ng $g^{-1}$ expressed as copper concentration and if the gene expression signatures include at least the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23.

In one embodiment, the method further includes detecting and quantifying the total copper in a kidney tumor tissue sample or kidney tumor biopsy from the subject and determining that the subject has an elevated risk of recurrence of clear cell renal cell carcinoma if the level of total copper identified is higher than 4.5 ng $g^{-1}$ expressed as total copper concentration.

Another embodiment of the present invention is a method of determining the level of follow-up surveillance needed in a subject after tumor removal related to clear cell renal cell carcinoma. The method involves a) detecting the gene expression signatures of mitochondrial electron transport chain subunits, mitochondrial ribosomal proteins, major histocompatibility complex class II (MHC-II) proteins or combinations thereof in a kidney tumor tissue sample or kidney tumor biopsy from the subject; and b) detecting and quantifying Cu-COX complex in a kidney tumor tissue sample or kidney tumor biopsy from the subject. Then, the method involves identifying if the level of Cu-COX complex identified is higher than 0.45 ng $g^{-1}$ expressed as copper concentration is detected, or if the gene expression signatures include certain sequences. In one embodiment, these include at least one gene expression signature selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8; at least one gene expression signature selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17; and at least one gene expression signature selected from the group consisting of SEQ ID NO:18, SEQ ID NO:19, SEQ ID NO:20, SEQ ID NO:21, SEQ ID NO:22 and SEQ ID NO:23. Finally, it is determined that a higher level of follow-up surveillance for recurrence of clear cell renal cell carcinoma is needed for the subject if such level of Cu-COX complex or gene expression signatures are identified than for a subject that does not have such level of Cu-COX complex or gene expression signatures. In one embodiment, the gene expression signatures are detected using quantitative RT-PCR or comparable methods of estimating the abundance of mRNA molecules in a sample.

In another embodiment, the method of the present invention also includes the step of providing personalized therapy to the subject if an elevated risk of recurrence of clear cell renal cell carcinoma is determined. In one embodiment, the therapy involves administering a therapeutically effective amount of mitochondrial respiratory complex inhibitors, angiogenic inhibitors, inhibitors of the mTOR pathway, immune checkpoint inhibitors, mitoriboscins, inhibitors of mitoribosomes or combinations thereof to the subject. In another embodiment, the therapy involves administering a therapeutically effective amount of biguanides, metformin, phenformin, BAY-872243, IACS-010759, dihydroorotate dehydrogenase inhibitors, such as leflunomide, brequuinar, teriflunomide and combinations thereof to the subject. In another embodiment the therapy involves administering a therapeutically effective amount of copper chelators, such as D-penicillamine:(S)-2-amino-3-mercapto-3-methylbutanoic acid (DPA), Tetrathiomolybdate (TM), Trientine: triethylenetetramine dihydrochloride (TETA), 5,7-Dichloro-2[(dimethylamino) methyl]quinolin-8-ol (PBT2), 2,3-Dimercaptosuccinic acid (DMSA).

In one embodiment, it is determined that a higher level of follow-up surveillance for recurrence of clear cell renal cell carcinoma is needed for the subject if the gene expression signatures include certain sequences. In one embodiment, these include at least two gene expression signatures selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8; at least two gene expression signatures selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17; and at least two gene expression signatures selected from the group consisting of SEQ ID NO:18, SEQ ID NO:19, SEQ ID NO:20, SEQ ID NO:21, SEQ ID NO:22 and SEQ ID NO:23.

In another embodiment, it is determined that a higher level of follow-up surveillance for recurrence of clear cell renal cell carcinoma is needed for the subject if the gene expression signatures include at least the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23.

BRIEF DESCRIPTION OF THE DRAWINGS

The foregoing summary, as well as the following detailed description of preferred embodiments of the application, will be better understood when read in conjunction with the appended drawings.

FIGS. 5, 6, 7, 8A, 8B, 8C, 8D, 9, 10, 11 and 12 identify the mRNA sequences for embodiments of the present invention of the gene expression signatures from mitochondrial electron transport chain subunits. Specifically, SEQ ID NO:1, SEQ ID NO: 2, SEQ ID NO:3, SEQ ID NO:4, SEQ ID NO: 5, SEQ ID NO:6, SEQ ID NO:7 and SEQ ID NO:8.

FIGS. 13, 14, 15, 16, 17A, 17B, 18, 19, 20, 21A and 21B identify the mRNA sequences for embodiments of the present invention of the gene expression signatures from mitochondrial ribosomal proteins. Specifically, SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17.

FIGS. 22, 23A, 23B, [[23C,]] 24A, 24B, 24C, 25, 26 and 27 identify the mRNA sequences for embodiments of the present invention of the gene expression signatures from major histocompatibility complex class II (MHC-II) proteins. Specifically, SEQ ID NO:18, SEQ ID NO:19, SEQ ID NO:20, SEQ ID NO:21, SEQ ID NO:22 and SEQ ID NO:23.

DETAILED DESCRIPTION

Figure 1A:
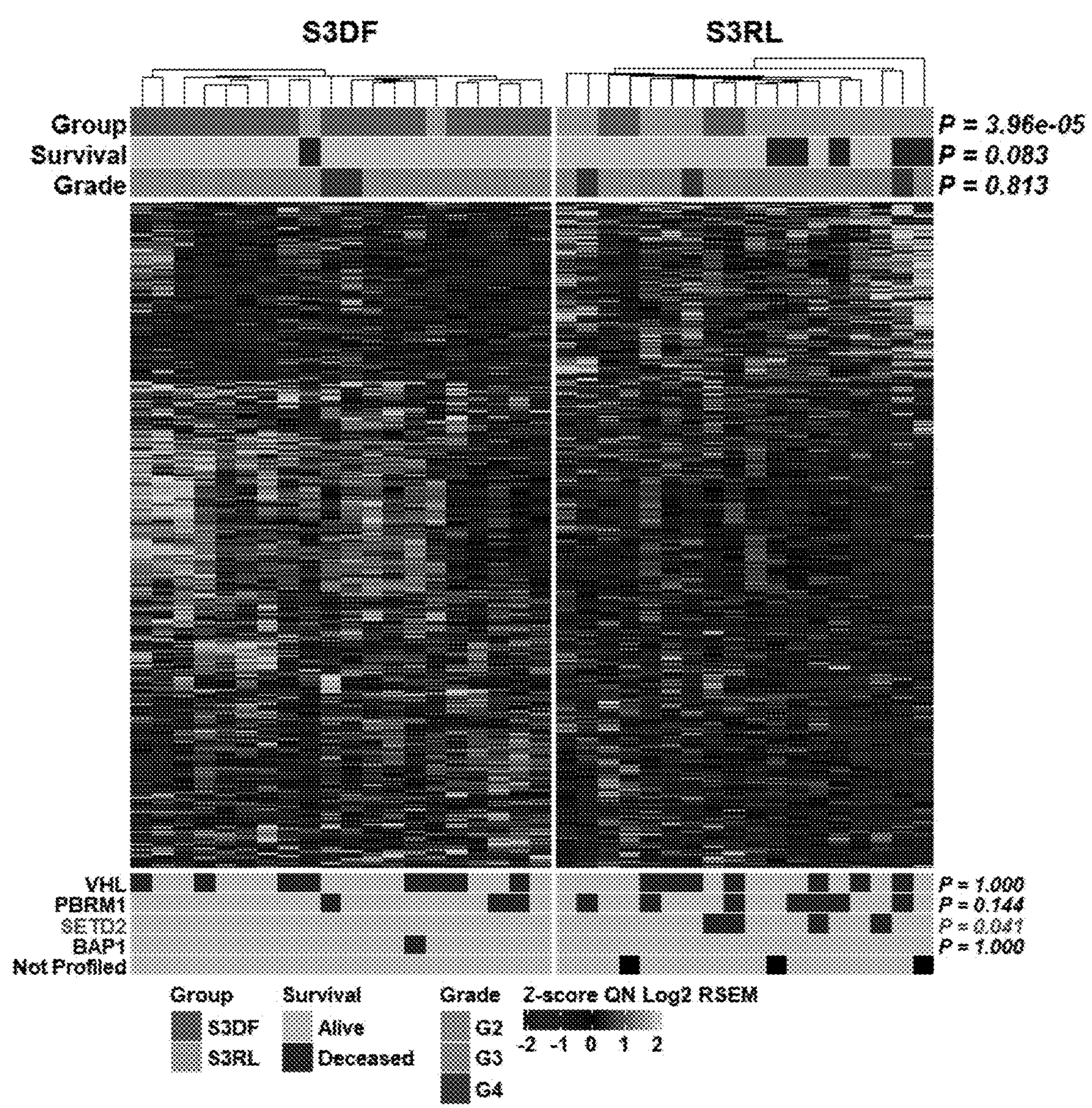
FIG. 1A is a heatmap of 1267 genes stratified by patients with stage 3 ccRCCs into those who within 24 months after initial nephrectomy remained disease free (S3DF, green) and those who relapsed (S3RL, orange).

The details of one or more embodiments of the disclosed subject matter are set forth in this document. Modifications to embodiments described in this document, and other embodiments, will be evident to those of ordinary skill in the art after a study of the information provided herein.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms “a,” “an,” and “the” include the plural, and reference to a particular numerical value includes at least that particular value, unless the context clearly dictates otherwise. Ranges may be expressed herein as from “about” or “approximately” one particular value and/or to “about” or “approximately” another particular value. When such a range is expressed, another embodiment includes from the one particular value and/or to the other particular value. Similarly, when values are expressed as approximations, by use of the antecedent “about,” it will be understood that the particular value forms another embodiment.

An “effective amount” or “therapeutically effective amount” of a composition, as used herein, is a predetermined amount calculated to achieve a desired effect.

As used herein, the term “gene expression signature” means a steady-state levels of mRNA expression for the individual genes in an indicated set of genes with validated specificity in terms of diagnosis, prognosis or prediction of therapeutic response.

As used herein, the term “Cu-COX complex” means Cu in to the cytochrome C oxidase (COX) obtained from an HMW peak in SEC-ICP-MS.

While the following terms are believed to be well understood by one of ordinary skill in the art, definitions are set forth to facilitate explanation of the disclosed subject matter. Unless defined otherwise, all technical and scientific terms used herein have the same meaning as commonly understood by one of ordinary skill in the art to which the disclosed subject matter belongs.

As used herein, the term “about,” when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Renal cell carcinoma (RCC) is amongst the top 10 most common cancers and an estimated 73,750 new diagnoses with 14,830 deaths are estimated to have occurred in 2020. Clear cell renal cell carcinoma (ccRCC) is the most common type of kidney cancer, accounting for approximately 85% of the total cases. Management of patients with localized or locally advanced RCC involves surgical resection. However, 20-40% of all localized kidney cancer patients tend to experience a relapse, the risk is increased to almost 50% in those with high risk features. Adjuvant treatment in high-risk localized kidney cancer is a relatively new concept and the only drug with FDA approval in this setting is the vascular endothelial growth factor (VEGF) tyrosine kinase inhibitor (TKI), sunitinib (NCCN). This drug showed an improvement in disease-free survival (DFS) in the S-TRAC phase-III clinical trial. However, improvement in DFS did not translate into an overall survival (OS) benefit for patients at high-risk of relapse post-nephrectomy. Several other trials using TKIs failed to meet their primary endpoints and several other trials utilizing immune checkpoint inhibitors are currently underway.

In the past, risk of recurrence after surgery was estimated using tumor characteristic such as tumor size, grade, necrosis, and lymph node involvement. Predictive models were developed using these characteristics and include the SSIGN score, developed by the Mayo Clinic (included stage, size, grade and necrosis). The same model was subsequently modified to lymph node involvement and was proposed as the Leibovich prognosis score. Another score, University of California Los Angeles Integrated Staging System (UISS) incorporates metastasis in addition to the Fuhrman nuclear grade and the Eastern Cooperative Oncology Group (ECOG) performance status. These predictive scores are used in clinic to select patients at high risk for recurrence after surgery and hence likely to benefit from adjuvant therapy. However, these scores lack prospective validation and often times do not correlate accurately with the risk of recurrent disease.

Subsequently, gene signatures have been developed to help predict the risk of recurrence in kidney cancer, akin to scores being used in other cancers such as breast cancer. A 34-gene signature was developed by Brooks et al, validated in The Cancer Genome Atlas (TCGA) database. These findings were further validated in independent clinical specimens using the NanoString platform on a cohort of 157 localized ccRCC samples. While the score was able to prognosticate ccRCC samples into subsets at greatest vs low risk for recurrence, further validation in clinical trials has not been done for adoption into clinical practice. Subsequently, Rini et al. developed a 16-gene signature to predict clinical outcomes of stage I-III ccRCC. While this score seemed promising, upon further validation in the phase-III STRAC trial (sunitinib vs placebo as adjuvant therapy), it was able to stratify patients (HR for recurrence 9.18; 95% CI 2.15-39.24; P<0.001) in the placebo arm; but interaction of recurrence score results in the sunitinib arm were not significant. Another score based on gene expressions was the CCP score, developed and validated by Morgan et al in a ccRCC cohort that consisted of 670 patients. Higher CCP scores were found to be associated with higher disease specific mortality (HR of 3.38 per inter-quartile range; 95% CI 2.21-5.16). However, using the array-based method, CCP score failed to risk stratify ccRCC patients in the TCGA as well as an institutional cohort at Yale Cancer Centre.

In summary, none of these scores are used in clinical practice due to lack of validation studies. Clearly, there is an urgent need to identify biomarkers to guide therapeutic decisions as well as for risk stratification in patients with localized ccRCC undergoing surgical resection and this currently represents a major gap.

The present invention has identified a specific set of gene expression signatures that is useful for diagnosing the likelihood of recurrence of clear cell renal cell carcinoma in a subject. In addition, the present invention has identified specific levels of copper present in tumor samples that are also useful for diagnosing the likelihood of recurrence of clear cell renal cell carcinoma in a subject. In one embodiment, both diagnostic measurements are used in conjunction to diagnose the likelihood of recurrence of clear cell renal cell carcinoma in a subject.

Methods

Gene Expression Signatures

The present invention provides a method of diagnosing the likelihood of recurrence of clear cell renal cell carcinoma in a subject using gene expression signatures. The invention uses samples from kidney tumor tissue samples or a kidney tumor biopsy from a subject with a ccRCC. In the present invention, gene expression signatures are obtained from a variety of biological sources. Non-limiting examples include mitochondrial electron transport chain subunits, mitochondrial ribosomal proteins, major histocompatibility complex class II (MHC-II) proteins.

In one embodiment, the method of the present invention determines that the subject has an elevated risk of recurrence of clear cell renal cell carcinoma if the gene expression signatures include certain sequences. In one embodiment, these include at least one gene expression signature selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8; at least one gene expression signature selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17; and at least one gene expression signature selected from the group consisting of SEQ ID NO:18, SEQ ID NO:19, SEQ ID NO:20, SEQ ID NO:21, SEQ ID NO:22 and SEQ ID NO:23. The first group of sequences are from mitochondrial electron transport chain subunits. The second group of sequences are from mitochondrial ribosomal proteins. The third group of sequences are from major histocompatibility complex class II (MHC-II) proteins.

In another embodiment, it is determined that the subject has an elevated risk of recurrence of clear cell renal cell carcinoma if the gene expression signatures include certain sequences. These include at least two gene expression signatures selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8; at least two gene expression signatures selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17; and at least two gene expression signatures selected from the group consisting of SEQ ID NO:18, SEQ ID NO:19, SEQ ID NO:20, SEQ ID NO:21, SEQ ID NO:22 and SEQ ID NO:23.

In another embodiment, it is determined that the subject has an elevated risk of recurrence of clear cell renal cell carcinoma if the gene expression signatures include at least the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23.

In one embodiment, the gene expression signatures are detected using quantitative RT-PCR or comparable methods of estimating the abundance of mRNA molecules in a sample. A non-limiting example of such a comparable method is Nanostring. In one embodiment, the quantity of mRNA used for the analysis is less than 1 nanogram.

Tobacco Smoking

The present invention has also discovered a correlation between gene expression signatures and subjects with a history of tobacco smoking. Expression of these signature genes can be used to identify tobacco smokers with particularly elevated risk of ccRCC disease and be responsive to the therapies listed below. In one embodiment, the present invention is a method of diagnosing the likelihood of developing clear cell renal cell carcinoma in a subject with a history of tobacco smoking. The method involves a) detecting the gene expression signatures of mitochondrial electron transport chain subunits, mitochondrial ribosomal proteins, major histocompatibility complex class II (MHC-II) proteins or combinations thereof in a kidney tumor tissue sample or kidney tumor biopsy from the subject; and b) determining that the subject has an elevated risk of developing clear cell renal cell carcinoma if the gene expression signatures include certain sequences. In one embodiment, these include at least one gene expression signature selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8; at least one gene expression signature selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17; and at least one gene expression signature selected from the group consisting of SEQ ID NO:18, SEQ ID NO:19, SEQ ID NO:20, SEQ ID NO:21, SEQ ID NO:22 and SEQ ID NO:23.

Further, the present invention has discovered a correlation between copper levels and subjects with a history of tobacco smoking. Detection of elevated copper levels according to the present invention can be used to identify tobacco smokers with particularly elevated risk of ccRCC disease and be responsive to the therapies listed below. In one embodiment, the present invention is a method of diagnosing the likelihood of developing clear cell renal cell carcinoma in a subject with a history of tobacco smoking. The method involves detecting and quantifying total copper content and Cu-COX complex in a sample of kidney tumor tissue or kidney tumor biopsy from the subject. It is determined that the subject has an elevated risk of developing clear cell renal cell carcinoma if a) the level of Cu-COX complex identified is higher than 0.45 ng $g^{-1}$ expressed as copper concentration or b) the copper content at a molecular mass fraction between 500 kDa-250 kDa is ≥20% of the total copper in the sample. In one embodiment, the method further includes detecting and quantifying the total copper in a kidney tumor tissue sample or kidney tumor biopsy from the subject and determining that the subject has an elevated risk of recurrence of clear cell renal cell carcinoma if the level of total copper identified is higher than 4.5 ng $g^{-1}$ expressed as total copper concentration.

Therapies

In another embodiment, the method of the present invention also includes the step of providing personalized therapy to the subject if an elevated risk of recurrence of clear cell renal cell carcinoma is determined. In one embodiment, the therapy involves administering a therapeutically effective amount of mitochondrial respiratory complex inhibitors, angiogenic inhibitors, inhibitors of the mTOR pathway, immune checkpoint inhibitors, mitoriboscins, inhibitors of mitoribosomes or combinations thereof to the subject. A non-limiting example of an angiogenic inhibitor is Sunitinib. In one embodiment, the therapy involves administering a therapeutically effective amount of biguanides, metformin, phenformin, BAY-872243, IACS-010759, dihydroorotate dehydrogenase inhibitors, such as leflunomide, brequuinar, teriflunomide and combinations thereof to the subject. In another embodiment the therapy involves administering a therapeutically effective amount of copper chelators, such as D-penicillamine:(S)-2-amino-3-mercapto-3-methylbutanoic acid (DPA), Tetrathiomolybdate (TM), Trientine: triethylenetetramine dihydrochloride (TETA), 5,7-Dichloro-2[(dimethylamino) methyl]quinolin-8-ol (PBT2), 2,3-Dimercaptosuccinic acid (DMSA).

Copper Level

Another embodiment of the present invention is a method of diagnosing the likelihood of recurrence of clear cell renal cell carcinoma in a subject based on copper levels. It involves detecting and quantifying total copper and Cu-COX complex in a sample of kidney tumor tissue or kidney tumor biopsy from the subject. In one embodiment, it is determined that the subject has an elevated risk of recurrence of clear cell renal cell carcinoma if the level of Cu-COX complex identified at the molecular mass range between 500 kDa-250 kDa is higher than 0.45 ng $g^{-1}$ expressed as copper concentration. In another embodiment, it is determined that the subject has an elevated risk of recurrence of clear cell renal cell carcinoma if the copper content at the molecular mass fraction between 500 kDa-250 kDa is ≥20% of the total copper in the sample. In yet another embodiment, it is determined that the subject has an elevated risk of recurrence of clear cell renal cell carcinoma if the copper content at the molecular mass fraction between 500 kDa-250 kDa is ≥30% of the total copper in the sample. In one embodiment, the method further includes detecting and quantifying the total copper in a kidney tumor tissue sample or kidney tumor biopsy from the subject and determining that the subject has an elevated risk of recurrence of clear cell renal cell carcinoma if the level of total copper identified is higher than 4.5 ng $g^{-1}$ expressed as total copper concentration.

The Cu-COX is analyzed from tissue homogenate under non-denaturing sample preparation conditions that include but are not limited to mechanical disruptors, ultra-sonicators, cry-grinders or chemical dissolution. The Cu-COX is targeted after separation by gel filtration or size exclusion chromatography, with the possibility of alternative methods such as native gels, capillary electrophoresis, thin layer chromatography, flow field fractionation, ultra-centrifugation or the use of molecular dialysis or molecular weight cut-off filtration.

The copper analysis is performed by atomic spectroscopy including atomic absorption, atomic emission, mass spectrometry, X-Ray fluorescence, X-Ray absorption, colorimetric assays, electrochemical sensing or nuclear chemistry.

In another embodiment, the Cu-COX complex is detected using SEC-UV-Vis-ICP-MS, but comparable methods may be used. Other non-limiting examples of such methods include SEC-ICP-AOE, atomic spectroscopy including atomic absorption, atomic emission, mass spectrometry, X-Ray fluorescence, X-Ray absorption, colorimetric assays, electrochemical sensing and nuclear chemistry.

Combined Method

Another embodiment of the present invention is a method of diagnosing the likelihood of recurrence of clear cell renal cell carcinoma in a subject. The method involves a) detecting the gene expression signatures as described above; b) detecting and quantifying total copper content and Cu-COX complex in a sample of kidney tumor tissue or kidney tumor biopsy from the subject; c) determining that the subject has an elevated risk of recurrence of clear cell renal cell carcinoma if i) the level of Cu-COX complex identified is higher than 0.45 ng $g^{-1}$ expressed as copper concentration or ii) the copper content at a molecular mass fraction between 500 kDa-250 kDa is ≥20% of the total copper in the sample, and if the gene expression signatures include certain sequences. In one embodiment, these include at least one gene expression signature selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8; at least one gene expression signature selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17; and at least one gene expression signature selected from the group consisting of SEQ ID NO:18, SEQ ID NO:19, SEQ ID NO:20, SEQ ID NO:21, SEQ ID NO:22 and SEQ ID NO:23.

In another embodiment, at least two gene expression signatures from each group are used for the determination. In yet another embodiment, at least three gene expression signatures from each group are used for the determination.

In one embodiment, it is determined that the subject has an elevated risk of recurrence of clear cell renal cell carcinoma if the level of Cu-COX complex identified is higher than 0.45 ng $g^{-1}$ expressed as copper concentration and if the gene expression signatures include at least the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23.

In one embodiment, the method further includes detecting and quantifying the total copper in a kidney tumor tissue sample or kidney tumor biopsy from the subject and determining that the subject has an elevated risk of recurrence of clear cell renal cell carcinoma if the level of total copper identified is higher than 4.5 ng $g^{-1}$ expressed as total copper concentration.

Determining the Level of Follow-Up Surveillance

Another embodiment of the present invention is a method of determining the level of follow-up surveillance needed in a subject after tumor removal related to clear cell renal cell carcinoma. The method involves a) detecting the gene expression signatures of mitochondrial electron transport chain subunits, mitochondrial ribosomal proteins, major histocompatibility complex class II (MHC-II) proteins or combinations thereof in a kidney tumor tissue sample or kidney tumor biopsy from the subject; and b) detecting and quantifying total copper content and Cu-COX complex in a sample of kidney tumor tissue or kidney tumor biopsy from the subject; c) determining that the subject has an elevated risk of recurrence of clear cell renal cell carcinoma if i) the level of Cu-COX complex identified is higher than 0.45 ng $g^{-1}$ expressed as copper concentration or ii) the copper content at a molecular mass fraction between 500 kDa-250 kDa is ≥20% of the total copper in the sample, or if the gene expression signatures include certain sequences. In one embodiment, these include at least one gene expression signature selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8; at least one gene expression signature selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17; and at least one gene expression signature selected from the group consisting of SEQ ID NO:18, SEQ ID NO:19, SEQ ID NO:20, SEQ ID NO:21, SEQ ID NO:22 and SEQ ID NO:23. Finally, it is determined that a higher level of follow-up surveillance for recurrence of clear cell renal cell carcinoma is needed for the subject if such level of Cu-COX complex or gene expression signatures are identified than for a subject that does not have such level of Cu-COX complex or gene expression signatures. Patients with Cu-Cox or gene expression signature suggestive of poor prognosis may need to undergo closer surveillance in the post-nephrectomy setting as these signatures correlate with a higher risk of relapse.

In one embodiment, the gene expression signatures are detected using quantitative RT-PCR or comparable methods of estimating the abundance of mRNA molecules in a sample.

In one embodiment, it is determined that a higher level of follow-up surveillance for recurrence of clear cell renal cell carcinoma is needed for the subject if the gene expression signatures include certain sequences. In one embodiment, these include at least two gene expression signatures selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8; at least two gene expression signatures selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17; and at least two gene expression signatures selected from the group consisting of SEQ ID NO:18, SEQ ID NO:19, SEQ ID NO:20, SEQ ID NO:21, SEQ ID NO:22 and SEQ ID NO:23.

In another embodiment, it is determined that a higher level of follow-up surveillance for recurrence of clear cell renal cell carcinoma is needed for the subject if the gene expression signatures include at least the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23.

EXAMPLES

Example 1

Differential gene expression was analyzed between a set of stage III tumors from patients who remained disease free (DF) versus matched tumors from patients who relapsed (RL) within 24 months after nephrectomy. The data were obtained from the TCGA Firehose Legacy cohort and were focused on males, as the predominant population suffering from ccRCC and belonging to the Caucasian race as continuum of our previous work. The 24 months cut off was chosen based on lack of reliable survival data for later time points in the TCGA database. Moreover, focus on early recurrence allows to identify pathways specific for patients with aggressive disease. Data were accessed through C-Bioportal.

FIG. 1A is a heatmap of 1267 genes stratified by patients with stage 3 ccRCCs into those who within 24 months after initial nephrectomy remained disease free (S3DF, green) and those who relapsed (S3RL, orange). The heatmap of all differentially expressed genes shows significant stratification with disease prognosis but not tumor grade (G). The majority of deceased patients was in the S3RL category, although the p value did not reach significance potentially due to the small number of cases. Bottom bars show mutations in 4 major ccRCC tumors suppressors located on chromosome 3p. The number of mutations in SETD2 is significantly higher in S3RL tumors. Signature of 1267 genes stratified patients with stage 3 ccRCCs into those who within 24 months after initial nephrectomy remained disease free (S3DF, green) and those who relapsed (S3RL, orange).

Figure 1B:
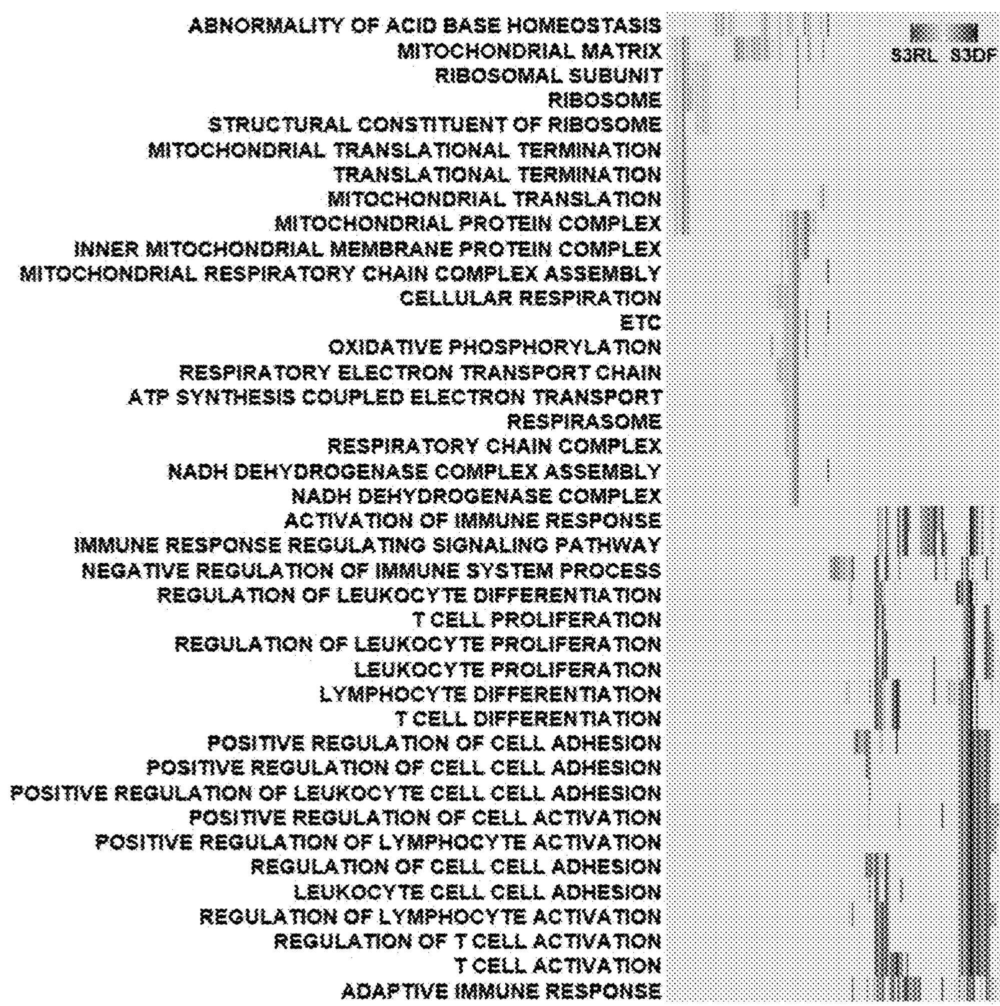
FIG. 1B is a heatmap showing clustered genes in leading edge subsets of top 20 most enriched GSEA ontology gene sets significantly associated with genes differentially regulated in S3DF and S3RL.
Figure 1C:
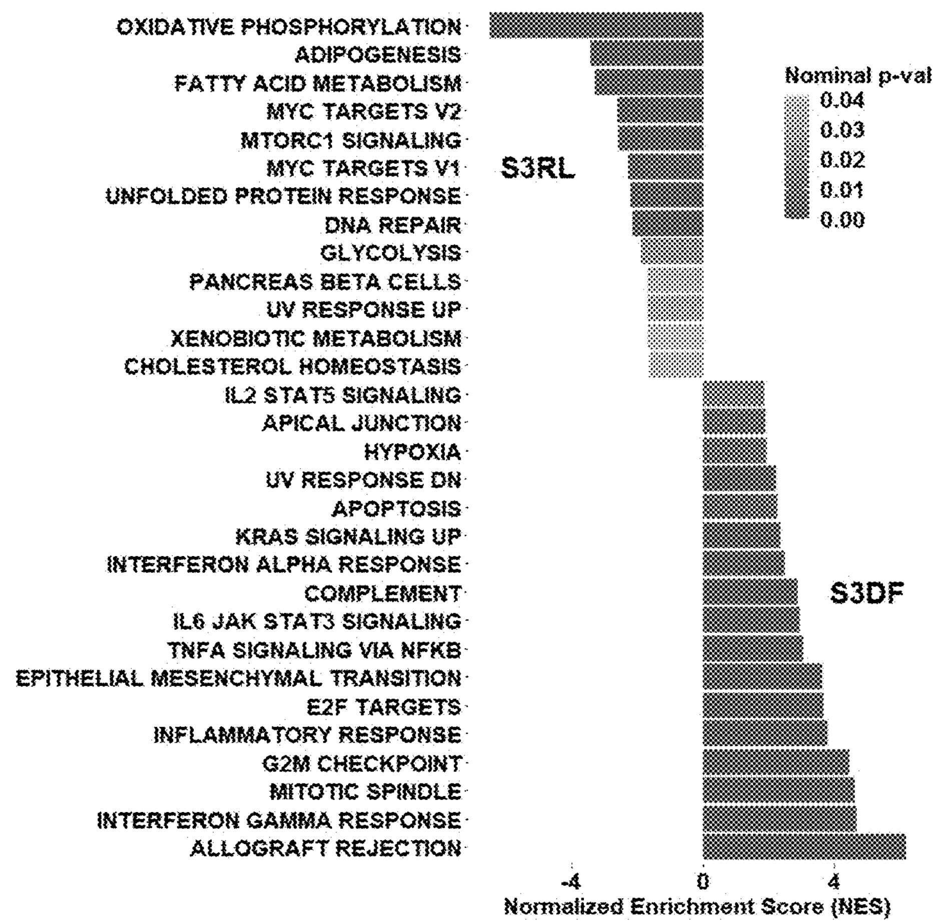
FIG. 1C is a bar plot of GSEA Hallmark gene sets significantly enriched in ccRCCs from S3DF vs S3RL.

FIG. 1B is a heatmap showing clustered genes in leading edge subsets of top 20 most enriched GSEA ontology gene sets significantly associated with genes differentially regulated in S3DF and S3RL. Pathways associated with mitochondrial activity, mitochondrial translation and electron transport chain are enriched in S3RL tumors, while pathways associated with immune and inflammatory responses are enriched in S3DF tumors. FIG. 1C is a bar plot of GSEA Hallmark gene sets significantly enriched in ccRCCs from S3DF vs S3RL. There is an enrichment for gene sets representing oxidative phosphorylation, as well as MYC and mTORC1 signaling in S3RL tumors, while gene sets defining immune and inflammatory response are overrepresented in S3DF tumors.

Example 2

Figure 2:
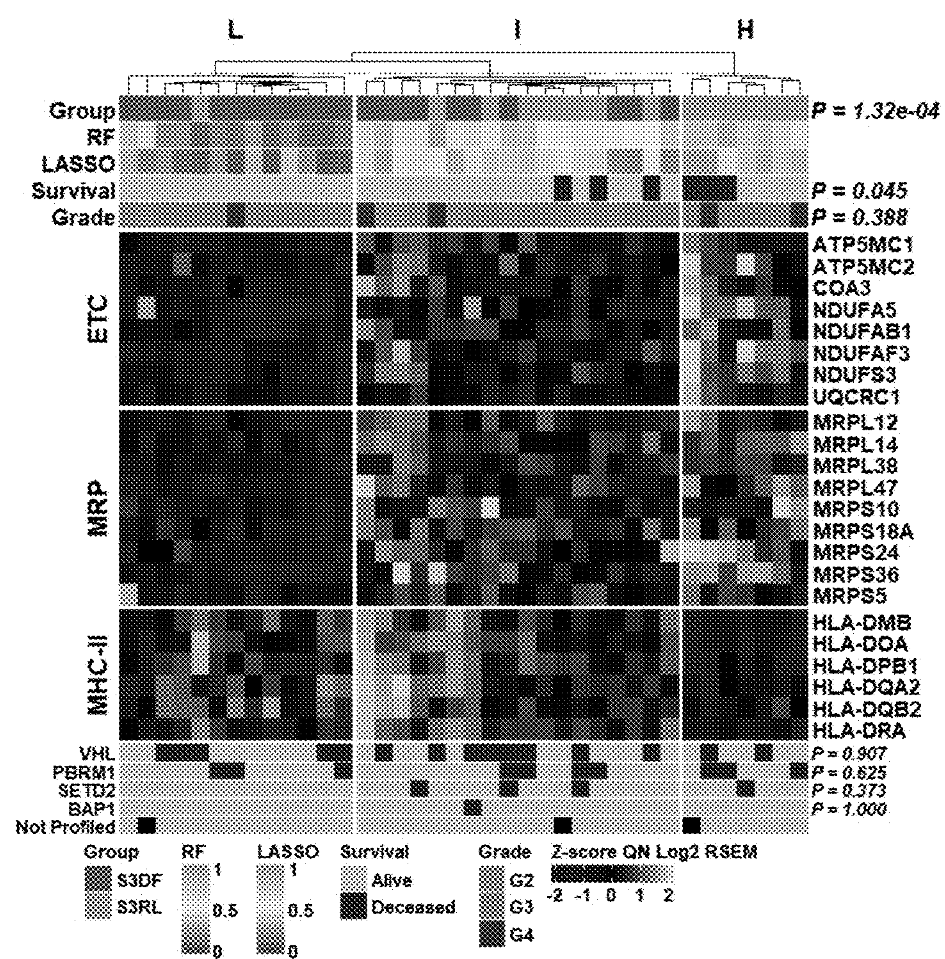
FIG. 2 is a 23-gene signature of genes encoding subunits of electron transport chain (ETC), mitochondrial ribosomal proteins (MRP) and major histocompatibility complex class II (MHC-II).

FIG. 2 is a 23-gene signature of genes that are useful for diagnosing the likelihood of recurrence of clear cell renal cell carcinoma in a subject. The 23-gene signature of genes encoding subunits of electron transport chain (ETC), mitochondrial ribosomal proteins (MRP) and class II major histocompatibility complex (MHC-II) stratify stage 3 ccRCC into low- (L), high- (H) or intermediate (I) risk of relapse. Deceased patients are significantly overrepresented in the high-risk group and absent in the low risk group. Grade does not associate with risk group.

Example 3

Figure 3A:
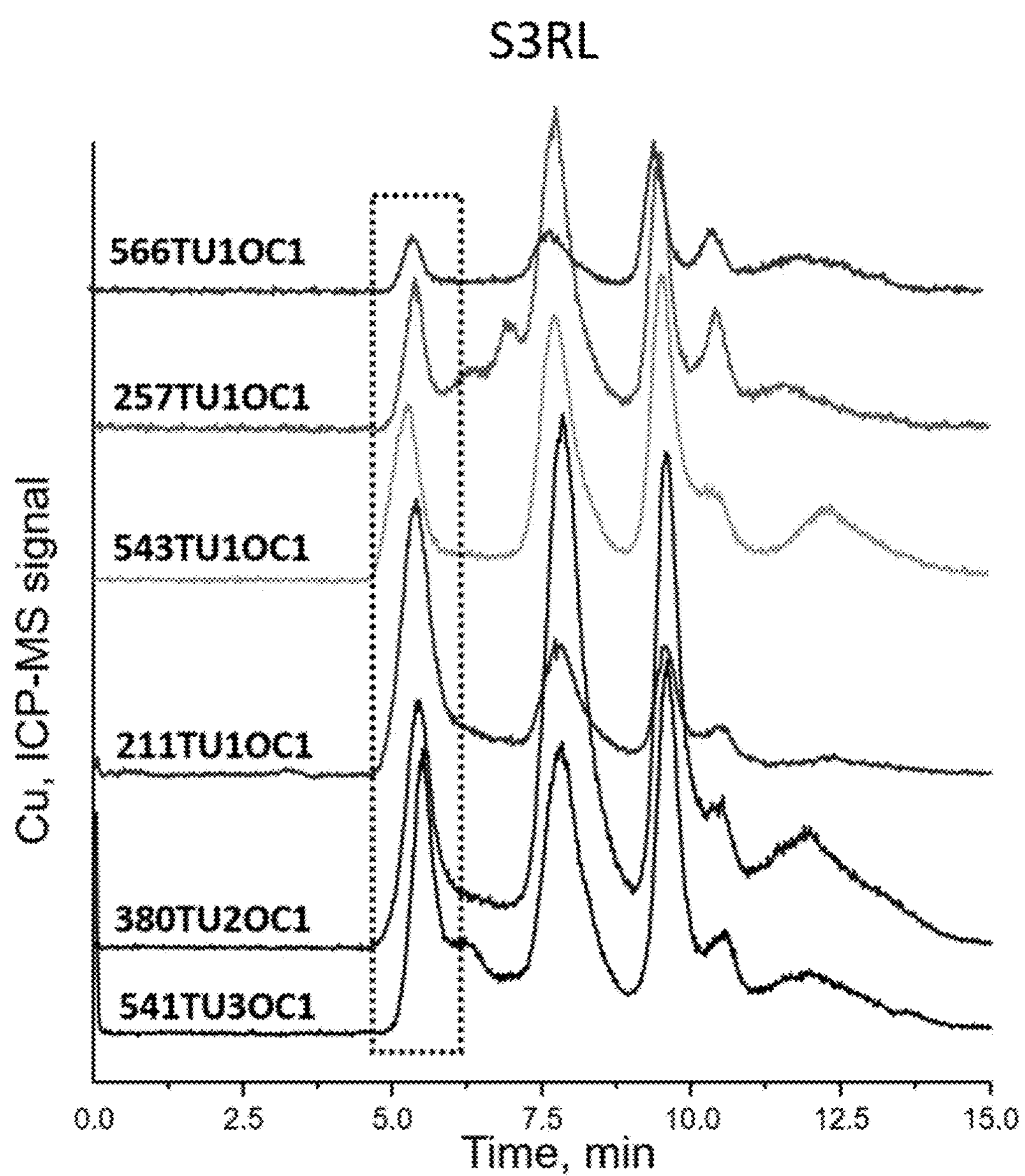
FIG. 3A is a graph showing the signal copper peak corresponding to 500-400 kDa for S3RL tumors.
Figure 3B:
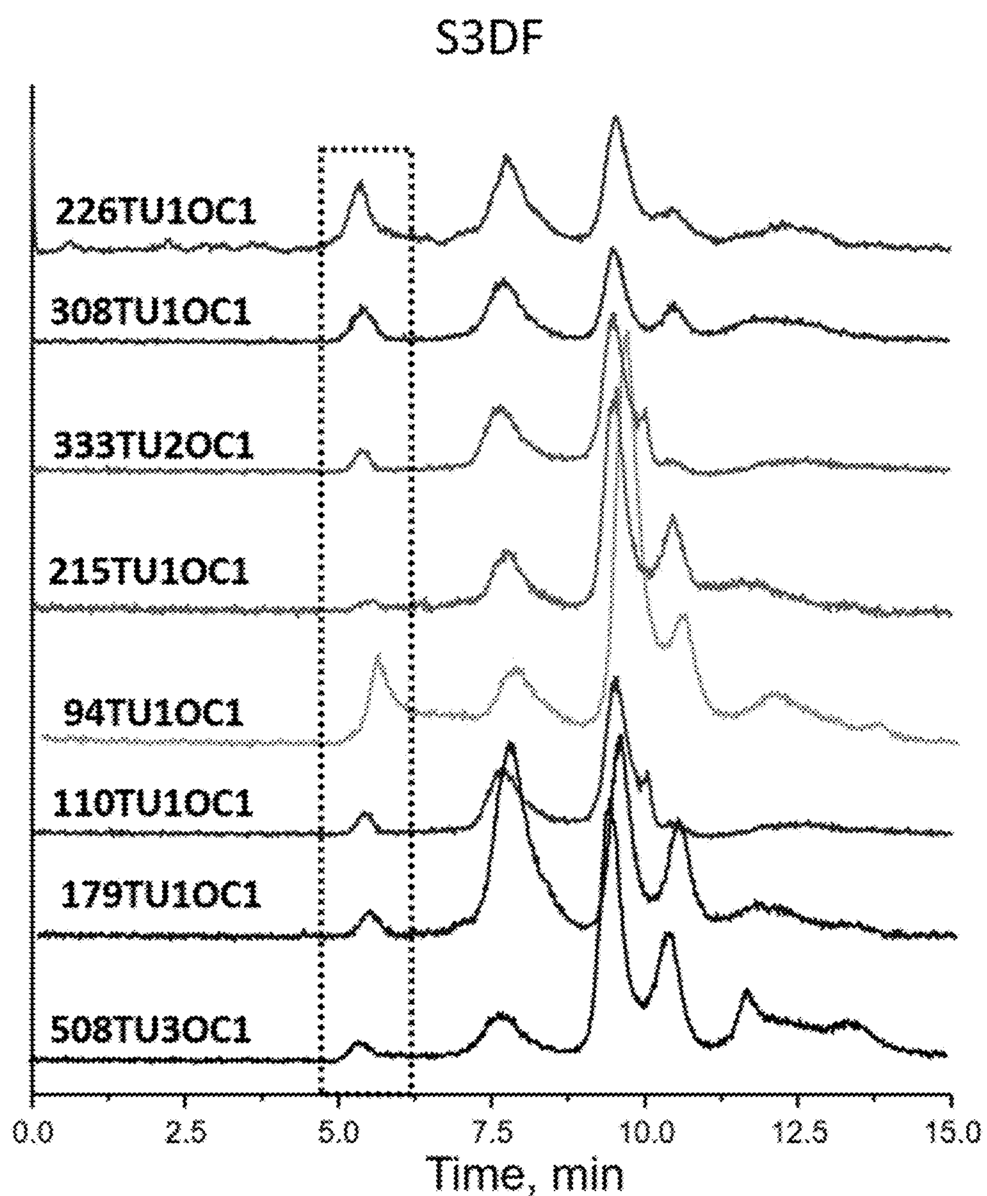
FIG. 3B is a graph showing the signal copper peak corresponding to 500-400 kDa for S3DF tumors.

Five tumor cuts of 5 μm thickness per sample were homogenized and lysed in a protein extraction buffer in the presence of an EDTA-free protease inhibitor with assistance of an ultra-sonication micro-probe in an ice bath. The extracted solution was filtered against a 0.45 μm membrane and 100 μl injected to a high-performance liquid chromatograph instrument with 50 mM ammonium acetate pH 7.4 as mobile phase with a size exclusion column with a 700-2 kDa exclusion range. The HPLC system was connected to an inductively coupled plasma mass spectrometer tuned for copper analysis in time resolved mode. FIG. 3A is a graph showing the signal copper peak corresponding to 500-400 kDa for S3RL tumors. The peak was characterized as Cu-COX complex by using a set of MT-CO2 and COX4 antibodies against subunits of the complex IV. The copper concentration in this peak was calculated against copper standards and normalized to the total phosphorous content in each sample extract. FIG. 3B is a graph showing the signal copper peak corresponding to 500-400 kDa for S3DF tumors.

Figure 4A:
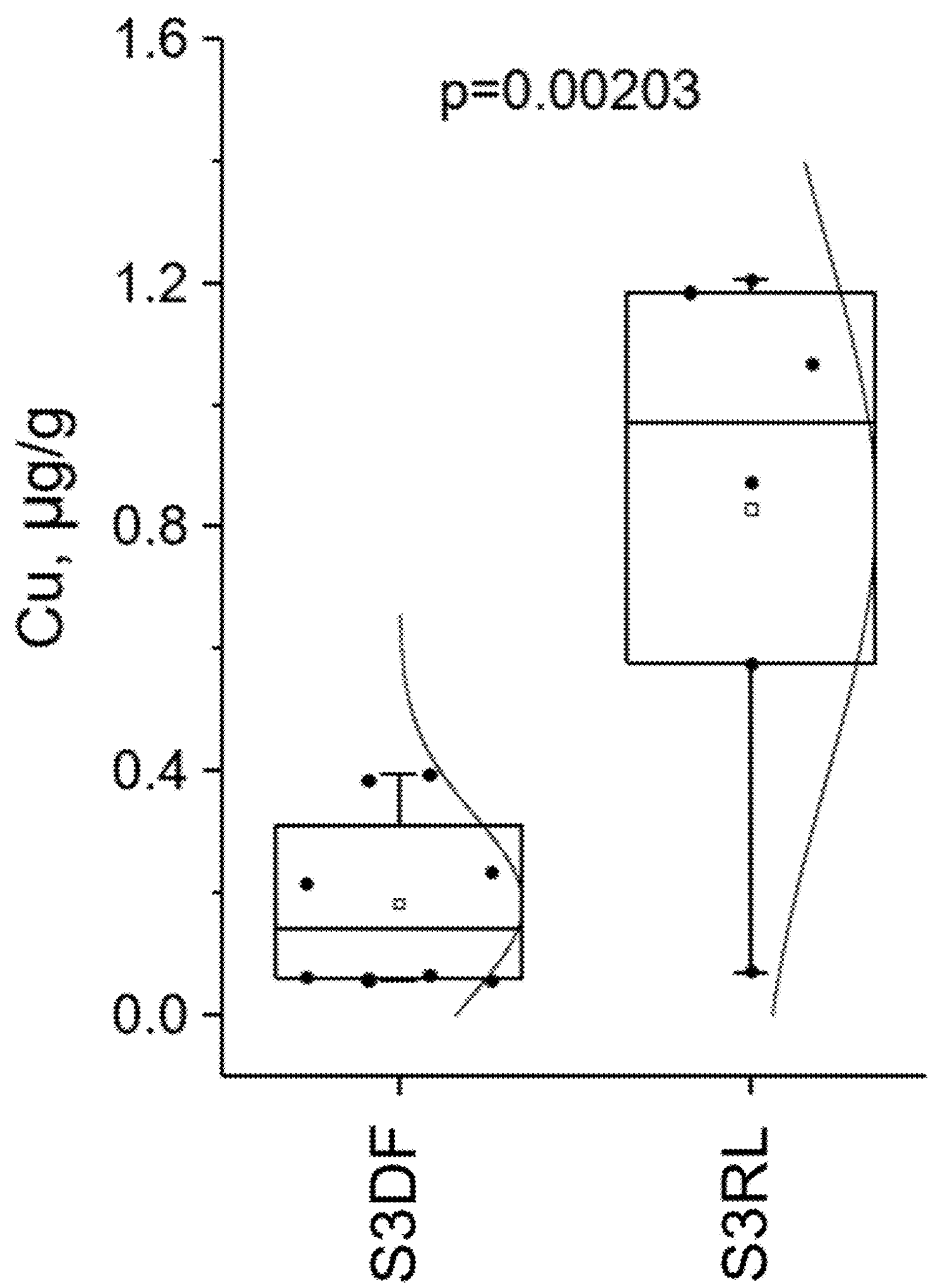
FIG. 4A shows box-whisker plots showing the copper concentration in the Cu-COX chromatographic peak from tumors from S3RL and S3DF patients.
Figure 4B:
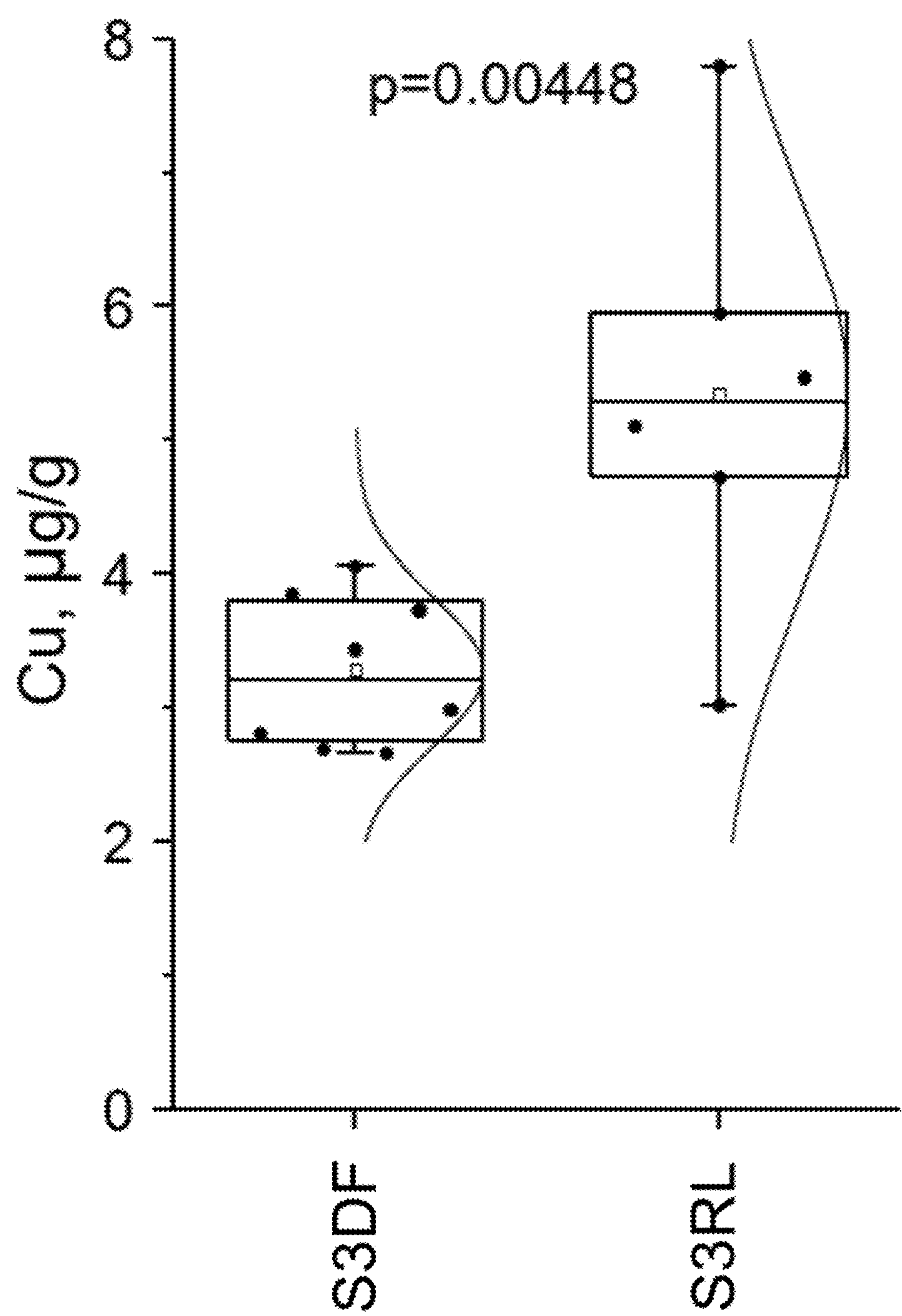
FIG. 4B is a pair of box-whisker plots showing the total copper concentration in the tumor cuts from S3RL and S3DF patients.

The total copper in each extracted solution is representative of the total content of copper in the original tumor material. It was quantified against a copper and phosphorous calibration curve, after acidification and the addition of yttrium as internal standard. The remaining pellet after the extraction was digested in concentrated nitric acid and analyzed for its copper content, which represented less than 10% of the total copper content. FIG. 4A is a pair of box-whisker plots showing the copper concentration in the tumor cuts for the copper in the Cu-COX chromatographic peak. FIG. 4B is a pair of box-whisker plots showing the copper concentration in the tumor cuts for total copper in the tumor material.

Example 4

Cohorts of tumors and kidney tissues from Caucasian males who were never smokers (NS) or lifetime smokers (LTS) at the time nephrectomy were assembled. The cohorts of NS and LTS Caucasian males did not differ in average age, BMI, tumor grade or VHL mutation status. RNAseq was performed on 19 ccRCCs from LTS and 15 from NS, and on 16 normal kidney tissues (NKTs) from LTS and 15 from NS. The concentration and quality of RNA did not differ among the groups. ccRCCs and NKTs from LTS show respectively a 64% induction (125 out of 199 genes) and 83% repression (234 out of 280 genes) of differentially expressed genes as compared to NS, with little overlap. Unsupervised clustering using differentially expressed genes (FDR<0.1) and Pearson correlation-based distance measures stratified the majority of ccRCCs and NKTs by smoking status. Importantly, in ccRCCs gene expression correlated with smoking status more effectively than either tumor grade or VHL status, suggesting a dominant effect of TS exposure in either the etiology or functional status of ccRCC. This was further supported by the ROC curves for the classification of the samples into groups defined by smoking, grade, or VHL mutations. Thirty-eight out of 125 (30.4%) upregulated genes are genes regulating metabolism, of which 18 genes showed significant enrichment for proteins from mitochondrial respiratory chain as shown in GSEA. The significant induction of each gene in the ccRCCs but not NKTs from LTS was further confirmed by nonparametric analysis. These include genes for mitochondrial calcium and pyruvate transporters, subunits of complex I, II and III, subunits of ATP synthase and malate dehydrogenase 1(MDH1), cytosolic enzyme necessary for the activity of malate aspartate shuttle (MAS). ChIP Enrichment Analysis (ChEA) and ENCODE analysis of transcription factors regulating 18 mitochondrial genes upregulated by TS in ccRCC showed significant ($P<0.05$) enrichment for transcription factors YY1, TAF1, ATF2, BRCA1, FLI1 and ZBTB33. Of those, YY1 is a Zn-binding multifunctional transcription factor member of polycomb group protein family shown to regulate mitochondrial oxidative function. TAF1 and ATF2 have histone acetylase activity and Zn-finger protein, ZBTB33, binds to active promoters. Another subgroup of metabolic genes induced in ccRCC in LTS were genes associated with lipid and steroid metabolism, however, these genes did not identify any particular GSEA or Enrichr category.

Genes downregulated in ccRCC from LTS did not show enrichment for any pathways identified by GSEA or in Enrichr. One downregulated gene is AKR1B10, an aldoketo reductase that utilize NADH/NADPH as cofactors which has been reported to be upregulated by TS in airway epithelium.

Genes upregulated in NKTs from LTS were identified by GSEA as genes associated with response to arsenic toxicity. Consistent with the metal-associated pattern of gene expression, analysis all genes upregulated in NKTs from LTS using GO Biological Process 2018 revealed pathways related to response to Copper, Cadmium and Zinc. Two induced genes, AKR1C3 and EPHX1, participate in metabolism of benzo (a)pyrene, a Group 1 carcinogen present in TS.

In contrast to tumors, the majority of genes were downregulated in NKTs from LTS. The GSEA categories of genes/pathways downregulated by TS in NKTs included genes regulating extracellular matrix and genes controlled by polycomb repressor complex 2 (PRC2). Repression of genes involved in extracellular matrix remodeling indicate that kidney tissues from LTS likely represent different microenvironment for tumor growth. Overall, RNAseq analysis implicates major tobacco smoke induced metabolomic reprogramming towards oxidative mitochondrial function in tumors from LTS.

Example 5

Considering the major effect of TS exposure in transcriptional classification indicating metabolic reprogramming of ccRCCs, metabolic profiles were analyzed according to TS exposure in ccRCCs and NKTs. LC-MS metabolomics analysis was performed on 19 NKTs and 18 ccRCCs from LTS and 18 pairs from NS. To enhance cross-sample comparability, each sample was standardized by addition of equal volumes of a balanced mixture of heavy labeled metabolite extracts obtained from cells cultured in IROA-300 95% $^{13}C$ heavy labeled media for normalization and validation purposes. Unsupervised clustering of 133 differentially abundant (FDR<0.05) revealed stratification of sixty-eight metabolites in steady-state levels between NKTs and ccRCCs. Forty-six metabolites showed higher abundance while 22 showed lower abundance in ccRCCs as compared to matched kidney tissues. Among the most abundant, metabolites from pyrimidine biosynthesis, glutathione, intermediates of glycolysis and pentose phosphate pathways, as well as arginine and glutamine were found. NADH levels were higher and NAD lower in ccRCCs, implying altered redox potential between tumors and kidneys. ATP levels were increased in tumors, but did not differ between NS and LTS. Metabolic pathway enrichment analysis using all metabolites with increased abundance in ccRCCs compared to KT by Metaboanalyst revealed the Warburg effect at the top of the list, consistent with the well-established role of this pathway in ccRCC, resulting from loss of VHL and activation of HIF.

Analysis of steady-state metabolites from NKTs and tumors by TS exposure at FDR<0.05 showed 9 metabolites increased and 6 metabolites decreased in kidney tissues, and an increase and decrease in 4 metabolites in tumors. The metabolite with the highest abundance in both NKTs and ccRCCs from LTS was phenylacetylglutamine (PAGln), a metabolite alternative to urea in nitrogen excretion. PAGln abundance is increased in genetic disorders of urea cycle and activation of this pathway with sodium phenylbutyrate or sodium phenylacetate is clinically used for treatment of urea cycle disorders and hyperammonemia. Increased production of PAGln in tissues from smokers is likely an adaptive response to ammonia present in TS. The enzyme synthesizing PAGln, Glycine-N-Acyl-Transferase (GLYAT), is also involved in detoxification of xenobiotics, including those in TS. Synthesis of PAGln consumes large amounts of glutamine (Gln), and an interesting side effect of high PAGln production is decrease in the levels of branched-chain amino acids (Leu, Ileu, Val). This is likely due to the utilization of glutamate (Glu), which is generated at the first step of branched-chain amino acids degradation, that can serve as Gln source. Interestingly, one of the metabolites increased in KT from LTS is hydroisocarpoic acid (HICA), a degradation product of Leu, supporting similar effects in LTS. Changes in Leu abundance were not measured, possibly due to the augmented supply at the organismal level, however data imply augmented utilization of leucine in the degradation pathway, which may limit availability of Leu for its other activities. Leu plays a protective role in cigarette smoke induced cell death through induction of mTOR activity. Thus, high levels of PAGln production may have an overall effect diminishing mTOR activity and its role in anabolic effects supporting health of normal kidney cells and survival and proliferation of cancer cells. Other metabolites with abundances augmented in NKTs from LTS include glycolytic metabolites, acetoacetate, acetyllysine, IMP, methylthioadenosine (MTA), a metabolite in polyamine synthesis, and UDP-glucose. Interestingly, three amino acids lysine (Lys), tryptophan (Trp) and histidine (His) showed higher abundance in ccRCC. This may be related to the augmented gene expression for amino acid transporters determined in RNAseq.

Four metabolites with lower abundance in both NKTs and ccRCCs from LTS are ophtalmic acid (OPH), S-adenosyl methionine (SAM), hypotaurine and GDP-glucose. OPH is γ-glutamyl-L-2-aminobutyryl-glycine tripeptide, synthesized in parallel to glutathione. Both can be donors of Glu. OPH is considered a biomarker of oxidative stress reversely correlated with GSH consumption. Thus, decrease in OPH in LTS likely results from augmented GSH synthesis. The decrease in the levels of SAM, a donor of methyl groups implicates differences in the cellular processes requiring methylation, such as DNA and histone methylation.

Example 6

Analysis of metabolites' steady-state levels provides only a narrow and limited view of metabolic landscape. Isotope tracing can reveal metabolic flux in primary tumors from patients but these approaches are necessarily limited by the adequate uptake of the labeled metabolites during presurgery infusion and their distribution within the tumor. Spearman correlation analysis (Spearman correlation coefficient (SCC) values ≥0.5) was used for the 133 metabolites in each tissue and connections among the metabolites were visualized using circos plots, where edges show connections between individual metabolites and the size of the nodes is proportional to the number of connections for each metabolite.

The number of correlations between metabolites was similar in NKTs and ccRCCs classified by TS exposure. There were clear differences in the pattern of metabolic connections for each of the tissue and NS and LTS. There were more unique than common edges, when NKTs and ccRCCs are compared irrespective of the smoking status, which is consistent with established oncogenic metabolic reprograming. Importantly however, there were more unique than common edges when NKTs or ccRCCs from NS and LTS are compared. These data show that TS induces global reprogramming of both tumor and normal kidney tissue metabolism.

Example 7

Transcriptomic reprogramming of ccRCC from LTS supports activation of oxidative phosphorylation. Both ccRCCs from NS and LTS show increased steady-state levels of ATP and higher numbers of correlations of ATP as compared to normal kidney tissues; however, the correlations of ATP were substantially different in ccRCCs from NS and LTS. Only in ccRCCs from NS, but not LTS, ATP was correlated with four glycolytic intermediates, fructose bisphosphate (FBP), glyceraldehyde phosphate (GADP), phosphoglyceric acid (PG), phosphoenolpyruvate (PEP). Consistent, tumors from NS, but not LTS, showed robust connections among glycolytic intermediates and ribose phosphate (RP), metabolite in PPP. As expected, there was an increase in the number of correlations for the glycolytic intermediates in both ccRCCs from NS and LTS as compared to the respective NKTs. However, the overall number of connections from glycolytic intermediates was diminished, and was qualitatively different in tissues from LTS as compared to the tissues from NS. In particular, the number of connections for major glycolytic intermediates, FBP, GADP, PG, PEP and pyruvate (PYR) was significantly higher in tumors from NS as compared to tumors from LTS while there were no significant differences in the number of metabolites correlated with dihydroxyacetone phosphate (DHAP), glycerol phosphate (GP) and lactate (Lac) in ccRCCs from LTS and NS. Importantly, there was a highly significant enrichment (FDR values from $2.52e^{-09}$ to $2.18e^{-02}$) for 53 essential metabolic pathways based on metabolites correlated with FBP, GADP, PGA and PEP in ccRCCs from NS, including Warburg effect, PPP, purine and pyrimidine metabolism and others, an indication that glycolysis is a central metabolic hub essential for the function of multiple pathways. In contrast, in the case of ccRCCs from LTS, there were only 8 metabolic pathways with FDR from $5.14e^{-04}$ to 0.05, including urea cycle, ammonia recycling, glutamate and aspartate metabolism, and malate aspartate shuttle (MAS). In contrast to the distinct patterns of correlations among the glycolytic metabolites in ccRCCs from NS, transcriptional expression of glycolytic genes in ccRCCs from NS or any of the investigated tissues were not correlated. While a similar disconnect between the abundances of metabolites and enzyme mRNA expression has been reported by others, lack of transcriptional correlation among glycolytic genes is surprising in view of the role of HIF in maintenance of glycolytic network. Overall, these data indicate inhibition of glycolytic pathway activity, its contribution to ATP production and overall cellular metabolism Another essential source of cellular ATP is TCA cycle and oxidative phosphorylation. In contrast to glycolysis, TCA cycle intermediates showed an overall increased number of correlations in ccRCCs from LTS as compared to NS. In particular, there was an increased number of correlations for citrate, succinate, and malate in tumors from LTS. ATP correlated differently with TCA cycle intermediates and amino acids in ccRCCs from NS and LTS. In NS, ATP correlated with acetyl-CoA (Ac-CoA), oxyglutarate (OG) and NAD, while in LTS, ATP correlated with malate, citrate, NAD and NADH. In NS, ATP correlated only with glutamate (Glu), while in LTS, it correlated with several amino acids, including Glu, Gln, ARSA, Arg and His. Correlation of ATP with malate and NAD/NADH in LTS implicates that role of malate dehydrogenase 2 (MDH2) as a source of NADH that enters respiratory complex I leading to the production of ATP by oxidative phosphorylation.

The total number of connections for malate increased from 21 in NS to 37 in ccRCCs from LTS as compared to NS. While malate was coupled only with fumarate and ARSA in tumors from both NS and LTS, it was connected to Asp, Glu, NAD and NADH and GSH/GSSG in LTS, further supporting malate-aspartate shuttle (MAS) function. The MAS transfers reducing equivalents between cytosol and mitochondria supporting both cytosolic glycolysis and mitochondrial oxidative phosphorylation. On the cytosolic site, malate dehydrogenase 1 (MDH1) catalyzes reduction of oxaloacetate (OAA) to malate; this reaction utilizes NADH and regenerates NAD, necessary for the key glycolytic enzyme glyceraldehyde 3-phosphate dehydrogenase (GAPDH). Malate is then transported into the mitochondria in exchange for 2OG by SLC25A11 carrier, and is oxidized by TCA cycle enzyme, MDH2, to OAA. This reaction utilizes NAD and generates NADH, which is available for oxidative phosphorylation by respiratory complexes producing ATP. Mitochondrial OAA undergoes transamination to Asp by GOT2, and Asp is transported out of mitochondria in exchange for Glu by SLC25A13 carrier. In the cytoplasm it undergoes transamination to OAA by GOT1. The activity of MAS in ccRCCs from LTS is further supported by increased mRNA expression of MDH1. Overall expression of mRNAs for MAS proteins represented a significantly higher average variance explained (AVE) and increased number of correlations in expression of all six MAS genes (SLC25A11, SLC25A13, MDH1, MDH2, GOT1 and GOT2) in LTS. MAS metabolites were linked to twice as many metabolites in tumors from LTS as compared to tumors from NS. The lack of correlation with OG may be indicative of extensive OG utilization as it serves as a cofactor for several enzymes contributing to epigenetic modifications, including histone demethylases and TET.

The difference in ATP links to bioenergy producing pathways in ccRCCs from NS vs. LTS was reflected also in connections of other purines (IMP, GMP, GDP, GTP and ADP). All were linked to glycolytic and PPP metabolites in ccRCCs from NS, which are absent in ccRCCs from LTS. In contrast purines from LTS were connected to argininosuccinate (ARSA), malate, citrate and fumarate, as well as Arg and Gln. One explanation is that metabolism of the purines is tightly coupled to and dependent on ATP.

Another major feature distinguishing tumors from NS and LTS were correlations of pyruvate. In ccRCCs from NS, pyruvate correlated with 24 metabolites, while the number of correlations in ccRCCs from LTS was only 5. These correlations included malate, fumarate, succinate and all four intermediates of urea cycle, argininosuccinate (ARSA), Arg, ornithine and citrulline but not ATP or lactic acid. In addition, all urea cycle intermediates were intercorrelated. Metabolites correlated with pyruvate in NS ccRCC showed significant enrichment for pathways such as Arginine and Proline metabolism, Urea Cycle, and Glutamate Metabolism as determined by Metaboanalyst. In contrast, in tumors from LTS metabolites did not show enrichment for any of the KEGG pathways. These findings support that NS ccRCCs are specifically characterized by pyruvate carboxylase-dependent anapleurosis of pyruvate into oxaloacetate (OAA) and through OAA, into Asp and ARSA, sustaining the activity of urea cycle. Such utilization of pyruvate is consistent with the inhibition of pyruvate dehydrogenase (PDH) dependent conversion to acetyl-CoA, which is inhibited by HIF-dependent induction of pyruvate dehydrogenase kinase (PDK) and with the role of pyruvate in Asp synthesis in cancer cells.

Example 8

It was observed that there was a clear switch in the connections among most amino acids, with 10 amino acids showing an increased and 7 decreased type of correlations, while serine and glycine had no change in the number of correlations. Cytosolic-mitochondrial exchange of Asp and Glu occurs in the operation of the MAS, which was transcriptionally and metabolically connected in ccRCC from of LTS. Focusing on Asp, TS diminished number of connections from 16 to 9, disrupting connections with IMP, N-acetylaspartate (NAA), aspargine (Asn), Gln, and pyroglutamate (PyrGlu), but inducing correlations with malate and Glu. This implicates function of Asp in MAS and urea cycle activity but loss of biosynthetic (IMP) and storage (NAA) functions. Aspartate transported from mitochondria through MAS derives from transamination of OAA. We propose that there are two sources of mitochondrial OAA in ccRCCs from NS, one derived from pyruvate carboxylase and another derived from malate in canonical TCA cycle. In contrast, tumors from LTS have only one pool of OAA derived from malate which is used for generation of Asp. That implies lower overall availability of Asp with primary utilization of Asp for MAS-dependent regeneration of NAD+/NADH.

The connectivity of glutamate was increased from 24 to 28 in LTS, with a major rewiring of connections away from nucleotide synthesis and into the amino acid and TCA metabolites. Correlation of Glu with 20G in ccRCC from NS suggests that the primary entry of Glu to TCA cycle is through dehydrogenation. Connections of Glu to Asp, malate, fumarate and NAD+/NADH in ccRCCs from LTS implicates glutamate anaplerosis through MAS. Correlations of Glu with His and Lys in ccRCCs from LTS suggests degradation of these amino acids, with glutamate as a major final metabolite. Importantly, the abundance of His was increased overall in LTS ccRCC corresponding with a dramatic increase in connectivity throughout the metabolome, from none in ccRCC from NS to 27 metabolites in LTS. Similar to His, the number of metabolites correlating with lysine was increased in LTS ccRCCs. The data suggest a hypothesis that Lys and His-derived Glu may contribute to the MAS activity in LTS. These data implicate increased uptake of His and Lys and dependence of tumors on their metabolism. The potential utilization of His and Lys as a source for Glu may be related to the decreased expression of SLC1A7, glutamate transporter in ccRCC from LTS.

Renal cancer cells were shown to require Gln for growth and to exhibit reprogrammed glutamine metabolism, i.e. reductive carboxylation. In this pathway, Gln maintains reverse activity of TCA cycle by entering TCA cycle through Glu and OG, which in turn through activity of isocitrate dehydrogenases is converted to citrate. Citrate can be exported to the cytosol to generate acetyl-CoA available for fatty acid synthesis or purine and pyrimidine synthesis. Data did not reveal correlations between Glu, 20G, or citrate. However, in ccRCCs from LTS, Gln connections in the metabolome were consistent with those of Glu, and therefore coupled to MAS metabolites. Despite the fact that Gln is utilized in synthesis of PAGln, which is a metabolite of which abundance is upregulated in tumors and kidney tissues from smokers, we did not detect correlations between PAGln and Gln, possibly due to excretion of PAGln in the urine.

In LTS, GSH and intermediate in GSH synthesis pathway, pyroglutmate (PyrGlu, also known as 5-oxyproline) were increasingly integrated with the metabolome. PyrGlu is an intermediate in GSH synthesis pathway, generated by γ-glutamylcyclotransferases from γ-glutamyl amino acid and converted to glutamate by 5-oxoprolinase (OPLAH). Its metabolism promotes glutathione synthesis and transport of amino acids from extracellular environment as γ-glutamyl-dipeptides. In particular several of the GSH and PyrGlu correlations were with amino acids, including Spearman correlation coefficient of 0.99 between PyrGlu and Gln. This implies a GSH/PyrGlu cycle in the transport of amino acids in ccRCCs from LTS, in addition to the canonical activities in maintaining redox homeostasis.

Example 9

Although TS-specific compounds were not detected in metabolomics analysis, TS exposure can increase the overall exposure to metals. The identification of arsenic in the transcriptomic signature upregulated by TS in ccRCCs prompted us to determine the concentrations of 15 metals (Al, As, Cd, Co, Cr, Cu, Fe, Mn, Ni, Pb, Se, Sb, U, V, Zn) in NS and LTS KT/ccRCC pairs using ICP-MS. Comparing NKTs to ccRCC, there was a clear separation of all metal concentrations between ccRCC and NKTs, characterized by increased abundance of Cd, Co, Cu, Se, U and Zn in NKTs as compared to ccRCC, irrespective of smoking status. The metallothionein content of kidney as compared to the tumor tissue is also increased, suggesting that concentrations of these metals are reflective of the aggregate metal binding activity of kidney tissue. In contrast, Fe accumulated in ccRCC as compared to NKTs, possibly related to blood perfusion as ccRCC are highly vascularized.

Stratifying samples by TS revealed significantly higher accumulation of Cd and As as well as strong significant trend in the increased accumulation of Cu in NKTs and ccRCCs from LTS. The total increase in the accumulation of Cd was accompanied by its augmented distribution across three fractions: high molecular weight proteins (HMW); metallothioneins (MTs) which are small cysteine-rich proteins buffering free metals; and the low molecular weight fraction (LMW), which includes metals that are free or bound to small metabolites. Increased levels of As, were primarily due to the accumulation of free arsenic, with no changes in its fraction bound to MT. This is likely caused by the diminished buffering capabilities of MTs due to their saturation by Cd. Activities of As depend on the oxidoreduction state and methylation as well as its intracellular distribution. TS contains inorganic arsenate ($iAs^{V}$). Intracellularly, As undergoes several steps of oxidoreductive methylations by arsenic 3-methyl transferase (AS3MT) using SAM as a source of methyl groups to generate mono- and dimethyl $As^{III}$ or $As^{V}$ ($MMA^{III}$, $MMA^{V}$, $DMA^{III}$, $DMA^{V}$). DMA is the primary As derivative excreted by kidneys into urine, and methylation is considered a process of detoxification, however, methylated forms have also oncogenic effects. Both NKTs and ccRCCs from LTS showed increased levels of inorganic As, while tumors showed also a decrease in the DMA, which is related to the decreased level of SAM in both tissues from LTS.

The difference in the total Cu accumulation between was significantly increased in ccRCCs from LTS. In particular, there was significantly increased distribution of Cu to the LMW fraction and MTs. Interestingly, however, while the total distribution of Cu to the HMW did not differ between ccRCCs from NS and LTS, there was a significant enrichment for Cu in an HMW peak corresponding to the cytochrome C oxidase (COX). In contrast, there was a decrease in the second HMW Cu peak, potentially corresponding to the superoxide dismutase. The identity of the COX-Cu peak 1 was confirmed by UV-Vis absorbance at 420 nm that corresponds to porphyrin ring and 600 to 700 nm corresponding to Copper A and Cooper B clusters. Mitochondrial COX is the terminal cupro-enzyme in the electron transport chain that transfers electron onto the molecular 02 and 4 protons are pumped across inner mitochondrial membrane that contributes to the electrochemical gradient required by the activity of ATP synthase. Increase in the Cu content in COX is consistent with activation of oxidative phosphorylation in ccRCCs from LTS. There was also a significant enrichment for genes encoding proteins related to Cu among genes differentially regulated in ccRCCs from LTS as compared to the overall percentage of such genes in RefSeq database. Importantly, several metals, including As and Cd, are present in several brands of e-cigarettes as found by us and others, an indication that e-cigarettes may continue to represent a risk factor for ccRCC.

Example 10

Next, a signature of 158 relevant genes was generated based on our metabolomic analysis, which included genes found to be upregulated in our mRNAseq analysis of ccRCC from LTS, genes encoding other subunits of the mitochondrial respiratory complexes, enzymes of TCA cycle and glycolysis. There was an increased average gene expression for this signature of genes as compared to the overall average expression for all genes that was similar in our cohort and in TCGA KIRC cohort of Caucasian males. It was determined that co-expression of the metabolic genes stratified in an unbiased way our cohort of ccRCCs into LTS and NS with three clusters of metabolic genes. The analysis of this metabolic co-expression signature using TCGA-KIRC Caucasian male cohort revealed four clusters of genes and stratified the cohort into 8 subtypes with different survival times, characterized by different patterns of co-expression of oxidative phosphorylation and glycolytic genes. Gene cluster 1 contained almost exclusively subunits of respiratory complex I, IV and V. Gene cluster 2 was characterized by the presence of glycolytic genes. Gene cluster 3 included most subunits of complex II, 5 out of 6

MAS genes, and several TCA cycle genes. The smallest gene cluster 4 included SLC25A13 (MAS) and two subunits of complex II. The best prognostic signatures were subtypes 7 and 8, both characterized by high expression and co-expression of genes in cluster 1 and 3, and in the case of subtype 7 also cluster 4. Subtype 3, also with good prognosis was characterized by high expression and co-expression of genes in cluster 3 and 4. The worse prognostic signature, subtype 2 shows high expression and co-expression of genes in cluster 1, an indication of oxidative phosphorylation driven primarily by complex I. Subtypes 1, 4, 5 and 6 had had intermediate survival times, all with different individual patterns of co-expression of respiratory complexes and TCA cycle genes.

This indicates that best survival can be predicted by coordinated high activity of oxidative phosphorylation involving all respiratory complexes and low activity of glycolysis, while the worst by high glycolytic activity and activity of complex I. Interestingly, metabolic gene signature from our cohort of LTS corresponded the closest to the TCGA subtype 7, a potential indication for the better survival of some patients with ccRCC who were current smokers at the time of diagnosis.

Biospecimens acquisition: ccRCC and NKTs were obtained from tumor banks at the University of Cincinnati, Cincinnati VA Medical Center, NCI Urology Oncology Branch and University of North Carolina at Chapel Hill. In all cases tissues were obtained after acquiring written informed consent and respective institution review board approval and were deidentifed. In most cases fresh-frozen tissues were used or in some cases samples were extracted from OTC. All samples were reviewed by expert genitourinary pathologist and derived from region in the tumor that had 80% cancer cells. DNA was isolated using DNAzol (MRC, DN127) or QIAamp DNA micro kit (Qiagen 56304). VHL was sequenced as described before Example 11

RNA was extracted using RNAlater ICE (Ambion, AM7030) following by miRNA isolation kit (Ambion, AM1560). The quality of RNA isolated was checked using Agilent BioAnalyzer. Poly-A containing mRNA was used. Strand-specific RNA-seq libraries were prepared using TruSeq Stranded Total RNA library kit from Illumina. Single-end with read length 100 bp was used. Deep sequencing was conducted using HiSeq 1000 platform. Each sample generated ~30 million reads.

Data analysis: Reads are first aligned to the reference genome and current gene definitions using TopHat aligner followed by quality control. Reads aligning to each known transcript are counted and the follow up analyses are performed using Bioconductor packages for next-generation sequencing data analysis. The differential gene expression analysis is based on the negative-binomial statistical model of read counts as implemented in the edgeR Bioconductor package for each comparison separately. P-values is FDR-adjusted for multiple testing using the false discovery rates and gene expression profiles in the heatmap are clustered using Bayesian infinite mixture model. The differential gene expression analysis is followed by enrichment analysis with CLEAN package. The raw and normalized gene expression and analysis results are submitted to Genomics Portals and will also be deposited in GEO.

Functional analysis of differentially expressed genes: The mechanistic interpretation of the lists of differentially expressed or co-clustered genes is complemented by identifying affected pathways and other groups of functionally related genes through functional enrichment analysis using Enrichr, GSEA, and related resources. The analysis is performed using a very large, locally maintained collection (>30,000) of pre-defined functionally coherent gene lists such as Gene Ontologies, KEGG pathways, the Molecular Signature Database (MSigDB), L2L database of lists of differentially expressed genes, mammalian phenotypes, human disease associated gene lists, miRNA target gene lists, lists of genes targeted by specific chemicals, and transcriptional regulatory targets. In addition to using pre-defined pathways, we will also perform a statistical network analysis to identify connected components of the global protein interaction network enriched for implicated genes.

Example 12

Tissues (15 μg) were homogenized and extracted three times with MeOH:ACN:$H_2O$ (50:30:20) in a TissueLyser II at 4° C. and centrifuged to precipitate proteins. Supernatants were ultracentrifuged through a molecular weight cut off filter to eliminate large particles. Samples were split into two fractions, one of which was analyzed as a part of a discovery phase and the second saved for future validation analysis including compound quantification. Tissue lysates were mixed 1:1 with $^{13}C$ labeled internal standard mix balanced for the metabolites of interest. Because of different abundances of individual metabolites in different lysates, the balanced standard was obtained by combining IROA yeast extract (IROA Technologies) with $^{13}C$ lysates from several human cell lines grown in the presence of 5.5 mM $U^{13}C$ for three passages. Following human cell lines were used: RCC-786-0, RCC-786-0 cells with knockdown of TKT to increase levels of metabolite in pentose phosphate pathway, HK2 cells derived from kidney proximal tubule epithelial cells, glioblastoma U87-MG cells, and DG-75 from Burkitt lymphoma. All cells were grown to ~70% confluency and fed fresh 5.5 mM glucose with 95% $U^{13}C$ glucose for an hour prior to harvesting. All adherent cell lines were extracted using 1 ml per $1\times10^6$ cells, while non-adherent lines were extracted using 1 ml per $2\times10^6$ cells. Labeled lysates were mixed using equal volumes of each.

These tissue-standard lysate mixtures were analyzed by LC-MS using hydrophilic interaction chromatography (HILIC) and reverse-phase (RP) chromatography. Data from both methods were collected in both positive and negative polarities using an Orbitrap Fusion Lumos Tribrid instrument in the Rieveschl Laboratories for Mass Spectrometry. The instrument was operated in negative ionization mode using a mass resolution of 60,000-120,000. Putative metabolites were identified in a semi-targeted manner using MAVEN with a list of commonly detected human metabolites, then validated by accurate mass to charge (<5 ppm), retention time, chemical formula compared to $^{13}C$ labeled and, if needed, ms/ms fragmentation. We identified 133 validated endogenous metabolites that could be paired with IROA metabolites Data Analysis: Data were processed in an unbiased manner using a metabolomics workflow Compound Discoverer 2.0, a commercially available program (Thermo Sci.) to detect statistically significant features. Biologically relevant compounds were determined in an untargeted manner using ClusterFinder, an algorithm created by IROA Tech. designed to find the unique isotope ratios of heavy(H) to light(L) pairs previously referred to as their "phenotyping workflow". A subset of H:L ratios and orphan peaks was validated in targeted searches using an in-house database search through MAVEN, an open source program developed at Princeton. Further validation of statistically significant features was done using MS/MS fragmentation compared with MZCloud database and standard purchased compounds.

Example 13

Multielemental analysis was performed by ICP-MS-MS. Samples were acid digested with nitric acid to reduce the carbon load and to mineralize all compounds associated with the elements of interest. Digested samples (1-5 mg) were diluted with ultra-pure water to reduce the acid concentration below 3% and loaded into the ICP-MS-MS (triple quad Agilent 8800x ICP-MS-MS). The instrumental conditions were optimized to remove interferences by using a collision/reaction cell[73]. Integration time was adjusted according to the concentration range for each particular element. Multiple isotopes were monitored when possible to ensure that no interferences were present. The external calibration method was used from 0.01 ng $mL^{-1}$ to 2500 ng $mL^{-1}$ for the elements of interest. A mixture of scandium, yttrium, indium and bismuth was spiked to the samples and calibration as internal standards at 5 ng $mL^{-1}$ to correct for sensitivity drifts. In order to increase the accuracy, internal mass index elemental tags were used in the form of P and S instead of the sample mass. The data analysis was performed with Agilent MassHunter software, with internal standard recoveries and calibration curves. The results are expressed in ng of element per gram of sample. Quality control samples used include NIST SRM 2668-Toxic Elements in Frozen Human Urine standard reference material and the NIST Bovine muscle powder SRM 8414.

SEC-ICP-MS analysis was performed in the tissues after protein extraction under non-denaturing conditions. For this, 5-10 mg of tissue were homogenized in an ice-cold agate mortar and pestle with 0.5 mL of a protein extracting solution containing 50 mM sodium dodecyl sulfate, 10 mM sodium chloride, 50 mM Tris-HCl and an EDTA-free protease inhibitor (Pierce, USA) at pH 7.4. In order to increase the extraction efficiency, an ultra-sonication probe was used with 3, 1 second pulses with 3 seconds rest in between at 20% extrusion. Debris were filtered out in a 0.45 μm pore size spin filter with nylon membrane at 10,000 g for 5 minutes at 4° C. 100 μL of the filtered solution were injected to an Agilent 1200 HPLC system composed by a thermostated auto sampler set to 4° C., a vacuum membrane degasser, a binary pump, a column oven compartment and a UV-Vis diode arrange detector. The SEC column was a TSK Gel 3000SW 7.8×30 mm, 10 μm particle size; with 50 mM Ammonium acetate buffer in 0.1% methanol at pH 7.4 as mobile phase at 0.5 mL $min^{-1}$. The outlet of the HPLC system was connected to the ICP-MS-MS nebulizer by a 65 cm PEEK capillary of 0.17 mm of internal diameter. The ICP-MS was operated in time resolved analysis with an integration time of 0.1 s per isotope.

Arsenic speciation analysis was performed with an Agilent 1200 HPLC system composed by a thermostated auto sampler set to 4° C., a vacuum membrane degasser, a binary pump and a column oven compartment. An anion exchange separation column (PRP-X100, 250×4.1 mm, 10 μm, Hamilton, Switzerland) and a guard column (PRP-X100 20×2 mm, 10 μm, Hamilton) were used. The elution was performed isocratically at a flow rate of 1.0 mL $min^{-1}$. The mobile phase was transported from the separation column to the nebulizer of the ICP-MS-MS by a PEEK capillary of 65 cm and 0.17 mm of internal diameter. 100 μL of the homogenized tissue were extracted for As compounds with 10 mM $(NH_4)_2HPO_4$, and 30 mmol $L^{-1}$ $HNO_3$. The samples were vortexed for one minute and, then heated at 100° C. for 30 min in a heating block. After cooling, the extracts were centrifuged (3000 rpm for 5 min), and 50 μL of the supernatant and 200 μL of mobile phase were mixed into polyethylene vessels, filtered in a 0.45 μm spin filter nylon membrane at 5,000 g for 5 minutes, and 100 μL of the supernatant was transferred to HPLC vessels for analysis.

All documents cited are incorporated herein by reference; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of."

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. A method of diagnosing an elevated risk of recurrence of clear cell renal cell carcinoma in a subject and treating the subject for clear cell renal cell carcinoma, comprising:

a. detecting and quantifying total copper content and Cu-COX complex in a sample of kidney tumor tissue or kidney tumor biopsy from said subject;

b. diagnosing an elevated risk of recurrence of clear cell renal cell carcinoma for a subject with:

i. a level of Cu-COX complex identified at a molecular mass range between 500 kDa-250 kDa is higher than 0.45 ng $g^{-1}$ expressed as copper concentration; or ii. the copper content at a molecular mass fraction between 500 kDa-250 kDa is ≥20% of the total copper in the sample; and c. treating the subject diagnosed with an elevated risk of recurrence of clear cell renal cell carcinoma by administering a therapeutically effective amount of mitochondrial respiratory complex inhibitors, angiogenic inhibitors, inhibitors of the mTOR pathway, immune checkpoint inhibitors, mitoriboscins, inhibitors of mitoribosomes or combinations thereof to the subject.

2. The method of claim 1 wherein an elevated risk of recurrence of clear cell renal cell carcinoma is diagnosed for a level of total copper in the sample that is higher than 4.5 ng $g^{-1}$ expressed as total copper concentration.

3. The method of claim 1 wherein the Cu-COX complex is detected using SEC-UV-Vis-ICP-MS.

4. A method of diagnosing an elevated risk of recurrence of clear cell renal cell carcinoma in a subject and treating the subject for clear cell renal cell carcinoma, comprising:

a. detecting and quantifying total copper content and Cu-COX complex in a sample of kidney tumor tissue or kidney tumor biopsy from said subject;

b. diagnosing an elevated risk of recurrence of clear cell renal cell carcinoma for a subject with:

i. a level of Cu-COX complex identified at a molecular mass range between 500 kDa-250 kDa is higher than 0.45 ng $g^{-1}$ expressed as copper concentration; or ii. the copper content at a molecular mass fraction between 500 kDa-250 kDa is ≥20% of the total copper in the sample; and c. treating the subject diagnosed with an elevated risk of recurrence of clear cell renal cell carcinoma by administering a therapeutically effective amount of biguanides, metformin, phenformin, BAY-872243, IACS-010759, dihydroorotate dehydrogenase inhibitors, leflunomide, brequuinar, teriflunomide or combinations thereof to the subject.

5. The method of claim 4 wherein an elevated risk of recurrence of clear cell renal cell carcinoma is diagnosed for a level of total copper in the sample that is higher than 4.5 ng $g^{-1}$ expressed as total copper concentration.

6. The method of claim 4 wherein the Cu-COX complex is detected using SEC-UV-Vis-ICP-MS.

7. A method of diagnosing an elevated risk of recurrence of clear cell renal cell carcinoma in a subject and treating the subject for clear cell renal cell carcinoma, comprising:

a. detecting and quantifying total copper content and Cu-COX complex in a sample of kidney tumor tissue or kidney tumor biopsy from said subject;

b. diagnosing an elevated risk of recurrence of clear cell renal cell carcinoma for a subject with:

i. a level of Cu-COX complex identified at a molecular mass range between 500 kDa-250 kDa is higher than 0.45 ng $g^{-1}$ expressed as copper concentration; or ii. the copper content at a molecular mass fraction between 500 kDa-250 kDa is ≥20% of the total copper in the sample; and c. treating the subject diagnosed with an elevated risk of recurrence of clear cell renal cell carcinoma by administering a therapeutically effective amount of copper chelators selected from the group consisting of D-penicillamine: (S)-2-amino-3-mercapto-3-methylbutanoic acid (DPA), Tetrathiomolybdate (TM), Trientine: triethylenetetramine dihydrochloride (TETA), 5,7-Dichloro-2 [(dimethylamino) methyl] quinolin-8-ol (PBT2), 2,3-Dimercaptosuccinic acid (DMSA) and combinations thereof to the subject.

8. The method of claim 7 wherein an elevated risk of recurrence of clear cell renal cell carcinoma is diagnosed for a level of total copper in the sample that is higher than 4.5 ng $g^{-1}$ expressed as total copper concentration.

9. The method of claim 7 wherein the Cu-COX complex is detected using SEC-UV-Vis-ICP-MS.

* * * * *

SEQUENCE LISTING

```
<160> NUMBER OF SEQ ID NOS: 23

<210> SEQ ID NO 1
<211> LENGTH: 646
<212> TYPE: DNA
<213> ORGANISM: Homo sapiens

<400> SEQUENCE: 1

aggacacgtg ggtgggggaa gctgagcgct gagaccaagg gctaaagctg ggaggtgagt      60

ctgtcacctt gagccgggcg agcgctgtgg gccaagcagg ggttgcaggg tagtaggagt     120

gcagactgaa aaaatgcaga ccgccggggc attattcatt tctccagctc tgatccgctg     180

ttgtaccagg ggtctaatca ggcctgtgtc tgcctccttc ttgaatagcc cagtgaattc     240

atctaaacag ccttcctaca gcaacttccc actccaggtg gccagacggg agttccagac     300

cagtgttgtc tcccgggaca ttgacacagc agccaagttt attggtgctg ggcagccac      360
```

```
agttggtgtg gctggttcag ggctggcat tggaaccgtg tttggcagct tgatcattgg    420

ctatgccagg aacccgtctc tcaagcagca gctcttctcc tatgccattc ttggctttgc    480

cctgtctgag gccatggggc ttttctgttt gatggtcgcc ttcctcatcc tcttcgccat    540

gtgaggctcc atgggggggt caccggcctg ttgctactgc aactccacac cattcttggt    600

gctggggtgt gttaagcttt accattaaac acaacgtttc tctaaa                   646
```

```
<210> SEQ ID NO 2
<211> LENGTH: 756
<212> TYPE: DNA
<213> ORGANISM: Homo sapiens

<400> SEQUENCE: 2

gcagtccacg ttacggatcg gcttactccg cggagttggc ctcatttctg cagtcggcgc     60

tccctgtagt ttctcctctc gaacgccagg tggagcaacc ggccggatac cgccacagcc    120

ctggcaggcg gcgctgtgat gcctgagctg atcctctctc ctgccacagc tcctcacccc    180

ctgaaaatgt tcgcctgctc caagtttgtc tccactccct ccttggtcaa gagcacctca    240

cagctgctga gccgtccgct atctgcagtg gtgctgaaac gaccggagat actgacagat    300

gagagcctca gcagcttggc agtctcatgt ccccttacct cacttgtctc tagccgcagc    360

ttccaaacca gcgccatttc aagggacatc gacacagcag ccaagttcat tggagctggg    420

gctgccacag ttggggtggc tggttctggg gctgggattg gaactgtgtt tgggagcctc    480

atcattggtt atgccaggaa cccttctctg aagcaacagc tcttctccta cgccattctg    540

ggctttgccc tctcggaggc catggggctc ttttgtctga tggtagcctt tctcatcctc    600

tttgccatgt gaaggagccg tctccacctc ccatagttct cccgcgtctg gttggccccg    660

tgtgttcctt ttcctatacc tccccaggca gcctggggaa cgtggttggc tcagggtttg    720

acagagaaaa gacaaataaa tactgtatta ataaga                              756
```

```
<210> SEQ ID NO 3
<211> LENGTH: 780
<212> TYPE: DNA
<213> ORGANISM: Homo sapiens

<400> SEQUENCE: 3

accgcgaagg gaggagtggc aacatggcgt cttcgggagc tggtgaccct ctggattcta     60

agcgtggaga ggccccgttc gctcagcgta tcgacccgac tcgggagaag ctgacacccg    120

agcaactgca ttccatgcgg caggcggagc ttgcccagtg gcagaaggtc ctaccacggc    180

ggcgaacccg gaacatcgtg accggcctag gcatcggggc cctggtgttg gctatttatg    240

gttacacctt ctactcgatt tcccaggagc gtttcctaga tgagctagaa gacgaggcca    300

aagctgcccg agcccgagct ctggcaaggg cgtcagggtc ctaatctgga tgggtattga    360

tcatgtccaa cctgctggag ccccttcaca tggtggatga tgccccatga ccctgtagaa    420

attgaatcct gctcacaaca ttgttggcct tcttactaac cttggaccgt gattgagccc    480

aagaaaccag ggacttacgc atttggccaa tgtcaaaaga acagaacttt gcccactgca    540

cacttgctgt gtacaatgac tgagcccttt cttgtagttt gtttccttgt ttgagaggtg    600

tgcatgcgac cgtggctttt cccaaagttt ctgactttgt ggtttacccc cttcaccttc    660

cagggacgca gttgttacga ggttagacgt ggcagctctg tgcagtgttt gagcctacag    720

tgggatacat agggtcaaat tgagaataat aaactgagtc attctcctgg agtcaagtga    780
```

<210> SEQ ID NO 4
<211> LENGTH: 5496
<212> TYPE: DNA
<213> ORGANISM: Homo sapiens

<400> SEQUENCE: 4

```
gtcaccgagt cgttggcgct gtcatggcgg gtgtgctgaa gaagaccact ggccttgtgg     60
gattggctgt gtgcaatact cctcacgaga ggctaagaat attgtacaca aagattcttg    120
atgttcttga ggaaatccct aaaaatgcag catatagaaa gtatacagaa cagattacaa    180
atgagaagct ggctatggtt aaagcggaac cagatgttaa aaaattagaa gaccaacttc    240
aaggcggtca attagaagag gtgattcttc aggctgaaca tgaactaaat ctggcaagaa    300
aaatgaggga atggaaacta tgggagccat tagtggaaga gcctcctgcc gatcagtgga    360
aatggccaat ataattatta agtgactttg gtgtgttcat gggaaactga tgtaattaaa    420
tattctgtta tattaagagc gtgttcttat tactgacatt ttgtaatcaa gaaaagtgat    480
atagaaaata tgtaggagac tgttaaaatt ggtgattatg gtaatatggt catgtgaatc    540
aatttttgat ttataaagta ctcacacaag ttgtttcaaa gatgatattt ctgtgaacag    600
agaggccatg ggaagatttg aaaattatta aagaaaaatt cctacagatt ttcaatgcag    660
agaccataat caaaaagtaa actttcttta gtagtatgtt caatacatca tttaattttt    720
taagttatcc tgaagaagga aaggtcctta attattatag tctaaacaaa tttatagatt    780
actgtttgaa gtaaataata cgagtgaata ttttcaaatg tgataaaata gcacaagtgg    840
ctggtgataa aatttgaaat tatggttaac ctcagctgtg atcttatgta tgtaaagtga    900
aatttaaata gataattata ggttgattac aaaatccata gtgtcatttt attttagtca    960
ttattgaatt ataccattta ctctgttttc ttatagtctt aattttatta tattttgttg   1020
ttactgtatt atatttgaaa accttcaaat tagaatacat tgtacagtta aagaaattga   1080
cttggtactt aaaagaaaga tttcccattg catacaggtt attggagaaa ttttcctttt   1140
gttgcatttg tggaagttag ttttctggcc cgtggccttt aattttctta atcaacctaa   1200
ttacatcagg atagaggtag agtttctgta aaagaagaga cattaagagt tcctgaaatt   1260
tatatctggc atacggatag gcttatattc aaaacatctt agtcatacga ccataaatta   1320
aaagtggagt cactaaatag tttgcagtac gtttctaata taagtgtagg tgggtatcaa   1380
aacaagacaa atgctgttca gggaaagaag ttggcaagct taaggttaaa caaaaataaa   1440
attacatgtg ttttcgcctt cctagctccc tgtcattcct aaatacttgg ttaaatttaa   1500
cgtggtatct ctttccttca tagatagtac tatactcttg tggggttttg tgtatacgtg   1560
tgtgtgtgtg tgtgtgtgtg tgtgtgtgtg tgtgtgtgtg tgcacgcgca tgcgcacatt   1620
tgctcagaat gagaaaaaaa tggtattttt ccttctttcc agtatatttc tcccctcata   1680
gagctgtaac atgaatacta aataaatatt aaataaggtg gattcttaga ggttagagtg   1740
caagaaggct ccttctggtg gggaagtgtt agagggggag ttagaagccc agggtttctc   1800
attctcatgg ttctagtgtt gttaactcaa tgactacatt gaggcaagtt tggcctgttt   1860
ctcagaatgg cctatttcta atgctgcaaa agaaatagaa tatgatttat aacaacattt   1920
tcagttctaa acatttcttg aatatataat atatttatta aaacatgatg ctgaagtgtg   1980
tttgcatggg tactttcaag gtaattttct agccaaccat tatttttcag gtcctttgga   2040
caacacagaa acaaagatgg cttgctgtgt ttttgtcata ttttcagtcc cgtatctgcc   2100
atgattcttg ggcatctttt atgtttcacc aacagtgtta ctgaactttt ttgctaaaag   2160
```

```
gggaccttac tggtgtttgc attagaaatg ctagttgcag aataatagtc attgtaaaaa   2220
taatattata acaataatag ctaatgtttg ttgagacttt aatatgaatg tcaggcacta   2280
tcataagtac ctgactaatt tcactcatta aacctgcact acaaccctaa gagtgatact   2340
acaaattatc ttcattttcc agataagaaa ccagaaccct acgtgagtag ttttcccctg   2400
caattatgca acttggggcc ttggggacac tgaaaccaag agatgattta ataacaaatc   2460
caaggtcaca tagctagtaa gatgtgaagc tgaagtttga acccaggcag tctggttcta   2520
gaactgatgc tcctgttata ttattattta tgaatatgct tgggatgttg tgacttcttc   2580
ctgtgctgta tgggctgtac caaatgaaac tagatcctgc tctctttacc ttttctgtca   2640
aaattatctg taaagaacaa atatgagcag aagtagtaaa cgatttcatt ttctgcaaag   2700
agctgcatat aggttatagg cagattatgt taatgggata ggtatctaaa aggtattgca   2760
atttggtcat tggttctttc tcctgtctca attgctcaca gaactttaca cctgatcgtt   2820
tttactcctt cagtcttttc ccagttgctt cctataaaca tccaggttaa gtctcctgat   2880
cactttgcaa atgattcttt tattcagaga tcttcagtgt tttgagtggc tactaaacta   2940
attttaataa ttttcagaat ggcctatttc agttctccca tgggtttcat tctagttaat   3000
catcatactg cagatacttc aaaagaaaga gaagctaatc aatttgagct ttgctaagaa   3060
agaagaaatg gcaacaaagt tgatgccccc tttctcccac actgggactt agtgcagacg   3120
attccaattt cttggcattc tttcctttgg gatgaaaatg gcttatattt aggataacta   3180
taggataatt tatcattcca cttggaatga ttttgagtga aaataattac ataaggataa   3240
cagatgtaca ccatgactgt cctgggcaaa caagatatag gggggcaccc tactggagta   3300
aggctcaggt ctcaaggttg ccatctttcc cacaccagta ggatcaacta gtctgtcatt   3360
ggaatagaat gaattgatgc cagcagtagt agtcatcatg tgcaatcagg cctcaagttt   3420
tattgtatcc tttcactctc cctcattctc ccctccccct ccttttccct cagaattggg   3480
ggatggaaga aaagagagct tatattttat tgtcaatttt ctaatcacat tcagaggagc   3540
gaagctaatt aagccaataa caatgtttat gaatgtatct tttttaaaag ggagatgaca   3600
atatatagga aaattcccac atgtaggcta atagcagctt tttctttttc ctcccatcct   3660
ctatgattat gtaaacatac agaagtctaa caccctacac aagtgtattg tggggtatgg   3720
gattaagtac caaattgctg aacatatcac tagtattttg gatttgctga gtgcagtctt   3780
cccattaaaa ctaagtgttc agtagggagg cgtggtggct cacacctata atcccactac   3840
tttgggaggc cgaggtgggt ggatcacttg aggtcaaaag ttcgaggcca gcctggccaa   3900
tatggtgaaa ccccgtctct actaaaaaca aaaacaaaaa ctaagtgttc agtgagattg   3960
tagcctatgc tacaacaata gtaatgccaa ttgttttaga gaaaagtaaa tgagaggcta   4020
ccagttgtgt ttagaggagg tcgacgtttt attttagaca aaattcacag gaaatcacag   4080
tgggaatgtg ataaggggtt tgaatgattg atggggacag gaagaattca tttgagagac   4140
tagagatgag tcagtattct agatcgtgaa gtaaaatagt gagtcatgta gtgacttagc   4200
atgggttatc cttaaatccc agtgtcttaa gtgtattttt tattcatact gcatgtctaa   4260
ggagggttgg caaggagtgc tcatagaccc acaaggaatc caggctgagt gtggcaccat   4320
caacatatat ttccatgacc atagtggtgg tggggaattg gaacatggta aattacacat   4380
aggaataaaa aaaaagaaac aaccaaggtt aaattttttt ttgactgtgc cacaaaattt   4440
atgaattgaa cttgccatgc atcactaata attttcaaat tggtctttag gtttacatta   4500
```

```
gcagctaatt ttttgtggta cacttaaatg taatttatga ttggcatctg tatataatta   4560

aatgaaaagc attgcaaaga tttctatttt ggtatttctc atgatcttca attttttttt   4620

aggtgaatct attaggtttt ctaaagataa ctattttttt ttttttacaa aatattggca   4680

ttttaatctc tctataactg gagggtgaat tatttttcac cagagtaaaa caggtccaaa   4740

gtcccttatc taaattccta atttcaaaaa tctctgaaaa caaagttttt tcataactca   4800

tttggcaaca aaccccacct gaattacatg aggctatttg tggtatttat cgcacttcaa   4860

tgtgaatatg aatatatttt gccacagatg tatcaatata tttgattcta aactgcttcc   4920

tcagaccctc ttaatgtgtt acataatgta aagtatatgc ccatatttcc tttcaaaaat   4980

ctgaaaaatt gtgaatatca aacacatctg tcttaaaagg tttcagaaaa gggacaatag   5040

acctatattt ccattctctt aacaagttca caaagtggta ttatgatcca aatttaatct   5100

aaataatttc caaaacaaaa attttcaggt ccttagtttt ctaaattatt ttaatattaa   5160

aaatattcat tattcatttt aacctgtagt aacaacagga gatactttga aatgcttgat   5220

tttatcaagc cactaggtgg catctttgta aaaataaaag cacatcaaaa gaaatgttta   5280

ttacataaat aaatgctgag atgaataaag gtagatgttt catgagaaat acgaagtcgt   5340

ttggtggaat aaatcctgag aaaatgcata gatttatcat gaaaaggaaa atggaaaatg   5400

gtattgtaaa attactcttt cacttttgga attgagaagc tttttcctat tggttgtttt   5460

cattaagttt gaatataaat ttattatgta accaaa                             5496
```

<210> SEQ ID NO 5
<211> LENGTH: 665
<212> TYPE: DNA
<213> ORGANISM: Homo sapiens

<400> SEQUENCE: 5

```
gcagtgcatc ctgggttggc gtagccatgg cgtctcgtgt cctttcagcc tatgtcagcc     60

gcctgcccgc ggcctttgcg ccgctgcccc gggtccggat gctggccgtg gcccggcctc    120

tcagcaccgc tctctgctcc gcggggaccc agacgaggct cgggactttg cagccggcct    180

tagtgctcgc gcaggttcct ggtagagtta cacagttgtg ccgccagtat agcgacatgc    240

ctcctttgac gttagagggc atccaggacc gtgttcttta cgtattgaaa ctctatgaca    300

agattgaccc agagaagctt tcagtaaatt ctcattttat gaaagacctg ggcttagaca    360

gtttggacca agtggagatt atcatggcca tggaagacga atttgggttt gaaattcctg    420

atatagatgc tgaaaagtta atgtgtccac aagaaattgt agattacatt gcagataaga    480

aggatgtata tgaataaagt atcagaccct ttggctttgc tgagagagga ctcagatgat    540

agtgacgaat gtctggcagt gaggacacat tttggcattc ttgctgactc tgacagagtg    600

attctgatgg acttgtattt aaattgtatg tgttttactc tttgaaaata aatctataaa    660

accaa                                                                665
```

<210> SEQ ID NO 6
<211> LENGTH: 902
<212> TYPE: DNA
<213> ORGANISM: Homo sapiens

<400> SEQUENCE: 6

```
gacttcgccg cgcgttggtc agccatggcc accgctctcg cgctacgtag cttgtaccga     60

gcgcgaccct cgctgcgctg tccgcccgtt gagcttccct gggccccgcg gcgagggcat    120

cggctctcgc cggcggatga cgagctgtat cagcggacgc gcatctctct gctgcaacgc    180
```

```
gaggccgctc aggcaatgta catcgacagc tacaacagcc gcggcttcat gataaacgga    240

aaccgcgtgc tcggcccctg cgctctgctc ccgcactcgg tggtgcagtg gaacgtggga    300

tcccaccagg acatcaccga agacagcttt tccctcttct ggttgctgga gccccggata    360

gagatcgtgg tggtggggac tggagaccgg accgagaggc tgcagtccca ggtgcttcaa    420

gccatgaggc agcggggcat tgctgtggaa gtgcaggaca cgcccaatgc ctgtgccacc    480

ttcaacttcc tgtgtcatga aggccgagta actggagctg ctctcatccc tccaccagga    540

gggacttcac ttacatcttt gggccaagct gctcaatgaa ccgccaggaa ctgacctgct    600

gactgcactc tgccaggctt cccaatgctt tcactcttat ctaccctttg gcacttatct    660

tgcttatcaa cataataatt tatacacttc tcccattttg tatcaggtgt gttgctggcc    720

aggagctgat ggctcactgg gctcttggag gggaatgtga agaaaccaag gagtcacttt    780

ttcatctaga ttacttagga ttccttgact tttcagaagt cgggaagcag tatgtttgcc    840

tgttgtagac ctacttgctc acatgcagat ttgagaggac ctcaacggct tttctcacaa    900

aa                                                                   902
```

```
<210> SEQ ID NO 7
<211> LENGTH: 894
<212> TYPE: DNA
<213> ORGANISM: Homo sapiens

<400> SEQUENCE: 7

agtctgcatc tgagtaacat ggcggcggcg gcggtagcca ggctgtggtg gcgcgggatc     60

ttgggggcct cggcgctgac cagggggact gggcgaccct ccgttctgtt gctgccggtg    120

aggcgggaga gcgccggggc cgacacgcgc cccactgtca gaccacggaa tgatgtggcc    180

cacaagcagc tctcagcttt tggagagtat gtggctgaaa tcttgcccaa gtatgtccaa    240

caagttcagg tgtcctgctt caatgagtta gaggtctgta tccatcctga tggcgtcatc    300

ccagtgctga ctttcctcag ggatcacacc aatgcacagt tcaaatctct ggttgacttg    360

acagcagtgg acgtcccaac tcggcaaaac cgttttgaga ttgtctacaa cctgttgtct    420

ctgcgcttca actcacggat ccgtgtgaag acctacacag atgagctgac gcccattgag    480

tctgctgtct ctgtgttcaa ggcagccaac tggtatgaaa gggagatctg ggacatgttt    540

ggagtcttct ttgctaacca ccctgatcta agaaggatcc tgacagatta tggcttcgag    600

ggacatcctt tccggaaaga ctttcctcta tctggctatg ttgagttacg ttatgatgat    660

gaagtgaagc gggtggtggc agagccggtg gagttggccc aagagttccg caaatttgac    720

ctgaacagcc cctgggaggc tttcccagtc tatcgccaac cccggagag tctcaagctt     780

gaagccggag acaagaagcc tgatgccaag tagctccagg gaacgcatgt ggatcctaga    840

cagcgcctta tctatgattg agtgtccgtg taaataaatt cctacttaga ctta          894
```

```
<210> SEQ ID NO 8
<211> LENGTH: 1595
<212> TYPE: DNA
<213> ORGANISM: Homo sapiens

<400> SEQUENCE: 8

gcaacagggc cgactgcagc tggaagatgg cggcgtccgt ggtctgtcgg gccgctaccg     60

ccggggcaca agtgctattg cgcgcccgcc gctcgccggc cctgctgcgg acgccagcct    120

tgcggagtac ggcaaccttc gctcaggcgc tccagttcgt gccggagacg caggttagcc    180
```

```
tgctggacaa cggcctgcgt gtggcctccg agcagtcctc tcagcccact tgcacggtgg    240

gagtgtggat tgatgttggc agccgttttg agactgagaa gaataatggg gcaggctact    300

ttttggagca tctggctttc aagggaacaa agaatcggcc tggcagtgcc ctggagaagg    360

aggtggagag catgggggcc catcttaatg cctacagcac ccgggagcac acagcttact    420

acatcaaggc gctgtccaag gatctgccga aagctgtgga gctcctgggt gacattgtgc    480

agaactgtag tctggaagac tcacagattg agaaggaacg tgatgtgatc ctgcgggaga    540

tgcaggagaa tgatgcatct atgcgagatg tggtctttaa ctacctgcat gccacagcat    600

tccagggcac acctctagcc caggctgtgg aggggcccag tgagaatgtc aggaagctgt    660

ctcgtgcaga cttgaccgag tacctcagca cacattacaa ggcccctcga atggtgctgg    720

cagcagctgg aggagtggag caccagcaac tgttagacct cgcccagaag cacctcggtg    780

gcatcccatg gacatatgca gaggacgctg tgcccactct tactccatgc cgcttcactg    840

gcagtgagat ccgccaccgt gatgatgctc taccttttgc ccacgtggcc attgcagtag    900

agggtcctgg ctgggccagc ccggacaatg tggccttgca agtggccaat gccatcatcg    960

gccactatga ctgcacttat ggtggtggcg tgcacctgtc cagcccactg gcttcaggtg   1020

ctgtggccaa caagctatgc cagagtttcc agaccttcag catctgctat gcagagacgg   1080

gcttgctggg tgcacacttt gtctgtgacc gaatgaaaat cgatgacatg atgttcgtcc   1140

tgcaagggca gtggatgcgc ctgtgtacca gtgccacgga gagtgaggtg gcccggggca   1200

aaaacatcct cagaaatgcc ctggtatctc atctagatgg cactactcct gtgtgtgagg   1260

acatcggacg cagcctcctg acctatggcc gccgcatccc cctggctgaa tgggaaagcc   1320

ggattgcgga ggtggatgcc agtgtggtac gtgagatctg ctccaagtac atctatgacc   1380

agtgcccagc agtggctgga tatggcccca ttgagcagct cccagactac aaccggatcc   1440

gtagcggcat gttctggctg cgcttctagg cgggaagcct atgtaagcaa gagggcaggg   1500

ccggggtttg tggtcccccc cccaccacaa acacagcact tcggctcctc taacctgtgc   1560

cacaggtgac caccaataaa atcctctgct gagaa                              1595
```

<210> SEQ ID NO 9
<211> LENGTH: 1009
<212> TYPE: DNA
<213> ORGANISM: Homo sapiens

<400> SEQUENCE: 9

```
gtcatttccg gctcgaatgc ccggcagccg tggcggctag agcgttcctc cccagctcga     60

atgcccggcg gccgaggcgg ctagagcgtc gcctcctccc ggggaaccgc gtgtgacctt    120

ccagcccgcg gaccgatgct gccggcggcc gctcgccccc tgtgggggcc ttgccttggg    180

cttcgggccg ctgcgttccg ccttgccagg cgacaggtgc catgtgtctg tgccgtgcga    240

catatgagga gcagcggcca tcagaggtgt gaggccctcg ctggtgcacc cctggataac    300

gcccccaagg agtacccccc caagatacag cagctggtcc aggacatcgc cagcctcact    360

ctcttggaaa tctcagacct caacgagctc ctgaagaaaa cgttgaagat ccaggatgtc    420

gggcttgtgc cgatgggtgg tgtgatgtct ggggctgtcc ctgctgcagc agcccaggag    480

gcggtggaag aagatatccc catagcgaaa gaacggacac atttcaccgt ccgcctgacc    540

gaggcgaagc ccgtggacaa agtgaagctg atcaaggaaa tcaagaacta catccaaggc    600

atcaacctcg tccaggcaaa gaagctggtg gagtccctgc cccaggaaat caaagccaat    660

gtcgccaaag ctgaggcgga gaagatcaag gcggccctgg aggcggtggg cggcaccgtg    720
```

```
gttctggagt agcctccagc tcggaggact tgtgttcagg ggtcctgggc cccgggcgag     780

gtcccgccct cccgtggtca ctggctccgc ccccagcacc aggcgcccag tggagccgtt     840

tgggagaatt gcctgcgcca cgcagcgggg ccggacaggc cgcacagacc tactgtggcg     900

ggagggaggg gcggctgctg cctggtgacg gcacccggag gcccaccagg acgcgccacc     960

ggtgaatgtg cctctggtgg ctgctgagaa aaatacactg tgcagctca               1009
```

<210> SEQ ID NO 10
<211> LENGTH: 957
<212> TYPE: DNA
<213> ORGANISM: Homo sapiens

<400> SEQUENCE: 10

```
gtccgccggg ctgggcctgg cgcgcaggcg ctaggaagag gccgcgtggg gcgaaggcgg      60

cgcttggctg gtggggcccg cggcgggatt ttcccgggcg gcgagagcgg atctatcttg     120

ggatcccatg gctttcttta ctgggctctg gggccccttc acctgtgtaa gcagagtgct     180

gagccatcac tgtttcagca ccactgggag tctgagtgcg attcagaaga tgacgcgggt     240

acgagtggtg gacaacagtg ccctggggaa cagcccatac catcgggctc ctcgctgcat     300

ccatgtctat aagaagaatg gagtgggcaa ggtgggcgac cagatactac tggccatcaa     360

gggacagaag aaaaaggcgc tcattgtggg gcactgcatg cctggccccc gaatgacccc     420

cagattcgac tccaacaacg tggtcctcat tgaggacaac gggaaccctg tggggacacg     480

aattaagaca cccatcccca ccagcctgcg caagcgggaa ggcgagtatt ccaaggtgct     540

ggccattgct cagaactttg tgtgagttga gcccaggcct ctggttgcag gactcgtgaa     600

tggagcagtt ctgagaacca cccttttgct aagggagctt gggagccaca tggctgctcc     660

cttcacactg ggtaacagtg tagtatcctg tgagagaata aatgtattca tttatgtgtt     720

tttccagagc tttctgggat gtgggaaaat aaattacact gaagcagttg aaaggtggct     780

tacccgagtc tggccacacg ggtagcatt  ctttacatgg agcagccttg gtgccagggt     840

ctgagccctt gcttttctgg tttggaccct ataagttcat ccaggactgt caggccctgg     900

aaaactgagg tacacaccaa atgccaattt ataaatgtac catggctcta accaaaa       957
```

<210> SEQ ID NO 11
<211> LENGTH: 1358
<212> TYPE: DNA
<213> ORGANISM: Homo sapiens

<400> SEQUENCE: 11

```
ggagggaaga tggcggcgcc ctggtggcga gccgcgctgt gcgagtgtcg gagatggcgg      60

ggcttcagca cctcggccgt cctgggccgc cggacacccc cgctggggcc gatgcccaac     120

agtgacatcg acttgagcaa cctggagcgg ctggagaagt accggagctt cgaccgctac     180

cggcgccgag cagagcagga ggcgcaggcc ccgcactggt ggcggaccta ccgagagtat     240

ttcggggaga agacagatcc caaagagaag attgatattg ggctgcctcc acccaaagtc     300

tcccggaccc aacagctact ggaacggaaa caggccatcc aggagcttcg ggccaatgtg     360

gaagaggagc gggctgcccg cctccgcaca gccagtgtcc cgctggatgc cgtgcgggcc     420

gagtgggaga ggacctgtgg cccctaccac aagcagcgtc tggctgagta ttacggcctc     480

taccgagacc tgttccacgg tgccaccttt gtgccccgag tcccccctgca cgtggcctac     540

gctgtgggtg aggatgacct gatgcctgtg tactgtggca atgaggtgac tccaaccgag     600
```

-continued

```
gctgcccaag cgccagaggt gacctatgag gcagaagagg gctccttgtg gacgttgcta    660
ctcactagct tggatgggca cctgctggag ccagatgctg agtacctcca ctggctgcta    720
accaacatcc cgggtaaccg ggtggctgaa ggacaggtga cgtgtcccta cctccccccc    780
ttccctgccc gaggctccgg catccaccgt cttgccttcc tgctcttcaa gcaggaccag    840
ccgattgact tctctgagga cgcacgcccc tcaccctgct atcagctggc ccagcggacc    900
ttccgcactt ttgatttcta caagaaacac caagaaacca tgactccagc cggcttgtcc    960
ttcttccagt gccgctggga tgactccgtc acctacatct tccaccagct tctggacatg   1020
cgggagccgg tgtttgagtt cgtgcggccg ccccccttacc accccaagca gaagcgcttc   1080
ccccaccggc agcccctgcg ctacctggac cggtacaggg acagtcatga gcccacctat   1140
ggcatctact aaggagccag agtgtgcgca tttcagagca tgggattgat cggcagcaag   1200
agtaaagaca cagctccaga ggcccacact gtggggtctg ggccctgcct taggcagccc   1260
ccctctttgg ccccctcccg tcaggcccag ggcttggagt gaaagtgact ctcaggtggt   1320
ggggtgggga atgtgaataa acatgatttc ttgccggg                           1358
```

<210> SEQ ID NO 12
<211> LENGTH: 1354
<212> TYPE: DNA
<213> ORGANISM: Homo sapiens

<400> SEQUENCE: 12

```
agttatgcga aaacatggct gcggccggtt tggcccttct ttgtaggaga gtttcatccg     60
ccctgaaatc ttcccgatcg ttaataactc ctcaggtccc tgcctgcaca gggtttttttc   120
ttagtttgtt gcctaagagt acaccaaatg tgacatcctt tcaccaatat agattacttc    180
ataccacatt gtcaaggaaa ggactagaag aatttttttga tgacccaaaa aactgggggc   240
aagaaaaagt aaaatctgga gcagcatgga cctgtcagca actaaggaac aaaagtaatg    300
aagatttaca caaactttgg tatgtcttac tgaaagaaag aaacatgctt ctaaccctag    360
agcaggaggc caagcggcag agattgccaa tgccaagtcc agagcggtta gataaggtag    420
tagattccat ggatgcatta gataaagttg tccaggaaag agaagatgcc ctaaggcttc    480
ttcagactgg tcaagaaaga gctagacctg gtgcttggag aagagacatc tttggaagaa    540
tcatctggca caagttcaag cagtgggtta taccttggca cctaaataaa agatacaata    600
ggaaacgatt ctttgccttg ccttatgtgg accattttct cagactggaa cgtgagaaac    660
gagcccgcat caaagcacgg aaggaaaatt tagagagaaa gaaagcaaaa attcttttaa    720
aaaagtttcc acatcttgct gaagcccaaa agtcaagtct tgtctaagat gtctgaacta    780
ttaaatttac cattttgttt ttcttgaata gtctgtgtac aggagtaaat atgttaagtg    840
gtttataaag aaattctgtt tttagtcaag tgactttact aatcagttgt tctaagtgtg    900
aatatggcat gctaattagc taatttggta gaagctaatt tgcttctaaa aatcaggtat    960
aaagttcaga tgagattccc actttataaa ttctgacatt taagcaggct ttaaatgtca   1020
cctgctacct tagagtgtga aggtgatggt aactgccaca gcaaaggcaa taccgtagtt   1080
tttgaatttg aataatagtt ttacctctgt tgttaatagg ctatgaagag gatgtgggta   1140
ttgctgttaa taaacggagg actttgattc aaaataatga gaaatacatt tagtccttaa   1200
agtagtaatc acagtgcaca acagtccaaa atatatttct ggaatggcta atttttattt   1260
aattctgtaa gcctaaggta aaaagcatag gcagtaactt ttactagtca ataaaaagca   1320
gttctaccaa tccactggta attaatacac taaa                               1354
```

<210> SEQ ID NO 13
<211> LENGTH: 2100
<212> TYPE: DNA
<213> ORGANISM: Homo sapiens

<400> SEQUENCE: 13

```
gggaccggca agatggcggc gcggacagcg ttcggtgctg tgtgccggcg cctctggcag     60
ggattgggga atttttctgt aaacacttct aagggcaata cagccaaaaa tggtggcttg    120
cttctcagta ccaatatgaa gtgggtacag ttttcaaacc tacacgttga tgttccaaag    180
gatttgacca aacctgtggt aacaatctct gatgaaccag acatattata taagcgcctc    240
tcggttttgg tgaaaggtca cgataaggct gtattggaca gttatgaata ttttgctgtg    300
cttgctgcta aagaacttgg tatctctatt aaagtacatg aacctccaag gaaaatagag    360
cgatttactc ttctccaatc agtgcatatt tacaagaagc acagagttca gtatgaaatg    420
agaacacttt acagatgttt agagttagaa catctaactg gaagcacagc agatgtctac    480
ttggaatata ttcagcgaaa cttacctgaa ggggttgcca tggaagtaac aaagacacaa    540
ttagaacagt taccagaaca catcaaggag ccaatctggg aaacactatc agaagaaaaa    600
gaagaaagca agtcataaag cctcagggag gccatttttg cctaaatttg aaatgagggt    660
gggccagatg agtatgttta agtggagagt gcttccagct gagatgattt gagtctgccc    720
taactgctcc attgagttct cgtgccctca tcagctgagg gcagggaatg gaactttaat    780
ggaagaacca cttttatcta ttctttttat tcattgtttc agttctgatt tcagcaaaca    840
tgagcaaacc actttgactg aaagcagaaa gagtgaaaat tctattttgt tacgctactg    900
gtgttcaatt attagtttgt accattttta atttatgtca gttgatgcat ctgaaaataa    960
gtgcttggag tgttcgtacc cttatttttt tttaagattc ctagaaggaa tctttggtta   1020
attcagattg agcagttaaa gtttttgcta tttacctttg tgcaggctgg catatgctaa   1080
tttgggggtg gtaaccaacc gattttatct catgtaagca ttacattttg aagactgaat   1140
atacttcaca gcagatcaaa cacatttatg gcatgcactg acctcttctt ggagcccaga   1200
actttataga gttgcctacc agggttactg taatggaatt tatgatctta agaaattact   1260
agttgtatta tttatcctat gattcattca ttcaataagc ttttactgca taaactttac   1320
atccagcact gtagttaagt acccaaaatt gaatagaaat aatggctttt gaaaatcgca   1380
caaagcaggc caggcacggt ggctcacgcc tgtaatccca gcattttggg aggccgaggc   1440
aggcggatca cgaggtcaag agatccagac catcctggct aacacggtga aaccccgtct   1500
ctaataaaaa tacaaaaatt agctggacat ggtggcacgt gcctgtaatc ccagctactc   1560
aggaggctga ggcaggagaa ttgcgtgaac ccgggcccgg tggaggctgc agtgagacga   1620
gatcgcgcca ctgcactcca gcctggcgac agagcgagac gccgtctcaa aaaaaaaaaa   1680
agaaaattgt gcaaagcata ggtaaatatt tttctttatt aagcttctca ctgagaagcc   1740
ctctttattt tggtaaatgt cactctgttt gttaggagat gtctgctttt ccatgaaatg   1800
aaatagtggc taaagccctg aaagaggcaa gactacaatg ggctgaaaca gttggtatag   1860
caaccccaga gaagtgcttc attttctttt tatagtagaa gcaggtccat gtcttttgtg   1920
gtttcctgca catctttgga gtagttatga cttctcagtt tttccccccct taaactgcat   1980
tgcctattct tttttcctga catgctatca ggtatcagtg tgttgaatac atactgcttg   2040
tgtatcagac ttacgttact gtcatcacca ttaaaagaat tgcagctttg tgccccatga   2100
```

<210> SEQ ID NO 14
<211> LENGTH: 1163
<212> TYPE: DNA
<213> ORGANISM: Homo sapiens

<400> SEQUENCE: 14

```
aggtttttga agatggcggc cctcaaggct ctggtgtccg gctgtgggcg gcttctccgt     60
gggctactag cgggcccggc agcgaccagc tggtctcggc ttccagctcg cgggttcagg    120
gaagtggtgg agacccaaga agggaagaca actataattg aaggccgtat cacagcgact    180
cccaaggaga gtccaaatcc tcctaacccc tctggccagt gccccatctg ccgttggaac    240
ctgaagcaca agtataacta tgacgatgtt ctgctgctta gccagttcat ccggcctcat    300
ggaggcatgc tgccccgaaa gatcacaggc ctatgccagg aagaacaccg caagatcgag    360
gagtgtgtga agatggccca ccgagcaggt ctattaccaa atcacaggcc tcggcttcct    420
gaaggagttg ttccgaagag caaaccccaa ctcaaccggt acctgacgcg ctgggctcct    480
ggctccgtca agcccatcta caaaaaaggc ccccgctgga acagggtgcg catgcccgtg    540
gggtcacccc ttctgaggga caatgtctgc tactcaagaa caccttggaa gctgtatcac    600
tgacagagag cagtgcttcc agagttcctc ctgcacctgt gctggggagt aggaggccca    660
ctcacaagcc cttggccaca actatactcc tgtcccaccc caccacgatg gcctggtccc    720
tccaacatgc atggacaggg gacagtggga ctaacttcag taccettggc ctgcacagta    780
gcaatgctgg gagctagagg caggcagggc agttgggtcc cttgccagct gctatggggc    840
ttaggccatg ctcagtgctg gggacaggag ttttgcccaa cgcagtgtca taaactgggt    900
tcatgggctt acccattggg tgtgcgctca ctgcttggga agtgcagggg gtcctgggca    960
cattgccagc tgggtgctga gcattgagtc actgatctct tgtgatgggg ccaatgagtc   1020
aattgaattc atgggccaaa caggtcccat cctcttcatg acagctgtga gctccttact   1080
gtgggagagc tgcagggagc caaggtgggc tgcctgacac acttgccgct ctcgtgtgaa   1140
tccaagaaac tgcgttcctc aaa                                           1163
```

<210> SEQ ID NO 15
<211> LENGTH: 667
<212> TYPE: DNA
<213> ORGANISM: Homo sapiens

<400> SEQUENCE: 15

```
cccgcgctcc gcttggccca agatggcggc ctccgtgtgc agcgggttgc tggggccacg     60
ggtgctgtcc tggagccgag agctgccttg cgcttggcgc gccctgcaca cctccccggt    120
ctgcgccaag aaccgggcgg cccgagtacg cgtaagcaag gggacaagc cggtgaccta    180
cgaggaggca cacgcgccgc actacatcgc ccaccgtaaa ggctggctgt cgctgcacac    240
aggtaacctg gatggagagg accatgccgc agagcgaacg gtggaggatg ttttccttcg    300
caagttcatg tggggtacct tcccaggctg cctggctgac cagctggttt taaagcgccg    360
gggtaaccag ttggagatct gtgccgtggt cctgaggcag ttgtctccac acaagtacta    420
cttcctcgtg ggctacagtg aaactttgct gtcctacttt tacaaatgtc ctgtgcgact    480
ccacctccaa actgtgccct caaaggttgt gtataagtac ctctagaaca atccccttt    540
ttccatcaag ctgtagcctg cagagaatgg aaacgtggga aaggaatggt atgtggggga    600
aatgcatccc ctcagaggac tgaggcatag tctctcatct gctattgaat aaagaccttc    660
tatcttg                                                              667
```

<210> SEQ ID NO 16
<211> LENGTH: 1315
<212> TYPE: DNA
<213> ORGANISM: Homo sapiens

<400> SEQUENCE: 16

```
acagctgccc gggactccag tgatcgccgc ggctcgctcg cgccccggaa actgcccctt     60
ctcgggggtc atgatgggca gcaagatggc gtctgctagt agggtcgttc aggtagtcaa    120
accacacact ccattaataa ggtttcctga cagaagagac aatcctaaac ccaatgtatc    180
agaagctttg agatcagcag ggctaccatc tcactcttct gtaatttcac aacattctaa    240
aggaagtaaa tcaccagatt tgctgatgta tcagggtcca ccagacactg cagaaataat    300
aaaaacatta cctcagaaat acagaaggaa acttgtgtct caagaagaaa tggaatttat    360
ccaacgtgga ggtcctgaat aaccatggtg gctgctgttt gtcatcagac aatagaattg    420
tctttacaat aaaggacttc caaaatgaca gatgagaaac tgtatattaa acacctttaa    480
taaatattat gaaaaaaatg aaatatagaa aatttagatg gacacttgta tttcctaatt    540
tatgtatctt ggtcagcttc tccacaagct tacctaattg tttatatact ttatacttat    600
taaagtatac atttttaaat gttagcctat taatttactc ttgattatca aacattacca    660
gtgttgaact attaaaagca cacaatgtgt agtaaactat cataggattc ccataatttc    720
actttacttt ctgtttaggc atggaaaaat ttatcagtca gaattgctgt tttagggaca    780
tgattttcct gaaattgggt gaggatcagt gaaataatta ctctattact tgttcttaat    840
tctctgttct ctaatgtttt ttcattcaca agtttactgg agtataactg gcttagtaag    900
tatatcctac tctgaatgat aaaaatatag tcaagctaaa ataggtgact atactattaa    960
gatagagatc atacaaaaga ttccaaagaa agtcaaaaag tgtaaaatgg aaaataagag   1020
atcaaaatga atatagcata ggaataaaga tttcactaga aattgcaatt tattatgttt   1080
tggaggttgt aaggaagtct tgtttttttgg tttattttac tgttttgtga tcttgtatgc   1140
aaatcctgat aaccattaac cttctcaaac ttaatgtctg agagcctcat aaaatcaaca   1200
tatttactta ttaagcagtt tatgaaactt taatggggcc cctcctgtgc caagggtacg   1260
tatattgtga agtaaagcct cacaaagcta aataaattct cttccatacc tttaa        1315
```

<210> SEQ ID NO 17
<211> LENGTH: 3298
<212> TYPE: DNA
<213> ORGANISM: Homo sapiens

<400> SEQUENCE: 17

```
gcggctcgga ctccagcatg gcgaccgcgg tgcgcgctgt gggctgcctc cccgtgctgt     60
gtagcgggac ggcaggtcat ttattgggga ggcagtgttc cctaaacacc ttaccagcag    120
cttccatttt ggcatggaag agtgttctcg gcaatggcca tttgtcatca ctgggaacca    180
gagacaccca tccctacgcc agcttgagcc gtgcactgca gacacaatgc tgtatttctt    240
ctcccagtca cctgatgagc cagcagtata gaccatatag tttcttcact aaattgactg    300
cagatgagct gtggaaaggc gctttagcag agactggtgc tggagcaaaa aaaggaagag    360
gcaaaagaac taaaaagaag aaaagaaagg atctgaacag gggtcagatc attggtgaag    420
ggcgttatgg ttttctatgg cccggactga atgtccctct tatgaaaaat ggagcagtgc    480
agaccattgc ccaaagaagc aaggaagagc aggagaaggt ggaggcagac atgatccagc    540
```

-continued

```
agagagaaga gtgggaccga aagaagaaga tgaaggttaa acgggagcga ggatggagtg    600
gaaactcatg ggaggcatc agtcttggcc cccctgaccc tggtccctgt ggagaaacat     660
atgaggattt tgataccagg atacttgagg taagaaacgt tttcactatg actgcgaaag    720
agggaagaaa gaaatcgatc cgtgtcttgg tggctgtggg gaacggaaaa ggagctgcag    780
gtttttctat tgggaaagct actgatcgga tggatgcttt caggaaagca aagaacagag    840
cagttcacca tttgcattat atagaacgat atgaagacca tacaatattc catgatattt    900
cattaagatt taaaaggacg catatcaaga tgaagaaaca acccaaaggt tacggcctcc    960
gctgccacag ggccatcatc accatctgcc ggctcattgg catcaaagac atgtatgcca   1020
aggtctctgg gtccattaat atgctcagcc tcacccaggg cctcttccgt gggctctcca   1080
gacaggaaac ccatcaacag ctggctgata agaagggcct ccatgttgtg gaaatccggg   1140
aggaatgtgg ccctctgccc attgtggttg cgtcccccg ggggcccttg aggaaggatc    1200
cagagccaga agatgaggtt ccagacgtca aactggactg ggaagatgtg aagactgcac   1260
agggaatgaa gcgctctgtg tggtctaatt tgaagagagc cgccacgtaa cctctctggc   1320
cttgtgcagc cagttcctgt gctgccctgc acctaggaga gactcagccc ctcacagctt   1380
gggatgttac cttgcctttt gtttgttttg agggaagttt aatctttaaa ctctttggaa   1440
ataaataatt atagctttca tttgttgagc acatgttata tgccaatgtg atagaacctt   1500
tacatacata tctcagttca agactacttt aaatattcat ccaaagtaac aaaagtaaat   1560
gaattaggga gacggggtta ataatttgac ccaatcagta ataatgtaca caatgataat   1620
tgctgtagta attatagcta atatatatga actcattcat ccaaagtgaa tgtgattaac   1680
ttcattttac agagcagtta agtaacttga ctaccgtgag gaacttccaa accgttttcc   1740
acagtggaaa tggaagttgt aggctactat tgggaatgtt aaatggtata ttaattgtat   1800
accattgcaa ttttgacttg tatttccctg atggctgatg atgttgaaca tcttttcatg   1860
tgctgattgg ccatttgtat atgtttttttg gagaaatgtc tattcagagc ctttgcccat   1920
ttaaaaagtt atttttattt attattgagt tccttatagt ttctagatat aagcccccct   1980
atcatacatg ctttacagaa gtttttaccc attctgtgga atatatatat ttttatttct   2040
ttgcatactc tttctgcccc acccacatcc tctttctggg acactgatga ccaaaatgtt   2100
gaatctttta ctattgtccc gtgagtccct gaggcgctgt ttattttttt tccagtctgt   2160
tttctctgtg ttgctcagtt taggtaattt ctattgtttt atcttcagaa taactggtta   2220
tttactcttt cctttccatt ctgctcttga accatccatg cagtacttta actttgactg   2280
tcattgtata tttcagttaa aatttccatt tggtttattt tttatgtctt ctctttattt   2340
gctgaggcta tttgctgaga cttttttttt ctttaaatgg cttcaagagt gtttataatt   2400
gctcactgaa gcatttttat ggtggctgct ttaaaatctt tgtcatcagg taggtgtggt   2460
ggctcacgcc tataacccca gcactttgtg aaggtgaggc aggaggattg cttcagccca   2520
ggagtttgag atcagcctag gcaacaaagt gagacctcat ctctacaaaa agtaaaagta   2580
aatttaaaag ttagacacac atggtggtgt atgcctgtag tcccagctac ataggaggct   2640
gaagtgggag gatcatttga ttgcaggagg ttgaggctgc agtgagcctt gttcatgcca   2700
ctccagcctg ggtggcagag tgagaccttg tctccaaaaa aaaaaaaaaa attgtcataa   2760
agtttcaaca tctgtgtcat cttagtgttg acatcccttg aggttttttc tcattcaagt   2820
ttacaatgtc ctagttcttg ttatgatgag tgactttggc tgtatcctgg tcatcttcac   2880
tgttatgaag ctctgggagt tatttaaatc tctcagcatg cttcctctga cggtgctggt   2940
```

```
atgggatggg gcactgcctc gttactgcct ggtgaggatg gagatccagg tttcctcctg   3000

tcgctgtcct cgggacctct gctgaggcct ttctgctgga agtaggagga gcaccctaat   3060

ggcaccgtgg gatagggagc aggccatgtt aggctggatg gtgaaagttt tcagcctgtg   3120

acgttgtctg gtgtgggtgg gtcccctttt tttgtgtgtg gtattttgct agagtaaggt   3180

agttatttcc taaaacttat ctgtcctgtt agttttcctt cttaagtacc taacaaatat   3240

aaagacaatg aactttaagc aataaaagac aatgatcctt tggagagggg aaacaaaa     3298
```

<210> SEQ ID NO 18
<211> LENGTH: 1348
<212> TYPE: DNA
<213> ORGANISM: Homo sapiens

<400> SEQUENCE: 18

```
actggactcc cgtgagctgg aaggaacaga tttaatatct aggggctggg tatccccaca     60

tcactcattt ggggggtcaa gggacccggg caatatagta ttctgctcag tgtctggaga    120

tcatctaccc aggctggggc ttctgggaca ggcgaggacc cacggaccct ggaagagctg    180

gtccagggga ctgaactccc ggcatcttta cagagcagag catgatcaca ttcctgccgc    240

tgctgctggg gctcagcctg ggctgcacag gagcaggtgg cttcgtggcc catgtggaaa    300

gcacctgtct gttggatgat gctgggactc caaaggattt cacatactgc atctccttca    360

acaaggatct gctgacctgc tgggatccag aggagaataa gatggcccct tgcgaatttg    420

gggtgctgaa tagcttggcg aatgtcctct cacagcacct caaccaaaaa gacaccctga    480

tgcagcgctt gcgcaatggg cttcagaatt gtgccacaca cacccagccc ttctggggat    540

cactgaccaa caggacacgg ccaccatctg tgcaagtagc caaaaccact cctttttaaca    600

cgagggagcc tgtgatgctg gcctgctatg tgtggggctt ctatccagca gaagtgacta    660

tcacgtggag gaagaacggg aagcttgtca tgcctcacag cagtgcgcac aagactgccc    720

agcccaatgg agactggaca taccagaccc tctcccattt agccttaacc ccctcttacg    780

gggacactta cacctgtgtg gtagagcaca ctggggctcc tgagcccatc cttcgggact    840

ggacacctgg gctgtccccc atgcagaccc tgaaggtttc tgtgtctgca gtgactctgg    900

gcctgggcct catcatcttc tctcttggtg tgatcagctg gcggagagct ggccactcta    960

gttacactcc tcttcctggg tccaattatt cagaaggatg gcacatttcc tagaggcaga   1020

atcctacaac ttccactcca agtgagaagg agattcaaac tcaatgatgc taccatgcct   1080

ctccaacatc ttcaaccccc tgacattatc ttggatccta tggtttctcc atccaattct   1140

ttgaatttcc cagtctcccc tatgtaaaac ttagcaactt gggggacctc attcctggga   1200

ctatgctgta accaaattat tgtccaaggc tatatttctg ggatgaatat aatctgagga   1260

agggagttaa agaccctcct ggggctctca gtgtgccata gaggacagca actggtgatt   1320

gtttcagaga aataaacttt ggtggaaa                                      1348
```

<210> SEQ ID NO 19
<211> LENGTH: 3464
<212> TYPE: DNA
<213> ORGANISM: Homo sapiens

<400> SEQUENCE: 19

```
gttcctgtcc tcaccacacg gactgagact gatttgatta aagcaccaga gtgtaatggc     60

cctcagagca gggctggtcc tggggttcca caccctgatg accctcctga gcccgcagga    120
```

```
ggcaggggcc accaaggctg accacatggg ctcctacgga cccgccttct accagtctta    180
cggcgcctcg ggccagttca cccatgaatt tgatgaggaa cagctgttct ctgtggacct    240
gaagaaaagc gaggccgtgt ggcgtctgcc tgagtttggt gactttgccc gctttgaccc    300
gcagggcggg ctggccggca tcgccgcaat caaagcccat ctggacatcc tggtggagcg    360
ctccaaccgc agcagagcca tcaacgtgcc tccacgggtg accgtgctcc ccaagtctcg    420
ggtggagctg ggccagccca acatcctcat ctgcatcgtg gacaacatct tcccccctgt    480
gatcaatatc acctggctgc gcaacggcca aactgtcact gagggagtgg cccagaccag    540
cttctattcc cagcctgacc atttgttccg caagttccac tacctgccct tcgtgccctc    600
agccgaggac gtctatgact gccaggtgga gcactggggc ctggatgcgc cactcctcag    660
gcattgggag ctccaggtgc ctattccacc accagatgcc atggagaccc tggtctgtgc    720
cctgggcctg gccatcggcc tggtgggctt cctcgtgggc accgtcctca tcatcatggg    780
cacatatgtg tccagtgtcc ccaggtaatg atccttctga gagaaatgac ttgtgggaga    840
caccctgcag atcctcatgg gtttgtgaca gcccctgcgt gctcagtgcc ctttaagtgc    900
atcccgctgt gctgactttg agtgggatca acatctgtcc tacgggtccc ctctttttg    960
gccccagtat tcatggcagg gtttgttgga cacctactag cttcccttcc cattcaacac   1020
acacacacat tcttgctcta cccaaagctc tggctggcag cactaaatgc tttggtggtg   1080
tttgcactgt gtcctttcca ggccttggcc agttcttcca ggggtgaggc atgtggtgct   1140
ggggattggc agccatcctg gggcccacac aggtgtgtct tgctccattt ggcccattgt   1200
gtgttacttt gtgaatgagc catttcacat ggacttcatg aaatttgcct cctgagttca   1260
ggtttaccct gaaagggatg cagattatcc tgttcctcac gacccctcca gctaacaaca   1320
gttctgaagg gtgctgggac aggacaggct catggggact ccactcctgc ctgggtttac   1380
tctgtatgaa gaggccactg gtatcctgcc atgatgttat ctcctttttc tacttttccc   1440
tagagtccca tgcatgataa agagaggccc aaggcttgga taaggtggcc acttccctca   1500
gtggagtcag tcatgttagg taggaggtgg tagagtcggt ctgcgaggta tctcgtaaga   1560
ggggaggtcc acctagacac actctaaata tgtggcctag aagattttgg tctacttttc   1620
tgtgaacaga atttaaaaca tacaaagaga taaatcacca taccacatag tttatgtcag   1680
gaccaaaatg agcaatacag attacggttt tcaaaccaga atgcacataa gaactgcttg   1740
ggatcctttt aaaagtacag gcattggcct ggtgcagtgg ctcattcctg taatcccagc   1800
actttgggag gccaagggga caggactgct tgaggccaag aggtggaaac catcttgggc   1860
tacatagaga gaccccatct ctacaaagaa agatttaaaa attaaccagg catggtggct   1920
cgcacctgta ttcccagcca ctggggaggc tgaggccgga ggagtgcttg agcccaggag   1980
ttcaaggctg cagtgagcca agattgcgcc actgcactcc agcctaggtg acagagtgag   2040
accctgtctc taaataaata aataaataaa atataaaaat aacagtcatc acccagacct   2100
actgaattag aatctcggga gtgcaggggg cagcaacagg gaggctgtct tttctgagat   2160
ggggtctcac tctgtcacca ggctggagtg ccatggcatg atctcagctc actgcaacct   2220
ccacctcctg agttcaagcc attctcctgc ctcagcctcc tgagtagctg ggactacagg   2280
tgtgcgccac tacactcagc taatttttgt attttaagta gagacggggt ttcatcatgt   2340
tggccaggat ggcctccatc tcttgacctc gtgatccacc caccttccct cccaaagtac   2400
tggaattaca ggcattagcc actgtgccca gccgaggctg tcatttttaa ccggctctgg   2460
atgactctga tgcagccatc ctggaccttg gctgtggtct ggtaactgga acccagtgac   2520
```

```
gtaatcaggt gccatcgggg gtcatgggaa agggggatcc ccaaggtctg aggtggacta   2580
ggaaggcttt ctgaagaacc tgggtctgtt agggcatcag ccaatcaagg tacaagtaaa   2640
tagaggcaaa atgagggttt gaactgtgag cagttggtcc tggaaaagaa agaaaccaag   2700
agattatggg gactcaatgg gcttcttaag agagaataag ttgaaatcaa tgaccagaag   2760
accctgatgg aagtggagga gaatcatctc aggcaaactt tttgtgtgcc agtaacagaa   2820
accctctttg tgtgatcaca tgcaaagtat aggatatttg caatatagcc atggggagga   2880
gtgcagggcc caagggtaga ttttagccag gcctcccagg aacagaactc ggatccgaaa   2940
agcccagaga agctagagct gcccctccaa cactctcgga tccacatggt ctgtgttctc   3000
tagaccccc tgcatgttag cggtgttctc tctctgtgga ctgactgtcc ttctcagtga   3060
acatgtccac ccgacagctc ctgagtttat atcatctcaa ccctcacaac ccacagaggc   3120
tgtgtctcct agtcacagct ttaaattact ggaaaaataa atgactggcc aaacttggag   3180
caggtgtcca tcccagccct gtgtagttag agcaggaatc aagatctcaa cacaaatgtg   3240
gctgccaagc actcagcccc ggggcgaggg gtcaagttct tctcagagaa agaggaataa   3300
gttggttctc agaagacatc acaagatacg tgtgtaccca acaatctctg atctctgctg   3360
atcttttgct tagacgttaa cttgatgcat cattggaaag gtgtttctct catctctgtc   3420
ctaaggcttg ataaagtcat taaaattgtg ttcttttgac taaa                    3464
```

<210> SEQ ID NO 20
<211> LENGTH: 3991
<212> TYPE: DNA
<213> ORGANISM: Homo sapiens

<400> SEQUENCE: 20

```
ccttcttttc ctgactgcag ctcttttcat tttgccatcc ttttccagct ccatgatggt     60
tctgcaggtt tctgcggccc cccggacagt ggctctgacg gcgttactga tggtgctgct    120
cacatctgtg gtccagggca gggccactcc agagaattac cttttccagg gacggcagga    180
atgctacgcg tttaatggga cacagcgctt cctggagaga tacatctaca accgggagga    240
gttcgcgcgc ttcgacagcg acgtggggga gttccgggcg gtgacggagc tggggcggcc    300
tgctgcggag tactggaaca gccagaagga catcctggag gagaagcggg cagtgccgga    360
caggatgtgc agacacaact acgagctggg cgggcccatg accctgcagc gccgagtcca    420
gcctagggtg aatgtttccc cctccaagaa ggggcccttg cagcaccaca acctgcttgt    480
ctgccacgtg acggatttct acccaggcag cattcaagtc cgatggttcc tgaatggaca    540
ggaggaaaca gctggggtcg tgtccaccaa cctgatccgt aatggagact ggaccttcca    600
gatcctggtg atgctggaaa tgacccccca gcagggagat gtctacacct gccaagtgga    660
gcacaccagc ctggatagtc ctgtcaccgt ggagtggaag gcacagtctg attctgcccg    720
gagtaagaca ttgacgggag ctgggggctt cgtgctgggg ctcatcatct gtggagtggg    780
catcttcatg cacaggagga gcaagaaagt tcaacgagga tctgcataaa cagggttcct    840
gagctcactg aaaagactat tgtgccttag gaaaagcatt tgctgtgttt cgttagcatc    900
tggctccagg acagaccttc aacttccaaa ttggatactg ctgccaagaa gttgctctga    960
agtcagtttc tatcattctg ctctttgatt caaagcactg tttctctcac tgggcctcca   1020
accatgttcc cttcttctta gcaccacaaa taatcaaaac ccaacatgac tgtttgtttt   1080
cctttaaaaa tatgcaccaa atcatctctc atcacttttc tctgagggtt ttagtagaca   1140
```

```
gtaggagtta ataaagaagt tcattttggt ttaaacatag gaaagaagag aaccatgaaa   1200
atggggatat gttaactatt gtataatggg gcctgttaca catgacactc ttctgaattg   1260
actgtatttc agtgagctgc ccccaaatca agtttagtgc cctcatccat ttatgtctca   1320
gaccactatt cttaactatt caatggtgag cagactgcaa atctgcctga taggacccat   1380
attcccacag cactaattca acatatacct tactgagagc atgttttatc attaccatta   1440
agaagttaaa tgaacatcag aatttaaaat cataaatata atctaataca ctttaaccat   1500
tttctttgtg tgccatcaca aatactcctt aaccaaatac ggcttggact tttgaatgca   1560
tccaatagac gtcatttgtc gtctaagtct gcattcatcc accagcctag gcctcctgtc   1620
ttaattttca tacagacaga aatgactccc cactggggaa agagcaaagc aatacatgta   1680
gcactctttt tcaaacactg gtcttttttt ttttcttaac aatccaacat tgttatgtgt   1740
tttgcgtctc atattgacac cttttggtca aggtagagga catgtttgtt gtaagctttc   1800
tttttcgtgt agaggatgga ttcttcactc ctgatacaca caatcagtgc acagcagctc   1860
tcttatacat ccagttgatg ccttcagtct ccctggcttc ttacaagcat cttctgggcc   1920
ttgtgtgtcc ctgggcacct gtccctggtc aattcccgaa agctactgtg ctcctcttgc   1980
ccatctcccc ttgcaaataa tatcttccat cgggggaccg gcttcctcca atttcaggag   2040
aggtggggct gaaggcacag acttgggcgt cactggcaca gatataagta aatacagctg   2100
gagtctgcag agaggctgga ctgagtcagg gagtcaggaa agagaagcca cacacaagga   2160
caaccaatca tgtttctcat aatcttctta acctagggaa taggacacaa tcatttttc    2220
tttttaaaac atctttatcc ctgatcagcc tcatttcctc aaaaactata aaggaaaatg   2280
ctgctgactt gtttttgcgt agtaatttca gctgtcacat aataagctaa ggaagacagt   2340
atatagtaaa taaggaccct ttatctgtct tattttccct tttggcttca caggaaactt   2400
gtgagaaacc tatgcagcat aaaattaata tgatttcaat ccagggattc aacgatggaa   2460
ggaggtcatg agaatagcag aaagtcttca aatcgagatc attatgaaat cctcagaccc   2520
agagcacata aatcctaccc tcagagtcac tgagcagtta acattacaaa ttacaaacca   2580
tatccagtca gagtcattct ctttcctgct tgtctcctgt actcatgtta caggttaggg   2640
cagtaccccg agtggagtga acaatctctg gactaacact tgtcaggatc agaagctgag   2700
gtatctgcac ccacattaca ggaacaggat atgtgctcct agggaactga gggtgtcagg   2760
agatgaggaa tgtccctgga gtcacagaaa gaaggtatca gatgtgtctc actctgacat   2820
atgcaggtgt ttatgaaact ctgggatttc taaggaagga tgcagtgcag agacaggtcc   2880
cagaggagac aagagctgag agaccatcca aactgggacc accttgtcac tagacttcaa   2940
attttcaata ttgatagagt gttttctaag agtcaggccc tttgctgagt gctatgtgca   3000
gcaggatcaa aggcagccag gaggtagagg agtcttgagg tacatcagtc attggagttg   3060
aagagcagag attcaaagga aagttggaac tggagcttta aaggagatgt gaagtgggtg   3120
actcaacctc tgactcagaa aaattgatac ctgcagaaga aaaaacccgg cgggcttagg   3180
actcccagct gagtgttgta tcctccatcc ctttccacct ggtcccttca ttttctaccc   3240
ctcacagttc cctaacgaga aggtggtcca cccaacagac aacactgcct cagatggtta   3300
tcaaggggta ccctaagaag aaatcatctc accctctctt tgtccccatt tgtcaagtag   3360
cagtgaggcc gagccagggg atggtgaaag tggaaggagg tgggagttgg gcatcgggtg   3420
tgaagatgct cttgaaaggg gttttaataa ccacttgcta ccaggccagt gaacacttac   3480
catagttgat gccttttgag catgttgcat tgtaaactgt ccctgaaatt actgtgcact   3540
```

```
tggcttatgg gatgaaacat cctcctagtt cttttgtctc tcagcttctc tgaagtctca   3600

ttgagcacct tctcttcaat ttcttttaca cagtaagaat aggatcagct gtgctaaact   3660

aacaaatacc cagatatcca ggtttggctc atgttacacg tccaaagtaa gtcatgcagg   3720

aagctctgct catcatcgta ctcaggaagt caggctgaca gtctttctcc tgcacatctg   3780

ctcccagaac ctccccagca gaatgaaggg aacctaagaa tttattcact ggcttttaat   3840

gatccctcct agaaagaaca cacttctcgc atttcatttt ccaatgtaaa tcatatggct   3900

gcaactaact tcaaataagt gggaatactt gaaggtggaa aacatttaag aagtacacac   3960

taaataaata ataaaatact tctacaagag a                                  3991
```

```
<210> SEQ ID NO 21
<211> LENGTH: 1458
<212> TYPE: DNA
<213> ORGANISM: Homo sapiens

<400> SEQUENCE: 21

acaattgctc tacagctcag agcagcaact gctgaggctg ccttgggaag aagatgatcc     60

taaacaaagc tctgctgctg gggccctcg ccctgactgc cgtgatgagc ccctgtggag    120

gtgaagacat tgtggctgac catgttgcct cctatggtgt gaacttctac cagtctcacg    180

gtccctctgg ccagtacacc catgaatttg atggagacga ggagttctat gtggacctgg    240

agacgaaaga gactgtctgg cagttgccta tgtttagcaa atttataagt tttgacccgc    300

agagtgcact gagaaatatg gctgtgggaa aacacacctt ggaattcatg atgagacagt    360

ccaactctac cgctgccacc aatgaggttc ctgaggtcac agtgttttcc aagtttcctg    420

tgacgctggg tcagcccaac accctcatct gtcttgtgga caacatcttt cctcctgtgg    480

tcaacatcac ctggctgagc aatgggcact cagtcacaga aggtgtttct gagaccagct    540

tcctctccaa gagtgatcat tccttcttca agatcagtta cctcaccttc ctcccttctg    600

ctgatgagat ttatgactgc aaggtggagc actggggcct ggacgagcct cttctgaaac    660

actgggagcc tgagattcca gcccctatgt cagagctcac agagactttg gtctgcgccc    720

tggggttgtc tgtgggcctc atgggcattg tggtgggcac tgtcttcatc atccaaggcc    780

tgcgttcagt tggtgcttcc agacaccaag ggctcttatg aatcccatcc tgaaaaggaa    840

ggtgcatcac catctacagg agaagaagaa tggacttgct aaatgaccta gcactattct    900

ctggcctgat ttatcatatc ccttttctcc tccaaatgtt tcttctctca cctcttctct    960

gggacttaag gtgctatatt ccctcagagc tcacaaatgc ctttcaattc tttccctgac   1020

ctcctttcct gaattttttt attttctcaa atgttaccta ctaagggatg cctgggtaag   1080

ccactcagct acctaattcc tcaatgacct ttatctaaaa tctccatgga agcaataaat   1140

tccctttga tgcctctatt gaatttttcc catctttcat ctcagggctg actgagagca   1200

taacttagaa tggcgactc ttatgtttta ggccaatttc atatcattcc ccagatcata   1260

tttcaagtcc agtaacacag gagcaaccaa gtacagtgta tcctgataat ttgttgattt   1320

cttaactggt gttaatattt ctttcttcct tttgttccta cccttggcca ctgccagcca   1380

cccctcaatt caggtaccaa cgaaccctct gcccttggct cagaatggtt atagcagaaa   1440

tacaaaaaaa aaaaaaaa                                                 1458

<210> SEQ ID NO 22
<211> LENGTH: 1212
<212> TYPE: DNA
```

<213> ORGANISM: Homo sapiens

<400> SEQUENCE: 22

```
attaggtttg agctgtgttg actaccactg ctttttcctt ggtctcactt acgtcttgga     60
agatggctct gcagatccct ggaggctttt gggcagcagc tgtgaccgtg atgctggtga    120
tgctgagcac cccagtggct gaggccagag actttcccaa ggatttcttg gtccagttta    180
agggcatgtg ctacttcacc aacgggacag agcgcgtgcg cggtgtggcc agatacatct    240
ataaccgcga ggagtacggg cgcttcgaca gcgacgttgg ggagttccag gcggtgaccg    300
agctggggcg gagcatcgag gactggaaca actataagga cttcttggag caggagcggg    360
ccgcggtgga caaggtgtgc agacacaact acgaggcgga gctgcgcacg accttgcagc    420
ggcaagtgga gcccacagtg accatctccc catccaggac agaggccctc aaccaccaca    480
acctgctggt ctgctcggtg acagatttct atccagccca gatcaaagtc cggtggtttc    540
ggaatgacca ggaggagaca gccggtgttg tgtccacctc cctcattagg aatggtgact    600
ggaccttcca gattctggtg atgctggaaa taactcccca gcgtggagac atctacacct    660
gccaagtgga gcaccccagc ctccagagcc ccatcaccgt ggagtggcgg gctcagtctg    720
aatctgccca gagcaagatg ctgagtggca ttggaggctt cgtgctgggg ctgatcttcc    780
tcgggctggg ccttatcatc cgtcacaggg gtcagaaagg acctcgaggg cctccaccag    840
caggactcct gcactgactc ctgaggactt ttgtctggga ttggtcatca ctcttctgta    900
atgcccacct gcccctgccc agaattccta gctgcctgtg tcaccctgtc ccactgaggt    960
cagagtccta cagtggctca tgcagccaca ggtcaccttc tgtgatcccc atcccaaggc   1020
actggtggtg actctgcttc ctgcactgac ccagagcctc tgcctgtgca ctgcaagctg   1080
tgtctactca ggccccaagg ggcatctctg tttccattct ccccccacag acctgtcaag   1140
agaagcatga caaacaaaat catttacctg actttagtgc tttttcccat aattaaacct   1200
gattctgagt ta                                                       1212
```

<210> SEQ ID NO 23
<211> LENGTH: 1235
<212> TYPE: DNA
<213> ORGANISM: Homo sapiens

<400> SEQUENCE: 23

```
attcttgtct gttctgcctc actcccgagc tctactgact cccaacagag cgcccaagaa     60
gaaaatggcc ataagtggag tccctgtgct aggatttttc atcatagctg tgctgatgag    120
cgctcaggaa tcatgggcta tcaaagaaga acatgtgatc atccaggccg agttctatct    180
gaatcctgac caatcaggcg agtttatgtt tgactttgat ggtgatgaga ttttccatgt    240
ggatatggca aagaaggaga cggtctggcg gcttgaagaa tttggacgat ttgccagctt    300
tgaggctcaa ggtgcattgg ccaacatagc tgtggacaaa gccaacctgg aaatcatgac    360
aaagcgctcc aactatactc cgatcaccaa tgtacctcca gaggtaactg tgctcacaaa    420
cagccctgtg gaactgagag agcccaacgt cctcatctgt ttcatagaca agttcacccc    480
accagtggtc aatgtcacgt ggcttcgaaa tggaaaacct gtcaccacag gagtgtcaga    540
gacagtcttc ctgcccaggg aagaccacct tttccgcaag ttccactatc tccccttcct    600
gccctcaact gaggacgttt acgactgcag ggtggagcac tggggcttgg atgagcctct    660
tctcaagcac tgggagtttg atgctccaag ccctctccca gagactacag agaacgtggt    720
gtgtgccctg ggcctgactg tgggtctggt gggcatcatt attgggacca tcttcatcat    780
```

-continued

```
caagggattg cgcaaaagca atgcagcaga acgcaggggg cctctgtaag gcacatggag    840

gtgatggtgt ttcttagaga gaagatcact gaagaaactt ctgctttaat ggctttacaa    900

agctggcaat attacaatcc ttgacctcag tgaaagcagt catcttcagc attttccagc    960

cctatagcca ccccaagtgt ggatatgcct cttcgattgc tccgtactct aacatctagc   1020

tggcttccct gtctattgcc ttttcctgta tctattttcc tctatttcct atcattttat   1080

tatcaccatg caatgcctct ggaataaaac atacaggagt ctgtctctgc tatggaatgc   1140

cccatggggc atctcttgtg tacttattgt ttaaggtttc ctcaaactgt gatttttctg   1200

aacacaataa actattttga tgatcttggg tggaa                              1235
```